US010865424B2

(12) United States Patent
Rezania et al.

(10) Patent No.: US 10,865,424 B2
(45) Date of Patent: *Dec. 15, 2020

(54) UNIVERSAL DONOR CELLS

(71) Applicant: CRISPR THERAPEUTICS AG, Zug (CH)

(72) Inventors: Alireza Rezania, Cambridge, MA (US); Rebeca Ramos-Zayas, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/928,151

(22) Filed: Jul. 14, 2020

(65) Prior Publication Data

US 2020/0347411 A1    Nov. 5, 2020

Related U.S. Application Data

(63) Continuation of application No. 16/563,553, filed on Sep. 6, 2019, now Pat. No. 10,724,052.

(60) Provisional application No. 62/728,529, filed on Sep. 7, 2018.

(51) Int. Cl.
| | |
|---|---|
| *C12N 15/63* | (2006.01) |
| *C12N 15/79* | (2006.01) |
| *C12N 15/85* | (2006.01) |
| *C07H 21/04* | (2006.01) |
| *C12N 15/90* | (2006.01) |
| *C12N 5/0735* | (2010.01) |
| *C12N 5/074* | (2010.01) |
| *C12N 5/071* | (2010.01) |
| *C12N 9/22* | (2006.01) |
| *C12N 15/11* | (2006.01) |
| *C07K 14/705* | (2006.01) |
| *C07K 14/74* | (2006.01) |

(52) U.S. Cl.
CPC ...... *C12N 15/907* (2013.01); *C07K 14/70532* (2013.01); *C07K 14/70539* (2013.01); *C12N 5/0606* (2013.01); *C12N 5/0607* (2013.01); *C12N 5/0676* (2013.01); *C12N 5/0696* (2013.01); *C12N 9/22* (2013.01); *C12N 15/11* (2013.01); *C12N 15/85* (2013.01); *C12N 2310/20* (2017.05); *C12N 2506/02* (2013.01); *C12N 2506/03* (2013.01); *C12N 2506/45* (2013.01); *C12N 2800/80* (2013.01)

(58) Field of Classification Search
CPC ........ C12N 15/63; C12N 15/79; C12N 15/85; C12N 15/907; C12N 5/0602; C12N 2310/20; C12N 2510/00; C07H 21/02; C07H 21/04
USPC .......... 435/320.1, 455; 424/93.21; 536/23.1, 536/23.5
See application file for complete search history.

(56) References Cited

U.S. PATENT DOCUMENTS

| | | |
|---|---|---|
| 5,034,506 A | 7/1991 | Summerton et al. |
| 7,432,104 B2 | 10/2008 | Mitalipova et al. |
| 7,510,876 B2 | 3/2009 | D'Amour et al. |
| 7,541,185 B2 | 6/2009 | D'Amour et al. |
| 7,695,963 B2 | 4/2010 | Agulnick et al. |
| 7,695,965 B2 | 4/2010 | Martinson et al. |
| 7,964,402 B2 | 6/2011 | Terskikh et al. |
| 7,985,585 B2 | 7/2011 | D'Amour et al. |
| 8,008,075 B2 | 8/2011 | Green et al. |
| 8,129,182 B2 | 3/2012 | D'Amour et al. |
| 8,153,429 B2 | 4/2012 | Robins et al. |
| 8,187,878 B2 | 5/2012 | Dalton et al. |
| 8,211,699 B2 | 7/2012 | Robins et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,586,357 B2 | 11/2013 | D'Amour et al. |
| 8,633,024 B2 | 1/2014 | D'Amour et al. |
| 8,685,726 B2 | 4/2014 | Schulz et al. |
| 8,859,286 B2 | 10/2014 | Agulnick |
| 8,895,300 B2 | 11/2014 | Schulz |
| 9,109,245 B2 | 8/2015 | Agulnick et al. |
| 9,365,830 B2 | 6/2016 | Schulz et al. |
| 10,030,229 B2 | 7/2018 | Peterson et al. |

(Continued)

FOREIGN PATENT DOCUMENTS

| | | |
|---|---|---|
| WO | 92/04033 A1 | 3/1992 |
| WO | 01/83692 A2 | 11/2001 |

(Continued)

OTHER PUBLICATIONS

Lu et al., "Generating Hypoimmunogenic Human Embryonic Stem Cells by the Disruption of Beta 2-Microglobulin," Stem Cell Rev and Rep, 2013, pp. 806-813, vol. 9.

(Continued)

*Primary Examiner* — Shin Lin Chen

(74) *Attorney, Agent, or Firm* — Polsinelli PC; Tara A. Nealey; Shirley Bissen

(57) ABSTRACT

Genetically modified cells that are compatible with multiple subjects, e.g., universal donor cells, and methods of generating said genetic modified cells are provided herein. The universal donor cells comprise at least one genetic modification within or near at least one gene that encodes one or more MHC-I or MHC-II human leukocyte antigens or component or transcriptional regulator of the MHC-I or MHC-II complex, at least one genetic modification that increases the expression of at least one polynucleotide that encodes a tolerogenic factor, and optionally at least one genetic modification that increases or decreases the expression of at least one gene that encodes a survival factor.

16 Claims, 42 Drawing Sheets

Specification includes a Sequence Listing.

(56) References Cited

U.S. PATENT DOCUMENTS

| | | |
|---|---|---|
| 10,391,156 B2 | 8/2019 | Bhoumik et al. |
| 2005/0266554 A1 | 12/2005 | D'Amour et al. |
| 2006/0222633 A1 | 10/2006 | Shlomchik et al. |
| 2007/0122905 A1 | 5/2007 | D'Amour et al. |
| 2009/0170198 A1 | 7/2009 | Rezania |
| 2009/0269845 A1 | 10/2009 | Rezania |
| 2010/0015100 A1 | 1/2010 | Xu |
| 2010/0112692 A1 | 5/2010 | Rezania |
| 2010/0112693 A1 | 5/2010 | Rezania et al. |
| 2010/0233755 A1 | 9/2010 | D'Amour et al. |
| 2010/0272695 A1 | 10/2010 | Agulnick et al. |
| 2011/0014702 A1 | 1/2011 | Xu |
| 2011/0014703 A1 | 1/2011 | Xu et al. |
| 2011/0151560 A1 | 6/2011 | Xu |
| 2011/0151561 A1 | 6/2011 | Davis et al. |
| 2012/0052575 A1 | 3/2012 | Rezania |
| 2012/0052576 A1 | 3/2012 | Rezania |
| 2013/0189777 A1 | 7/2013 | Rezania |
| 2013/0330823 A1 | 12/2013 | Rezania |
| 2014/0068797 A1 | 3/2014 | Doudna et al. |
| 2014/0134195 A1 | 5/2014 | Russell |
| 2014/0162359 A1 | 6/2014 | Rezania |
| 2014/0186305 A1 | 7/2014 | Rezania |
| 2014/0186953 A1 | 7/2014 | Rezania |
| 2014/0242693 A1 | 8/2014 | Fryer et al. |
| 2014/0295552 A1 | 10/2014 | Fryer et al. |
| 2015/0218522 A1 | 8/2015 | Peterson et al. |
| 2015/0329828 A1 | 11/2015 | Rezania |
| 2016/0215268 A1 | 7/2016 | Fryer et al. |
| 2017/0029778 A1 | 2/2017 | Peterson et al. |
| 2018/0100158 A1 | 4/2018 | Del'Guidice et al. |
| 2019/0015487 A1 | 1/2019 | Bhoumik et al. |
| 2019/0223416 A1 | 7/2019 | Lesko |

FOREIGN PATENT DOCUMENTS

| | | |
|---|---|---|
| WO | 2013/090648 A1 | 6/2013 |
| WO | 2013/192005 A2 | 12/2013 |
| WO | 2015/065524 A2 | 5/2015 |
| WO | 2016/183041 A2 | 11/2016 |
| WO | 2017/079673 A1 | 5/2017 |
| WO | 2018/035387 A1 | 2/2018 |
| WO | 2018/089011 A1 | 5/2018 |
| WO | 2018/132783 A1 | 7/2018 |
| WO | 2019/076486 A1 | 4/2019 |
| WO | 2020/049535 A1 | 3/2020 |

OTHER PUBLICATIONS

Ma et al., "Highly Efficient Differentiation of Functional Hepatocytes From Human Induced Pluripotent Stem Cells," Stem Cells Translational Medicine, 2013, pp. 409-419, vol. 2.

Mak et al., "The Crystal Structure of TAL Effector PthXo1 Bound to Its DNA Target," Science, 2012, pp. 716-719, vol. 335.

Mateos-Gomez et al., "Mammalian Polymerase Theta Promotes Alternative-NHEJ and Suppresses Recombination," Nature, 2015, pp. 254-257, vol. 518.

Moscou et al., "A Simple Cipher Governs DNA Recognition by TAL Effectors," Science, 2009, p. 1501, vol. 326.

Nasevicius et al. "Effective targeted gene 'knockdown' in zebrafish," Nature Genetics, 2000, pp. 216-220, vol. 26.

Pagliuca et al., "Generation of Functional Human Pancreatic β Cells In Vitro," Cell, 2014, pp. 428-439, vol. 159.

Parham, "MHC Class I Molecules and KIRS in Human History, Health and Survival," Nature Reviews/Immunology, 2005, pp. 201-214, vol. 5.

Peer et al., "Special delivery: targeted therapy with small RNAs," Gene Therapy, 2011, pp. 1127-1133, vol. 18.

Pegram et al., "Activating and inhibitory receptors of natural killer cells," Immunology and Cell Biology, 2011, pp. 216-224, vol. 89.

Rezania et al., "Production of Functional Glucagon-Secreting α-Cells From Human Embryonic Stem Cells," Diabetes, 2011, pp. 239-247, vol. 60.

Rezania et al., "Maturation of Human Embryonic Stem Cell-Derived Pancreatic Progenitors Into Functional Islets Capable of Treating Pre-existing Diabetes in Mice," Diabetes, 2012, pp. 2016-2029, vol. 61.

Rezania et al., "Enrichment of Human Embryonic Stem Cell-Derived NKX6.1—Expressing Pancreatic Progenitor Cells Accelerates the Maturation of Insulin-Secreting Cells In Vivo," Stem Cells, 2013, pp. 2432-2442, vol. 31.

Rezania et al., "Reversal of diabetes with insulin-producing cells derived in vitro from human pluripotent stem cells," Nature Biotechnology, 2014, pp. 1121-1133, vol. 32, No. 11.

Rubinstein, "HLA Matching for Bone Marrow Transplantation—How Much Is Enough?," The New England Journal of Medicine, 2001, pp. 1842-1844, vol. 345, No. 25.

Russ et al., "Controlled induction of human pancreatic progenitors produces functional beta-like cells in vitro," The EMBO Journal, 2014, pp. 1759-1772, vol. 34, No. 13.

Sadelain et al., "Safe harbours for the integration of new DNA in the human genome," Nature Reviews/Cancer, 2012, pp. 51-58, vol. 12.

Sapranauskas et al., "The *Streptococcus thermophilus* CRISPR/Cas system provides immunity in *Escherichia coli*," Nucleic Acids Research, 2011, pp. 9275-9282, vol. 39, No. 21.

Sawitza et al., Bile acids induce hepatic differentiation of mesenchymal stem cells, Scientific Reports, 2015, pp. 1-15, vol. 5.

Scholpp et al., "Morpholino-Induced Knockdown of Zebrafish Engrailed Gens eng2 and eng3 Reveals Redundant and Unique Functions in Midbrain-Hindbrain Boundary Development," Genesis, 2001, pp. 129-133, vol. 30.

Schuldiner et al., "Selective Ablation of Human Embryonic Stem Cells Expressing a "Suicide" Gene," Stem Cells, 2003, pp. 257-265, vol. 21.

Schulz et al., "A Scalable System for Production of Functional Pancreatic Progenitors from Human Embryonic Stem ells," PLoS ONE, 2012, e37004, pp. 1-17, vol. 7, No. 5.

Segal et al., "Toward controlling gene expression at will: Selection and design of zinc finger domains recognizing each of the 5'-GNN-3' DNA target sequences," PNAS, 1999, pp. 2758-2763, vol. 96.

Steentoft et al., "Precision genome editing: A small revolution for glycobiology," Glycobiology, 2014, pp. 663-680, vol. 24, No. 8.

Takahashi et al., "Induction of Pluripotent Stem Cells from Mouse Embryonic and Adult Fibroblast Cultures by Defined Factors," Cell, 2006, pp. 663-676, vol. 126.

Tsai et al., "Dimeric CRISPR RNA-guided FokI nucleases for highly specific genome editing," Nature Biotechnology, 2014, pp. 569-576, vol. 32, No. 6.

Wang et al., "Cyclohexene Nucleic Acids (CeNA): Serum Stable Oligonucleotides that Activate RNase H and Increase Duplex Stability with Complementary RNA," Journal of the American Chemical Society, 2000, pp. 8595-8602, vol. 122, No. 36.

Wang et al., "Rapid and Efficient Assembly of Transcription Activator-Like Effector Genes by USER Cloning," Journal of Genetics and Genomics, 2014, pp. 339-347, vol. 41.

Weber et al., "A Modular Cloning System for Standardized Assembly of Multigene Constructs," PLoS ONE, 2011, e16765, pp. 1-11, vol. 6, No. 2.

Wolfs et al., "MegaTevs: single-chain dual nucleases for efficient gene disruption," Nucleic Acids Research, 2014, pp. 8816-8829, vol. 42, No. 13.

Zarcone et al., "Human Leukemia-derived Cell Lines and Clones as Models for Mechanistic Analysis of Natural Killer Cell-mediated Cytotoxicity," Cancer Research, 1987, pp. 2674-2682, vol. 47.

International Search Report and Written Opinion from related International Application No. PCT/IB2019/057555, dated Nov. 21, 2019, 16 pgs.

Han et al., "Generation of hypoimmunogenic human pluripotent stem cells", PNAS, 2019, pp. 10441-10446, vol. 116, No. 21.

Sluch et al., "CRISPR-editing of hESCs allows for production of immune evasive cells capable of differentiation to pancreatic progenitors for future type 1 diabetes therapy", Sep. 1, 2019, Abstract. Retrieved from the Internet: URL:https://27funs395cqh24ygs021so4j-wpengine.netdna-ssl.com/wp-content/uploads/2019/09/ViaCyte-CRISPR-EASD-Abstract-September-2019.pdf [retrieved Nov. 8, 2019].

(56) References Cited

OTHER PUBLICATIONS

Bluch et al., "CRISPR-editing of hESCs allows for production of immune evasive cells capable of differentiation to pancreatic progenitors for future type 1 diabetes therapy", Sep. 17, 2019, 6 pgs. Retrieved from the Internet: URL:http://ir.crisprtx.com/static-files/af584c8b-5264-4bdd-a409-fec52e06d365.
Office Action from U.S. Appl. No. 16/563,553 dated Feb. 27, 2020; 31 pgs.
Bauche et al., 2014, Geneseq Accession No. BBQ97661, Computer printout, pp. 5-7.
Cowan et al., 2016, N_Geneseq_201922, Accession No. BDA08012, computer printout, pp. 6-7 (Cowan 2016a).
Cowan et al., 2016, Geneseq Accession No. BDA07999, Computer printout, pp. 5-7 (Cowan 2016b).
Agulnick et al., "Insulin-Producing Endocrine Cells Differentiated In Vitro From Human Embryonic Stem Cells Function in Macroencapsulation Devices In Vivo," Stem Cells Translational Medicine, 2015, pp. 1214-1222, vol. 4.
Aquino-Lopez et al., "Interferon Gamma Induces Changes in Natural Killer (NK) Cell Ligand Expression and Alters NK Cell-Mediated Lysis of Pediatric Cancer Cell Lines," Frontiers in Immunology, 2017, pp. 1-12, vol. 8, No. 391.
Belfort et al., "Homing Endonucleases: From Genetic Anomalies to Programmable Genomic Clippers," Methods in Molecular Biology, 2014, pp. 1-27, vol. 1123.
Bix et al., "Rejection of class I MHC-deficient haemopoietic cells by irradiated MHC-matched mice," Nature, 1991, pp. 329-331, vol. 349.
Bosch et al., "Breaking the Code of DNA Binding Specificity of TAL-Type III Effectors," Science, 2009, pp. 1509-1512, vol. 326.
Boissel et al., "megaTALs: a rare-cleaving nuclease architecture for therapeutic genome engineering," Nucleic Acids Research, 2014, pp. 2591-2601, vol. 42, No. 4.
Boissel et al., "Assembly and Characterization of megaTALs for Hyperspecific Genome Engineering Applications," Chromosomal Mutagenesis, Methods in Molecular Biology, Second Edition, Chapter 9, 2015, pp. 171-196, vol. 1239.
Bonini et al., "HSV-TK Gene Transfer into Donor Lymphocytes for Control of Allogeneic Graft-Versus-Leukemia," Science, 1997, pp. 1719-1724, vol. 276.
Bordignon et al., "Transfer of the HSV-tk Gene into Donor Peripheral Blood Lymphocytes for In Vivo Modulation of Donor Anti-Tumor Immunity after Allogeneic Bone Marrow Transplantation," Human Gene Therapy, 1995, pp. 813-819, vol. 6.
Braasch et al., "Novel Antisense and Peptide Nucleic Acid Strategies for Controlling Gene Expression," Biochemistry, 2002, pp. 4503-4510, vol. 41, No. 14.
Ceccaldi et al., "Homologous recombination-deficient tumors are hyper-dependent on POLQ-mediated repair," Nature, 2015, pp. 258-262, vol. 518, and Supplementary Material.
Cermak et al., "Efficient design and assembly of custom TALEN and other TAL effector-based constructs for DNA targeting," Nucleic Acids Research, 2011, e82, pp. 1-11, vol. 39, No. 12.
Cermak et al., "Efficient Design and Assembly of Custom TALENs Using the Golden Gate Platform," Chromosomal Mutagenesis, Methods in Molecular Biology, Second Edition, Chapter 7, 2015, pp. 133-159, vol. 1239.
Cho et al., "Familiar ends with alternative endings," Nature, 2015, pp. 174-176, vol. 518.
Cox et al., "Therapeutic genome editing: prospects and challenges," Nature Medicine, 2015, pp. 121-131, vol. 21, No. 2.
D'Amour et al., "Production of pancreatic hormone-expressing endocrine cells from human embryonic stem cells," Nature Biotechnology, 2006, pp. 1392-1401, vol. 24, No. 11.
DeKelver et al., "Functional genomics, proteomics, and regulatory DNA analysis in isogenic settings using zinc finger nuclease-driven transgenesis into a safe harbor locus in the human genome," Genome Research, 2010, pp. 1133-1142, vol. 20.

Deltcheva et al., "CRISPR RNA maturation by trans-encoded small RNA and host factor RNase III," Nature, 2011, pp. 602-607, vol. 471.
Dreier et al., "Insights into the Molecular Recognition of the 5'-GNN-3' Family of DNA Sequences by Zinc Finger Domains," Journal of Molecular Biology, 2000, pp. 489-502, vol. 303.
Dreier et al., "Development of Zinc Finger Domains for Recognition of the 5'-ANN-3' Family of DNA Sequences and Their Use in the Construction of Artificial Transcription Factors," The Journal of Biological Chemistry, 2001, pp. 29466-29478, vol. 276, No. 31.
Dreier et al., "Development of Zinc Finger Domains for Recognition of the 5'-CNN-3' Family DNA Sequences and Their Use in the Construction of Artificial Transcription Factors," The Journal of Biological Chemistry, 2005, pp. 35588-35597, vol. 280, No. 42.
Duan et al., "Differentiation and Characterization of Metabolically Functioning Hepatocytes from Human Embryonic Stem Cells," Stem Cells, 2010, pp. 674-686, vol. 28.
Fleischhauer et al. "Bone Marrow-Allograft Rejection by T Lymphocytes Recognizing a Single Amino Acid Difference in HLA-B44," The New England Journal of Medicine, 1990, pp. 1818-1822, vol. 323, No. 26.
Fonfara et al., "Phylogeny of Cas9 determines functional exchangeability of dual-RNA and Cas9 among orthologous type II CRISPR-Cas systems," Nucleic Acids Research, 2014, pp. 2577-2590, vol. 42, No. 4.
Gebeyehu et al., "Novel biotinylated nucleotide—analogs for labeling and colorimetric detection of DNA," Nucleic Acids Research, 1987, pp. 4513-4534, vol. 15, No. 11.
Gornalusse et al., "HLA-E-expressing pluripotent stem cells escape allogeneic responses and lysis by NK cells," Nature Biotechnology, 2017, pp. 765-773, vol. 35.
Grau et al., "TALENoffer: genome-wide TALEN off-target prediction," Bioinformatics, 2013, pp. 2931-2932, vol. 29, No. 22.
Gross et al., "Pertussis Toxin Promoter Sequences Involved in Modulation," Journal of Bacteriology, 1989, pp. 4026-4030, vol. 171, No. 7.
Guilinger et al., "Fusion of catalytically inactive Cas9 to FokI nuclease improves the specificity of genome modification," Nature Biotechnology, 2014, pp. 577-582, vol. 32, No. 6.
Guilinger et al., "Broad Specificity Profiling of TALENs Results in Engineered Nucleases With Improved DNA Cleavage Specificity," Nature Methods, 2014, pp. 429-435, vol. 11, No. 4.
Hafez et al., "Homing endonucleases: DNA scissors on a mission," Genome, 2012, pp. 553-569, vol. 55.
Heasman, "Morpholino Oligos: Making Sense of Antisense?," Developmental Biology, 2002, pp. 209-214, vol. 243.
Jinek et al., "A Programmable Dual-RNA-Guided DNA Endonuclease in Adaptive Bacterial Immunity," Science, 2012, pp. 816-821, vol. 337.
Karabekian et al., "HLA Class I Depleted hESC as a Source of Hypoimmunogenic Cells for Tissue Engineering Applications," Tissue Engineering: Part A, 2015, pp. 2559-2571, vol. 21.
Kent et al., "Mechanism of Microhomology-Mediated End-Joining Promoted by Human DNA Polymerase Theta," Nature Structural and Molecular Biology, 2015, pp. 230-237, vol. 22, No. 3.
Kleinstiver et al., "The I-TevI Nuclease and Linker Domains Contribute to the Specificity of Monomeric TALENs," Genes/Genomes/Genetics, 2014, pp. 1155-1165, vol. 4.
Knoepfler, "Deconstructing Stem Cell Tumorigenicity: A Roadmap to Safe Regenerative Medicine," Stem Cells, 2009, pp. 1050-1056, vol. 27.
Lacerra et al., "Restoration of hemoglobin A synthesis in erythroid cells from peripheral blood of thalassemic patients," PNAS, 2000, pp. 9591-9596, vol. 97, No. 17.
Li et al., "Modularly assembled designer TAL effector nucleases for targeted gene knockout and gene replacement in eukaryotes," Nucleic Acids Research, 2011, pp. 6315-6325, vol. 39, No. 14.
Liu et al., "Validated Zinc Finger Protein Designs for All 16 GNN DNA Triplet Targets," The Journal of Biological Chemistry, 2002, pp. 3850-3856, vol. 277, No. 6.

|  | Neuronal cells | Pancreatic cells | Other lineages |
|---|---|---|---|
| Examples of targets | B2M Knock-out<br><br>B2M/HLA-G fusion Knock-in | B2M Knock-out<br>CIITA Knock-out<br>PD-L1 Knock-in<br>CTLA4-Ig Knock-in | HLA-ABC Knock-out<br>HLA-G Knock-in<br>CIITA Knock-out<br>CD47 Knock-in |
| Other targets/promoters | *Genes that confer cell survival*<br><br>*Suicide switches: HSV-tk, iCaspase9*<br><br>*Promoters: constitutive promoters, cell-specific promoters, endogenous promoters* | | |

Wild Type

B2M Knock-out C4

SEQUENCE LISTING

```
<160> NUMBER OF SEQ ID NOS: 44

<210> SEQ ID NO 1
<211> LENGTH: 20
<212> TYPE: DNA
<213> ORGANISM: Homo sapiens

<400> SEQUENCE: 1
gctactctct ctttctggcc                                         20

<210> SEQ ID NO 2
<211> LENGTH: 20
<212> TYPE: DNA
<213> ORGANISM: Homo sapiens

<400> SEQUENCE: 2
ggccgagatg tctcgctccg                                         20

<210> SEQ ID NO 3
<211> LENGTH: 20
<212> TYPE: DNA
<213> ORGANISM: Homo sapiens

<400> SEQUENCE: 3
cgcgagcaca gctaaggcca                                         20

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
cagacagcaa actcacccag                                         20
```

<210> SEQ ID NO 5
<211> LENGTH: 20
<212> TYPE: DNA
<213> ORGANISM: Artificial Sequence
<220> FEATURE:
<223> OTHER INFORMATION: Synthesized

<400> SEQUENCE: 5
aaactttgtc ccgaccctcc                                                   20

<210> SEQ ID NO 6
<211> LENGTH: 638
<212> TYPE: DNA
<213> ORGANISM: Homo sapiens

<400> SEQUENCE: 6
cctagaatga gcgcccggtg tcccaagctg gggcgcgcac cccagatcgg cgggcgccga       60
tgtacagaca gcaaactcac ccagtctagt gcatgccttc ttaaacatca cgagactcta      120
gaaaaggaaa ctgaaaacgg gaaagtccct ctctctaacc tggcactgcg tcgctggctt      180
ggagacaggt gacggtccct gcgggccttg tcctgattgg ctgggcacgc gtttaatata      240
agtggaggcg tcgcgctggc gggcattcct gaagctgaca gcattcgggc cgagatgtct      300
cgctccgtgg ccttagctgt gctcgcgcta ctctctcttt ctggcctgga ggctatccag      360
cgtgagtctc tcctacccte ccgctctggt ccttcctctc ccgtctgcac cctctgtggc      420
cctcgctgtg ctctctcgct ccgtgacttc ccttctccaa gttctccttg gtggcccgcc      480
gtggggctag tccagggctg gatctcgggg aagcggcggg gtggcctggg agtggggaag      540
ggggtgcgca cccgggacgc gcgctacttg cccctttcgg cggggagcag gggagacctt      600
tggcctacgg cgacgggagg gtcgggacaa agtttagg                              638

<210> SEQ ID NO 7
<211> LENGTH: 20
<212> TYPE: DNA
<213> ORGANISM: Artificial Sequence
<220> FEATURE:
<223> OTHER INFORMATION: Synthesized

<400> SEQUENCE: 7
tctgcagaag gctacccta                                                    20

<210> SEQ ID NO 8
<211> LENGTH: 24
<212> TYPE: DNA
<213> ORGANISM: Artificial Sequence
<220> FEATURE:
<223> OTHER INFORMATION: Synthesized

<400> SEQUENCE: 8
tgctgtgtct aagacctctt tcat                                              24

<210> SEQ ID NO 9
<211> LENGTH: 18
<212> TYPE: DNA
<213> ORGANISM: Artificial Sequence
<220> FEATURE:
<223> OTHER INFORMATION: Synthesized

<400> SEQUENCE: 9
gatttggacc tgcgagcg                                                     18

```
<210> SEQ ID NO 10
<211> LENGTH: 22
<212> TYPE: DNA
<213> ORGANISM: Artificial Sequence
<220> FEATURE:
<223> OTHER INFORMATION: Synthesized

<400> SEQUENCE: 10
caagcctggc aataaacaat ga                                              22

<210> SEQ ID NO 11
<211> LENGTH: 15
<212> TYPE: DNA
<213> ORGANISM: Artificial Sequence
<220> FEATURE:
<223> OTHER INFORMATION: Synthesized

<400> SEQUENCE: 11
ctgctgcctg aacat                                                      15

<210> SEQ ID NO 12
<211> LENGTH: 130
<212> TYPE: DNA
<213> ORGANISM: Artificial Sequence
<220> FEATURE:
<223> OTHER INFORMATION: Synthesized

<400> SEQUENCE: 12
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 13
<211> LENGTH: 800
<212> TYPE: DNA
<213> ORGANISM: Homo sapiens

<400> SEQUENCE: 13
gttctagggt ggaaactaag agaatgatgt acctagaggg cgctggaagc tctaaagccc      60
tagcagttac tgcttttact attagtggtc gttttttttct cccccccgcc ccccgacaaa    120
tcaacagaac aaagaaaatt acctaaacag caaggacata gggaggaact tcttggcaca     180
gaactttcca acacttttt cctgaaggga tacaagaagc aagaaaggta ctctttcact      240
aggaccttct ctgagctgtc ctcaggatgc ttttgggact attttttctta cccagagaat    300 ggagaaaccc tgcagggaat tcccaagctg tagttataaa cagaagttct ccttctgcta     360
ggtagcattc aaagatctta atcttctggg tttccgtttt ctcgaatgaa aaatgcaggt     420
ccgagcagtt aactggctgg ggcaccatta gcaagtcact tagcatctct ggggccagtc     480
tgcaaagcga gggggcagcc ttaatgtgcc tccagcctga agtcctagaa tgagcgcccg     540
gtgtcccaag ctggggcgcg caccccagat cggaggcgc cgatgtacag acagcaaact      600
cacccagtct agtgcatgcc ttcttaaaca tcacgagact ctaagaaaag gaaactgaaa     660
acgggaaagt ccctctctct aacctggcac tgcgtcgctg gcttggagac aggtgacggt     720
ccctgcgggc cttgtcctga ttggctgggc acgcgtttaa tataagtgga ggcgtcgcgc     780
tggcgggcat tcctgaagct                                                 800

<210> SEQ ID NO 14
<211> LENGTH: 380
<212> TYPE: DNA
```

<213> ORGANISM: Cytomegalovirus

<400> SEQUENCE: 14

| | | | | | |
|---|---|---|---|---|---|
| gacattgatt | attgactagt | tattaatagt | aatcaattac | ggggtcatta | gttcatagcc | 60 |
| catatatgga | gttccgcgtt | acataactta | cggtaaatgg | cccgcctggc | tgaccgccca | 120 |
| acgaccccg | cccattgacg | tcaataatga | cgtatgttcc | catagtaacg | ccaataggga | 180 |
| ctttccattg | acgtcaatgg | gtggactatt | tacggtaaac | tgcccacttg | gcagtacatc | 240 |
| aagtgtatca | tatgccaagt | acgccccta | ttgacgtcaa | tgacggtaaa | tggcccgcct | 300 |
| ggcattatgc | ccagtacatg | accttatggg | actttcctac | ttggcagtac | atctacgtat | 360 |
| tagtcatcgc | tattaccatg | | | | | 380 |

<210> SEQ ID NO 15
<211> LENGTH: 276
<212> TYPE: DNA
<213> ORGANISM: Gallus gallus

<400> SEQUENCE: 15

| | | | | | |
|---|---|---|---|---|---|
| tcgaggtgag | ccccacgttc | tgcttcactc | tccccatctc | ccccccctcc | caccccaa | 60 |
| ttttgtattt | atttattttt | taattatttt | gtgcagcgat | gggggcgggg | gggggggggg | 120 |
| cgcgcgccag | gcggggcggg | gcggggcgag | gggcggggcg | gggcgaggcg | gagaggtgcg | 180 |
| gcggcagcca | atcagagcgg | cgcgctccga | aagtttcctt | ttatggcgag | gcggcggcgg | 240 |
| cggcggccct | ataaaaagcg | aagcgcgcgg | cgggcg | | | 276 |

<210> SEQ ID NO 16
<211> LENGTH: 1009
<212> TYPE: DNA
<213> ORGANISM: Artificial Sequence
<220> FEATURE:
<223> OTHER INFORMATION: Synthesized

<400> SEQUENCE: 16

| | | | | | |
|---|---|---|---|---|---|
| ggagtcgctg | cgttgccttc | gccccgtgcc | ccgctccgcg | ccgcctcgcg | ccgcccgccc | 60 |
| cggctctgac | tgaccgcgtt | actcccacag | gtgagcgggc | gggacggccc | ttctcctccg | 120 |
| ggctgtaatt | agcgcttggt | ttaatgacgg | ctcgtttctt | ttctgtggct | gcgtgaaagc | 180 |
| cttaaagggc | tccgggaggg | cccttttgtgc | gggggggagc | ggctcgggg | gtgcgtgcgt | 240 |
| gtgtgtgtgc | gtggggagcg | ccgcgtgcgg | cccgcgctgc | ccggcggctg | tgagcgctgc | 300 |
| gggcgcggcg | cgggcttttg | tgcgctccgc | gtgtgcgcga | ggggagcgcg | gccggggcg | 360 |
| gtgccccgcg | gtgcggggg | gctgcgaggg | gaacaaaggc | tgcgtgcggg | gtgtgtgcgt | 420 |
| gggggggtga | gcaggggtg | tgggcgcggc | ggtcgggctg | taaccccccc | ctgcaccccc | 480 |
| ctccccgagt | tgctgagcac | ggcccggctt | cgggtgcggg | gctccgtgcg | gggcgtggcg | 540 |
| cggggctcgc | cgtgccgggc | gggggtggc | ggcaggtggg | ggtgccgggc | ggggcgggc | 600 |
| cgcctcgggc | cggggagggc | tcgggggagg | ggcgcggcg | ccccggagcg | ccggcggctg | 660 |
| tcgaggcgcg | gcgagccgca | gccattgcct | tttatggtaa | tcgtgcgaga | gggcgcaggg | 720 |
| acttcctttg | tcccaaatct | ggcggagccg | aaatctggga | ggcgccgccg | caccccctct | 780 |
| agcgggcgcg | ggcgaagcgg | tgcggcgccg | gcaggaagga | aatgggcggg | gagggccttc | 840 |
| gtgcgtcgcc | gcgccgccgt | cccttctc | atctccagcc | tcggggctgc | cgcagggga | 900 |
| cggctgcctt | cggggggac | ggggcagggc | ggggttcggc | ttctggcgtg | tgaccggcgg | 960 |
| ctctagagcc | tctgctaacc | atgttcatgc | cttcttcttt | ttcctacag | | 1009 |

<210> SEQ ID NO 17
<211> LENGTH: 873
<212> TYPE: DNA
<213> ORGANISM: Homo sapiens

<400> SEQUENCE: 17

```
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattac tgtgaaagtc aatgccccat acaacaaaat caaccaaaga     420
atttttggttg tggatccagt cacctctgaa catgaactga catgtcaggc tgagggctac     480
cccaaggccg aagtcatctg acaagcagt gaccatcaag tcctgagtgg taagaccacc     540
accaccaatt ccaagagaga ggagaaactt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aaggactcac     720
ttggtaattc tgggagccat cttattatgc cttggtgtag cactgacatt catcttccgt     780
ttaagaaaag ggagaatgat ggatgtgaaa aatgtggca tccaagatac aaactcaaag     840
aagcaaagtg atacacattt ggaggagacg taa                                  873
```

<210> SEQ ID NO 18
<211> LENGTH: 225
<212> TYPE: DNA
<213> ORGANISM: Bos taurus

<400> SEQUENCE: 18

```
ctgtgccttc tagttgccag ccatctgttg tttgcccctc cccgtgcct tccttgaccc       60
tggaaggtgc cactcccact gtcctttcct aataaaatga ggaaattgca tcgcattgtc     120
tgagtaggtg tcattctatt ctgggggggtg gggtgggca ggacagcaag ggggaggatt     180
gggaagacaa tagcaggcat gctggggatg cggtgggctc tatgg                    225
```

<210> SEQ ID NO 19
<211> LENGTH: 800
<212> TYPE: DNA
<213> ORGANISM: Homo sapiens

<400> SEQUENCE: 19

```
ccagcgtgag tctctcctac cctcccgctc tggtccttcc tctcccgctc tgcaccctct      60
gtggccctcg ctgtgctctc tcgctccgtg acttccctt tccaagttct ccttggtggc     120
ccgccgtggg gctagtccag ggctggatct cggggaagcg gcggggtggc ctgggagtgg     180
ggaaggggt gcgcacccgg gacgcgcgct acttgcccct ttcggcgggg agcaggggag     240
acctttggcc tacggcgacg ggaggtcgg gacaaagttt aggggcgtcga taagcgtcag     300
agcgccgagg ttgggggagg gtttctcttc cgctctttcg cggggcctct ggctcccca     360
gcgcagctgg agtgggggac gggtaggctc gtcccaaagg cgcggcgctg aggtttgtga     420
acgcgtggag gggcgcttgg ggtctggggg aggcgtcgcc cgggtaagcc tgtctgctgc     480
```

```
ggctctgctt cccttagact ggagagctgt ggacttcgtc taggcgcccg ctaagttcgc      540
atgtcctagc acctctgggt ctatgtgggg ccacaccgtg gggaggaaac agcacgcgac      600
gtttgtagaa tgcttggctg tgatacaaag cggtttcgaa taattaactt atttgttccc      660
atcacatgtc acttttaaaa aattataaga actacccgtt attgacatct ttctgtgtgc      720
caaggacttt atgtgctttg cgtcatttaa ttttgaaaac agttatcttc cgccatagat      780
aactactatg gttatcttct                                                  800

<210> SEQ ID NO 20
<211> LENGTH: 141
<212> TYPE: DNA
<213> ORGANISM: Artificial Sequence
<220> FEATURE:
<223> OTHER INFORMATION: Synthesized

<400> SEQUENCE: 20
aggaacccct agtgatggag ttggccactc cctctctgcg cgctcgctcg ctcactgagg       60
ccgggcgacc aaaggtcgcc cgacgcccgg gctttgcccg ggcggcctca gtgagcgagc      120
gagcgcgcag ctgcctgcag g                                                141

<210> SEQ ID NO 21
<211> LENGTH: 60
<212> TYPE: DNA
<213> ORGANISM: Homo sapiens

<400> SEQUENCE: 21
atgtctcgct ccgtggcctt agctgtgctc gcgctactct ctctttctgg cctggaggct       60

<210> SEQ ID NO 22
<211> LENGTH: 27
<212> TYPE: DNA
<213> ORGANISM: Homo sapiens

<400> SEQUENCE: 22
gtcatggcgc cccgaaccct cttcctg                                           27

<210> SEQ ID NO 23
<211> LENGTH: 45
<212> TYPE: DNA
<213> ORGANISM: Artificial Sequence
<220> FEATURE:
<223> OTHER INFORMATION: Synthesized

<400> SEQUENCE: 23
ggtggaggcg gttcaggcgg aggtggctct ggcggtggcg gatcg                       45

<210> SEQ ID NO 24
<211> LENGTH: 297
<212> TYPE: DNA
<213> ORGANISM: Homo sapiens

<400> SEQUENCE: 24
atccagcgta ctccaaagat tcaggtttac tcacgtcatc cagcagagaa tggaaagtca       60
aatttcctga attgctatgt gtctgggttt catccatccg acattgaagt tgacttactg      120
aagaatggag agagaattga aaagtggag cattcagact tgtctttcag caaggactgg      180
tctttctatc tcttgtacta cactgaattc accccactg aaaaagatga gtatgcctgc      240
cgtgtgaacc atgtgacttt gtcacagccc aagatagtta gtgggatcg agacatg       297
```

```
<210> SEQ ID NO 25
<211> LENGTH: 60
<212> TYPE: DNA
<213> ORGANISM: Artificial Sequence
<220> FEATURE:
<223> OTHER INFORMATION: Synthesized

<400> SEQUENCE: 25
ggtggtggtg gttctggtgg tggtggttct ggcggcggcg gctccggtgg tggtggatcc      60

<210> SEQ ID NO 26
<211> LENGTH: 1011
<212> TYPE: DNA
<213> ORGANISM: Homo sapiens

<400> SEQUENCE: 26
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc  agagtattgg     180 gaccgggaga cacggagcgc cagggacacc gcacagattt tccgagtgaa tctgcggacg     240
ctgcgcggct actacaatca gagcgaggcc ggtctcaca  ccctgcagtg gatgcatggc     300
tgcgagctgg ggcccgacgg gcgcttcctc cgcgggtatg aacagttcgc ctacgacggc     360
aaggattatc tcaccctgaa tgaggacctg cgctcctgga ccgcggtgga cacggcggct     420
cagatctccg agcaaaagtc aaatgatgcc tctgaggcgg agcaccagag agcctacctg     480
gaagacacat gcgtggagtg gctccacaaa tacctggaga aggggaagga gacgctgctt     540
cacctggagc ccccaaagac acacgtgact caccacccca tctctgacca tgaggccacc     600
ctgaggtgct gggccctggg cttctaccct gcggagatca cactgacctg gcagcaggat     660
ggggagggcc atacccagga cacggagctc gtggagacca ggcctgcagg ggatggaacc     720
ttccagaagt gggcagctgt ggtggtgcct tctggagagg agcagagata cacgtgccat     780
gtgcagcatg aggggctacc cgagcccgtc accctgagat ggaagccggc ttcccagccc     840
accatcccca tcgtgggcat cattgctggc ctggttctcc ttggatctgt ggtctctgga     900
gctgtggttg ctgctgtgat atggaggaag aagagctcag gtgaaaagg agggagctac     960 tctaaggctg agtggagcga cagtgcccag gggtctgagt ctcacagctt g             1011

<210> SEQ ID NO 27
<211> LENGTH: 67
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(32)
<223> OTHER INFORMATION: n is a, c, g, or t
<220> FEATURE:
<221> NAME/KEY: misc_feature
<222> LOCATION: (43)..(58)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 27
ctnnnnnnnn nnnnnnnnnn nnnnnnnnnn nncgctccgt ggnnnnnnnn nnnnnnnngc      60 tanacgt                                                               67
```

```
<210> SEQ ID NO 28
<211> LENGTH: 64
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(32)
<223> OTHER INFORMATION: n is a, c, g, or t
<220> FEATURE:
<221> NAME/KEY: misc_feature
<222> LOCATION: (45)..(60)
<223> OTHER INFORMATION: n is a, c, g, or t

<400> SEQUENCE: 28
ctnnnnnnnn nnnnnnnnnn nnnnnnnnnn nncgcgctac ttagnnnnnn nnnnnnnnnn      60
gcta                                                                  64

<210> SEQ ID NO 29
<211> LENGTH: 63
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(32)
<223> OTHER INFORMATION: n is a, c, g, or t
<220> FEATURE:
<221> NAME/KEY: misc_feature
<222> LOCATION: (44)..(59)
<223> OTHER INFORMATION: n is a, c, g, or t

<400> SEQUENCE: 29
ctnnnnnnnn nnnnnnnnnn nnnnnnnnnn nncgcttccg tggnnnnnnn nnnnnnnnng      60
cta                                                                   63

<210> SEQ ID NO 30
<211> LENGTH: 26
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(22)
<223> OTHER INFORMATION: n is a, c, g, or t

<400> SEQUENCE: 30
ctaaggnnnn nnnnnnnnnn nngcta                                          26

<210> SEQ ID NO 31
<211> LENGTH: 39
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(32)
<223> OTHER INFORMATION: n is a, c, g, or t

<400> SEQUENCE: 31
ctnnnnnnnn nnnnnnnnnn nnnnnnnnnn nncgcgcta                            39

<210> SEQ ID NO 32
<211> LENGTH: 61
```

```
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(32)
<223> OTHER INFORMATION: n is a, c, g, or t
<220> FEATURE:
<221> NAME/KEY: misc_feature
<222> LOCATION: (42)..(57)
<223> OTHER INFORMATION: n is a, c, g, or t

<400> SEQUENCE: 32
ctnnnnnnnn nnnnnnnnnn nnnnnnnnnn nncgcccgtg gnnnnnnnnn nnnnnnngct    60
a                                                                    61

<210> SEQ ID NO 33
<211> LENGTH: 7133
<212> TYPE: DNA
<213> ORGANISM: Artificial Sequence
<220> FEATURE:
<223> OTHER INFORMATION: Synthesized

<400> SEQUENCE: 33
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac gcgtgttcta gggtggaaac taagagaatg atgtacctag   180
agggcgctgg aagctctaaa gccctagcag ttactgcttt tactattagt ggtcgttttt   240 ttctccccc cgcccccga caaatcaaca gaacaaagaa aattacctaa acagcaagga    300
catagggagg aacttcttgg cacagaactt ccaaacact ttttcctgaa gggatacaag    360
aagcaagaaa ggtactcttt cactaggacc ttctctgagc tgtcctcagg atgcttttgg   420 gactatttt cttacccaga gaatggagaa accctgcagg gaattcccaa gctgtagtta    480
taaacagaag ttctccttct gctaggtagc attcaaagat cttaatcttc tgggtttccg   540
ttttctcgaa tgaaaaatgc aggtccgagc agttaactgg ctggggcacc attagcaagt   600
cacttagcat ctctggggcc agtctgcaaa gcgagggggc agcctaatg tgcctccagc    660 ctgaagtcct agaatgagcg cccggtgtcc caagctgggg cgcgcacccc agatcggagg   720
gcgccgatgt acagacagca aactcaccca gtctagtgca tgccttctta aacatcacga   780
gactctaaga aaaggaaact gaaaacggga aagtccctct ctctaacctg gcactgcgtc   840
gctggcttgg agacaggtga cggtccctgc gggccttgtc ctgattggct gggcacgcgt   900
ttaatataag tggaggcgtc gcgctggcgg gcattcctga agctaagctt gtggacgata   960
tcgaattcgc acgacattga ttattgacta gttattaata gtaatcaatt acggggtcat   1020
tagttcatag cccatatatg gagttccgcg ttacataact tacggtaaat ggcccgcctg   1080
gctgaccgcc caacgacccc cgcccattga cgtcaataat gacgtatgtt cccatagtaa   1140
cgccaatagg gactttccat tgacgtcaat gggtggacta tttacggtaa actgcccact   1200
tggcagtaca tcaagtgtat catatgccaa gtacgccccc tattgacgtc aatgacggta   1260
aatggcccgc ctggcattat gcccagtaca tgaccttatg gactttcct acttggcagt    1320 acatctacgt attagtcatc gctattacca tgggtcgagg tgagccccac gttctgcttc   1380
actctcccca tctccccccc ctccccaccc ccaattttgt atttatttat ttttaatta    1440 ttttgtgcag cgatgggggc gggggggggg ggggcgcgcg ccaggcgggg cggggcgggg   1500
```

```
cgaggggcgg ggcggggcga ggcggagagg tgcggcggca gccaatcaga gcggcgcgct      1560
ccgaaagttt cctttttatgg cgaggcggcg cggcggcgg ccctataaaa agcgaagcgc      1620
gcggcgggcg ggagtcgctg cgttgccttc gccccgtgcc ccgctccgcg ccgcctcgcg      1680
ccgcccgccc cggctctgac tgaccgcgtt actcccacag gtgagcgggc gggacggccc      1740
ttctcctccg ggctgtaatt agcgcttggt ttaatgacgg ctcgtttctt ttctgtggct      1800
gcgtgaaagc cttaaagggc tccgggaggg ccctttgtgc ggggggggagc ggctcggggg     1860 gtgcgtgcgt gtgtgtgtgc gtggggagcg ccgcgtgcgg cccgcgctgc ccggcggctg     1920
tgagcgctgc gggcgcggcg cggggctttg tgcgctccgc gtgtgcgcga ggggagcgcg     1980
gccgggggcg gtgcccgcg gtgcgggggg gctgcgaggg gaacaaaggc tgcgtgcggg      2040
gtgtgtgcgt ggggggggtga gcaggggggtg tgggcgcggc ggtcgggctg taacccccccc   2100 ctgcaccccc ctccccgagt tgctgagcac ggcccggctt cgggtgcggg gctccgtgcg     2160
gggcgtggcg cggggctcgc cgtgccgggc gggggtggc ggcaggtggg ggtgccgggc      2220
ggggcggggc cgcctcgggc cggggagggc tcggggagg ggcgcggcgg ccccggagcg      2280
ccggcggctg tcgaggcgcg gcgagccgca gccattgcct tttatggtaa tcgtgcgaga     2340
gggcgcaggg acttcctttg tcccaaatct ggcggagccg aaatctggga ggcgccgccg     2400 cacccctct agcggggcgcg ggcgaagcgg tgcggcgccg gcaggaagga aatgggcggg    2460
gagggccttc gtgcgtcgcc gcgccgccgt ccccttctcc atctccagcc tcggggctgc    2520
cgcaggggga cggctgcctt cggggggggac ggggcagggc ggggttcggc ttctggcgtg   2580
tgaccggcgg ctctagagcc tctgctaacc atgttcatgc cttcttcttt ttcctacagg    2640
ggggatccgt ttatctgcag aattcgccct tgacgtcgcc accatgagga tatttgctgt    2700
ctttatattc atgaccctact ggcatttgct gaacgcattt actgtcacgg ttcccaagga   2760
cctatatgtg gtagagtatg gtagcaatat gacaattgaa tgcaaattcc cagtagaaaa    2820
acaattagac ctggctgcac taattgtcta ttgggaaatg gaggataaga acattattca    2880
atttgtgcat ggagaggaag acctgaaggt tcagcatagt agctacagac agagggcccg    2940
gctgttgaag gaccagctct ccctgggaaa tgctgcactt cagatcacag atgtgaaatt    3000
gcaggatgca ggggtgtacc gctgcatgat cagctatggt ggtgccgact acaagcgaat    3060
tactgtgaaa gtcaatgccc catacaacaa aatcaaccaa agaattttgg ttgtggatcc    3120
agtcacctct gaacatgaac tgacatgtca ggctgagggc tacccccaagg ccgaagtcat   3180 ctggacaagc agtgaccatc aagtcctgag tggtaagacc accaccacca attccaagag    3240
agaggagaaa cttttcaatg tgaccagcac actgagaatc aacacaacaa ctaatgagat    3300
tttctactgc acttttagga gattagatcc tgaggaaaac catacagctg aattggtcat    3360
cccagaacta cctctggcac atcctccaaa tgaaaggact cacttggtaa ttctgggagc    3420
catcttatta tgccttggtg tagcactgac attcatcttc cgtttaagaa aagggagaat    3480
gatggatgtg aaaaaatgtg gcatccaaga tacaaactca aagaagcaaa gtgatacaca    3540
tttggaggag acgtaaccgc tgatcagcct cgactgtgcc ttctagttgc cagccatctg    3600
ttgtttgccc ctcccccgtg ccttccttga ccctggaagg tgccactccc actgtccttt    3660
cctaataaaa tgaggaaatt gcatcgcatt gtctgagtag gtgtcattct attctggggg    3720
gtggggtggg gcaggacagc aaggggggagg attgggaaga caatagcagg catgctgggg   3780
atgcggtggg ctctatgggt cgaccagcg tgagtctctc ctaccctccc gctctggtcc     3840
ttcctctccc gctctgcacc ctctgtggcc ctcgctgtgc tctctcgctc cgtgacttcc    3900
```

```
cttctccaag ttctccttgg tggcccgccg tggggctagt ccagggctgg atctcgggga    3960
agcggcgggg tggcctggga gtggggaagg gggtgcgcac ccgggacgcg cgctacttgc    4020
cccttccggc ggggagcagg ggagaccttt ggcctacggc gacgggaggg tcgggacaaa    4080
gtttagggcg tcgataagcg tcagagcgcc gaggttgggg gagggtttct cttccgctct    4140
ttcgcggggc ctctggctcc cccagcgcag ctggagtggg ggacgggtag gctcgtccca    4200
aaggcgcggg gctgaggttt gtgaacgcgt ggaggggcgc ttggggtctg ggggaggcgt    4260
cgcccgggta agcctgtctg ctgcggctct gcttccctta gactggagag ctgtggactt    4320
cgtctaggcg cccgctaagt tcgcatgtcc tagcacctct gggtctatgt ggggccacac    4380
cgtggggagg aaacagcacg cgacgtttgt agaatgcttg gctgtgatac aaagcggttt    4440
cgaataatta acttatttgt tcccatcaca tgtcactttt aaaaaattat aagaactacc    4500
cgttattgac atctttctgt gtgccaagga ctttatgtgc tttgcgtcat ttaattttga    4560
aaacagttat cttccgccat agataactac tatggttatc ttctggtaac cacgtgcgga    4620
ccgaggctgc agcgtcgtcc tccctaggaa cccctagtga tggagttggc cactccctct    4680
ctgcgcgctc gctcgctcac tgaggccggg cgaccaaagg tcgcccgacg cccgggcttt    4740
gcccgggcgg cctcagtgag cgagcgagcg cgcagctgcc tgcaggggcg cctgatgcgg    4800
tattttctcc ttacgcatct gtgcggtatt tcacaccgca tacgtcaaag caaccatagt    4860
acgcgccctg tagcggcgca ttaagcgcgg cgggtgtggt ggttacgcgc agcgtgaccg    4920
ctacacttgc cagcgcccta gcgcccgctc ctttcgcttt cttcccttcc tttctcgcca    4980
cgttcgccgg ctttccccgt caagctctaa atcgggggct ccctttaggg ttccgattta    5040
gtgctttacg gcacctcgac cccaaaaaac ttgatttggg tgatggttca cgtagtgggc    5100
catcgccctg atagacggtt tttcgccctt gacgttgga gtccacgttc tttaatagtg    5160
gactcttgtt ccaaactgga acaacactca accctatctc gggctattct tttgatttat    5220
aagggatttt gccgatttcg gcctattggt taaaaaatga gctgatttaa caaaaattta    5280
acgcgaattt taacaaaata ttaacgttta caatttttatg gtgcactctc agtacaatct    5340
gctctgatgc cgcatagtta agccagcccc gacacccgcc aacacccgct gacgcgccct    5400
gacgggcttg tctgctcccg gcatccgctt acagacaagc tgtgaccgtc tccgggagct    5460
gcatgtgtca gaggttttca ccgtcatcac cgaaacgcgc gagacgaaag gcctcgtga    5520
tacgcctatt tttataggtt aatgtcatga caataaaac tgtctgctta cataaacagt    5580
aatacaaggg gtgttatgag ccatattcaa cgggaaacgt cgaggccgcg attaaattcc    5640
aacatggatg ctgatttata tgggtataaa tgggctcgcg ataatgtcgg gcaatcaggt    5700
gcgacaatct atcgcttgta tgggaagccc gatgcgccag agttgtttct gaaacatggc    5760
aaaggtagcg ttgccaatga tgttacagat gagatggtca gactaaactg gctgacggaa    5820
tttatgcctc ttccgaccat caagcatttt atccgtactc ctgatgatgc atggttactc    5880
accactgcga tccccggaaa aacagcattc caggtattag aagaatatcc tgattcaggt    5940
gaaaatattg ttgatgcgct ggcagtgttc ctgcgccggt tgcattcgat tcctgtttgt    6000
aattgtcctt ttaacagcga tcgcgtattt cgtctcgctc aggcgcaatc acgaatgaat    6060
aacggtttgg ttgatgcgag tgattttgat gacgagcgta atggctggcc tgttgaacaa    6120
gtctggaaag aaatgcataa acttttgcca ttctcaccgg attcagtcgt cactcatggt    6180
gatttctcac ttgataacct tattttgac gaggggaaat taataggttg tattgatgtt    6240
```

| | |
|---|---|
| ggacgagtcg gaatcgcaga ccgataccag gatcttgcca tcctatggaa ctgcctcggt | 6300 |
| gagttttctc cttcattaca gaaacggctt tttcaaaaat atggtattga taatcctgat | 6360 |
| atgaataaat tgcagtttca tttgatgctc gatgagtttt tctaatctca tgaccaaaat | 6420 |
| cccttaacgt gagttttcgt tccactgagc gtcagacccc gtagaaaaga tcaaaggatc | 6480 |
| ttcttgagat cctttttttc tgcgcgtaat ctgctgcttg caaacaaaaa aaccaccgct | 6540 |
| accagcggtg gtttgtttgc cggatcaaga gctaccaact cttttttccga aggtaactgg | 6600 |
| cttcagcaga gcgcagatac caaatactgt ccttctagtg tagccgtagt taggccacca | 6660 |
| cttcaagaac tctgtagcac cgcctacata cctcgctctg ctaatcctgt taccagtggc | 6720 |
| tgctgccagt ggcgataagt cgtgtcttac cgggttggac tcaagacgat agttaccgga | 6780 |
| taaggcgcag cggtcgggct gaacggggggg ttcgtgcaca cagcccagct tggagcgaac | 6840 |
| gacctacacc gaactgagat acctacagcg tgagctatga gaaagcgcca cgcttcccga | 6900 |
| agggagaaag gcggacaggt atccggtaag cggcagggtc ggaacaggag agcgcacgag | 6960 |
| ggagcttcca gggggaaacg cctggtatct ttatagtcct gtcgggtttc gccacctctg | 7020 |
| acttgagcgt cgatttttgt gatgctcgtc aggggggcgg agcctatgga aaaacgccag | 7080 |
| caacgcggcc ttttttacggt tcctggcctt ttgctggcct tttgctcaca tgt | 7133 |

<210> SEQ ID NO 34
<211> LENGTH: 7763
<212> TYPE: DNA
<213> ORGANISM: Artificial Sequence
<220> FEATURE:
<223> OTHER INFORMATION: Synthesized

<400> SEQUENCE: 34

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgcac gcgtgttcta gggtggaaac taagagaatg atgtacctag | 180 |
| agggcgctgg aagctctaaa gccctagcag ttactgcttt tactattagt ggtcgttttt | 240 |
| ttctcccccc cgcccccccga caaatcaaca gaacaaagaa aattacctaa acagcaagga | 300 |
| catagggagg aacttcttgg cacagaactt tccaaacact ttttcctgaa gggatacaag | 360 |
| aagcaagaaa ggtactcttt cactaggacc ttctctgagc tgtcctcagg atgcttttgg | 420 |
| gactattttt cttacccaga gaatggagaa accctgcagg gaattcccaa gctgtagtta | 480 |
| taaacagaag ttctccttct gctaggtagc attcaaagat cttaatcttc tgggtttccg | 540 |
| ttttctcgaa tgaaaaatgc aggtccgagc agttaactgg ctggggcacc attagcaagt | 600 |
| cacttagcat ctctgggggcc agtctgcaaa gcgagggggc agccttaatg tgcctccagc | 660 |
| ctgaagtcct agaatgagcg cccggtgtcc caagctgggg cgcgcacccc agatcggagg | 720 |
| gcgccgatgt acagacagca aactcaccca gtcagtgca tgccttctta aacatcacga | 780 |
| gactctaaga aaaggaaact gaaaacggga aagtccctct ctctaacctg gcactgcgtc | 840 |
| gctggcttgg agacaggtga cggtccctgc gggccttgtc ctgattggct gggcacgcgt | 900 |
| ttaatataag tggaggcgtc gcgctggcgg gcattcctga agctaagctt gtggacgata | 960 |
| tcgaattcgc acgacattga ttattgacta gttattaata gtaatcaatt acgggggtcat | 1020 |
| tagttcatag cccatatatg gagttccgcg ttacataact tacggtaaat ggcccgcctg | 1080 |
| gctgaccgcc caacgacccc cgcccattga cgtcaataat gacgtatgtt cccatagtaa | 1140 |
| cgccaatagg gactttccat tgacgtcaat gggtggacta tttacggtaa actgcccact | 1200 |

```
tggcagtaca tcaagtgtat catatgccaa gtacgccccc tattgacgtc aatgacggta    1260
aatggcccgc ctggcattat gcccagtaca tgaccttatg ggactttcct acttggcagt    1320
acatctacgt attagtcatc gctattacca tgggtcgagg tgagccccac gttctgcttc    1380
actctcccca tctcccccc ctcccacc ccaattttgt atttatttat tttttaatta    1440
ttttgtgcag cgatggggc ggggggggg ggggcgcgcg ccaggcgggg cggggcgggg    1500
cgaggggcgg ggcggggcga ggcggagagg tgcggcggca gccaatcaga gcggcgcgct    1560
ccgaaagttt cctttttatgg cgaggcggcg gcggcggcgg ccctataaaa agcgaagcgc    1620
gcggcgggcg ggagtcgctg cgttgccttc gccccgtgcc ccgctccgcg ccgcctcgcg    1680
ccgcccgccc cggctctgac tgaccgcgtt actcccacag gtgagcgggc gggacggccc    1740
ttctcctccg ggctgtaatt agcgcttggt ttaatgacgg ctcgtttctt ttctgtggct    1800
gcgtgaaagc cttaaagggc tccgggaggg ccctttgtgc ggggggagc ggctcggggg    1860 gtgcgtgcgt gtgtgtgtgc gtggggagcg ccgcgtgcgg cccgcgctgc ccggcggctg    1920
tgagcgctgc gggcgcggcg cggggctttg tgcgctccgc gtgtgcgcga ggggagcgcg    1980 gccggggggcg gtgccccgcg gtgcgggggg gctgcgaggg gaacaaaggc tgcgtgcggg    2040
gtgtgtgcgt gggggggtga gcagggggtg tgggcgcggc ggtcgggctg taacccccc    2100 ctgcaccccc ctccccgagt tgctgagcac ggcccggctt cggtgcggg gctccgtgcg    2160 gggcgtggcg cggggctcgc cgtgccgggc gggggtggc ggcaggtggg ggtgccgggc    2220 ggggcgggc cgcctcgggc cggggagggc tcggggagg ggcgcggcgg ccccggagcg    2280
ccggcggctg tcgaggcgcg gcgagccgca gccattgcct tttatggtaa tcgtgcgaga    2340
gggcgcaggg acttcctttg tcccaaatct ggcggagccg aaatctggga ggcgccgccg    2400 cacccctct agcgggcgcg ggcgaagcgg tgcgcgcccg gcaggaagga aatgggcggg    2460
gagggccttc gtgcgtcgcc gcgccgccgt ccccttctcc atctccagcc tcggggctgc    2520
cgcaggggga cggctgcctt cgggggggac ggggcagggc ggggttcggc ttctggcgtg    2580
tgaccggcgg ctctagagcc tctgctaacc atgttcatgc cttcttcttt ttcctacagg    2640
ggggatccgt ttatctgcag aattcgccct tgacgtcgcc accatgtctc gctccgtggc    2700
cttagctgtg ctcgcgctac tctctctttc tggcctggag gctgtcatgg cgccccgaac    2760
cctcttcctg ggtggaggcg gttcaggcgg aggtggctct ggcggtggcg gatcgatcca    2820
gcgtactcca aagattcagg tttactcacg tcatccagca gagaatggaa agtcaaattt    2880
cctgaattgc tatgtgtctg ggtttcatcc atccgacatt gaagttgact tactgaagaa    2940
tggagagaga attgaaaaag tggagcattc agacttgtct ttcagcaagg actggtcttt    3000
ctatctcttg tactacactg aattcacccc cactgaaaaa gatgagtatg cctgccgtgt    3060
gaaccatgtg actttgtcac agcccaagat agttaagtgg gatcgagaca tgggtggtgg    3120
tggttctggt ggtggtggtt ctggcggcgg cggctccggt ggtggtggat ccggctccca    3180
ctccttgaag tatttccaca cttccgtgtc ccggcccggc cgcgggggagc cccgcttcat    3240 ctctgtgggc tacgtggacg acacccagtt cgtgcgcttc gacaacgacg ccgcgagtcc    3300
gaggatggtg ccgcgggcgc cgtggatgga gcaggagggg tcagagtatt gggaccggga    3360
gacacggagc gccagggaca ccgcacagat tttccgagtg aatctgcgga cgctgcgcgg    3420
ctactacaat cagagcgagg ccgggtctca caccctgcag tggatgcatg gctgcgagct    3480
ggggcccgac gggcgcttcc tccgcgggta tgaacagttc gcctacgacg gcaaggatta    3540
```

-continued

```
tctcaccctg aatgaggacc tgcgctcctg gaccgcggtg gacacggcgg ctcagatctc    3600
cgagcaaaag tcaaatgatg cctctgaggc ggagcaccag agagcctacc tggaagacac    3660
atgcgtggag tggctccaca aatacctgga gaaggggaag gagacgctgc ttcacctgga    3720
gcccccaaag acacacgtga ctcaccaccc catctctgac catgaggcca ccctgaggtg    3780
ctgggccctg gcttctacc ctgcggagat cacactgacc tggcagcagg atggggaggg    3840
ccatacccag gacacggagc tcgtggagac caggcctgca ggggatggaa ccttccagaa    3900
gtgggcagct gtggtggtgc cttctggaga ggagcagaga tacacgtgcc atgtgcagca    3960 tgagggcta cccgagcccg tcaccctgag atggaagccg gcttcccagc ccaccatccc    4020
catcgtgggc atcattgctg gcctggttct ccttggatct gtggtctctg gagctgtggt    4080
tgctgctgtg atatggagga agaagagctc aggtggaaaa ggaggagct actctaaggc    4140 tgagtggagc gacagtgccc aggggtctga gtctcacagc ttgtaaccgc tgatcagcct    4200
cgactgtgcc ttctagttgc cagccatctg ttgtttgccc ctccccgtg ccttccttga    4260 ccctggaagg tgccactccc actgtccttt cctaataaaa tgaggaaatt gcatcgcatt    4320
gtctgagtag gtgtcattct attctggggg gtggggtggg gcaggacagc aaggggagg    4380 attgggaaga caatagcagg catgctgggg atgcggtggg ctctatgggt cgacccagcg    4440
tgagtctctc ctaccctccc gctctggtcc ttcctctccc gctctgcacc ctctgtggcc    4500
ctcgctgtgc tctctcgctc cgtgacttcc cttctccaag ttctccttgg tggcccgccg    4560 tgggctagt ccagggctgg atctcgggga agcggcgggg tggcctggga gtggggaagg    4620
gggtgcgcac ccgggacgcg cgctacttgc ccctttcggc ggggagcagg ggagaccttt    4680
ggcctacggc gacgggaggg tcgggacaaa gtttagggcg tcgataagcg tcagagcgcc    4740
gaggttgggg gagggtttct cttccgctct ttcgcggggc ctctggctcc cccagcgcag    4800
ctggagtggg ggacgggtag gctcgtccca aaggcgcggc gctgaggttt gtgaacgcgt    4860
ggaggggcgc ttggggtctg ggggaggcgt cgcccgggta agcctgtctg ctgcggctct    4920
gcttccctta gactggagag ctgtggactt cgtctaggcg cccgctaagt tcgcatgtcc    4980
tagcacctct gggtctatgt ggggccacac cgtggggagg aaacagcacg cgacgtttgt    5040
agaatgcttg gctgtgatac aaagcggttt cgaataatta acttatttgt tcccatcaca    5100
tgtcactttt aaaaaattat aagaactacc cgttattgac atctttctgt gtgccaagga    5160
ctttatgtgc tttgcgtcat ttaattttga aaacagttat cttccgccat agataactac    5220
tatggttatc ttctggtaac cacgtgcgga ccgaggctgc agcgtcgtcc tcctaggaa    5280 cccctagtga tggagttggc cactccctct ctgcgcgctc gctcgctcac tgaggccggg    5340
cgaccaaagg tcgcccgacg cccgggcttt gccggcgg cctcagtgag cgagcgagcg    5400
cgcagctgcc tgcaggggcg cctgatgcgg tattttctcc ttacgcatct gtgcggtatt    5460
tcacaccgca tacgtcaaag caaccatagt acgcgcctg tagcggcgca ttaagcgcgg    5520
cgggtgtggt ggttacgcgc agcgtgaccg ctacacttgc cagcgcccta gcgcccgctc    5580
ctttcgcttt cttcccttcc tttctcgcca cgttcgccgg ctttccccgt caagctctaa    5640
atcggggggt cccctttaggg ttccgattta gtgcttacg gcacctcgac cccaaaaaac    5700
ttgatttggg tgatggttca cgtagtgggc catcgccctg atagacggtt tttcgccctt    5760
tgacgttgga gtccacgttc tttaatagtg gactcttgtt ccaaactgga acaacactca    5820
accctatctc gggctattct tttgatttat aagggatttt gccgatttcg gcctattggt    5880
taaaaaatga gctgatttaa caaaaattta acgcgaattt aacaaaata ttaacgttta    5940
```

```
caattttatg gtgcactctc agtacaatct gctctgatgc cgcatagtta agccagcccc    6000
gacacccgcc aacacccgct gacgcgccct gacgggcttg tctgctcccg gcatccgctt    6060
acagacaagc tgtgaccgtc tccgggagct gcatgtgtca gaggttttca ccgtcatcac    6120
cgaaacgcgc gagacgaaag ggcctcgtga tacgccatt  tttataggtt aatgtcatga    6180
acaataaaac tgtctgctta cataaacagt aatacaaggg gtgttatgag ccatattcaa    6240
cgggaaacgt cgaggccgcg attaaattcc aacatggatg ctgatttata tgggtataaa    6300
tgggctcgcg ataatgtcgg gcaatcaggt gcgacaatct atcgcttgta tgggaagccc    6360
gatgcgccag agttgtttct gaaacatggc aaaggtagcg ttgccaatga tgttacagat    6420
gagatggtca gactaaactg gctgacggaa tttatgcctc ttccgaccat caagcatttt    6480
atccgtactc ctgatgatgc atggttactc accactgcga tccccggaaa acagcattc     6540 caggtattag aagaatatcc tgattcaggt gaaaatattg ttgatgcgct ggcagtgttc    6600
ctgcgccggt tgcattcgat tcctgttttgt aattgtcctt ttaacagcga tcgcgtattt    6660
cgtctcgctc aggcgcaatc acgaatgaat aacggtttgg ttgatgcgag tgattttgat    6720
gacgagcgta atggctggcc tgttgaacaa gtctggaaag aaatgcataa acttttgcca    6780
ttctcaccgg attcagtcgt cactcatggt gatttctcac ttgataacct tattttgac    6840 gagggaaat taataggttg tattgatgtt ggacgagtcg gaatcgcaga ccgataccag    6900
gatcttgcca tcctatggaa ctgcctcggt gagttttctc cttcattaca gaaacggctt    6960
tttcaaaaat atggtattga taatcctgat atgaataaat tgcagtttca tttgatgctc    7020
gatgagtttt tctaatctca tgaccaaaat cccttaacgt gagttttcgt tccactgagc    7080
gtcagacccc gtagaaaaga tcaaggatc  ttcttgagat cctttttttc tgcgcgtaat    7140
ctgctgcttg caaacaaaaa aaccaccgct accagcggtg gtttgtttgc cggatcaaga    7200
gctaccaact cttttccga aggtaactgg cttcagcaga gcgcagatac caaatactgt     7260
ccttctagtg tagccgtagt taggccacca cttcaagaac tctgtagcac cgcctacata    7320
cctcgctctg ctaatcctgt taccagtggc tgctgccagt ggcgataagt cgtgtcttac    7380
cgggttggac tcaagacgat agttaccgga taaggcgcag cggtcgggct gaacggggg    7440 ttcgtgcaca cagcccagct tggagcgaac gacctacacc gaactgagat acctacagcg    7500
tgagctatga gaaagcgcca cgcttcccga agggagaaag gcggacaggt atccggtaag    7560
cggcagggtc ggaacaggag agcgcacgag ggagcttcca ggggaaacg  cctggtatct    7620 ttatagtcct gtcgggtttc gccacctctg acttgagcgt cgatttttgt gatgctcgtc    7680 agggggggcgg agcctatgga aaaacgccag caacgcggcc ttttacggt tcctggcctt    7740 ttgctggcct tttgctcaca tgt                                            7763
```

<210> SEQ ID NO 35
<211> LENGTH: 20
<212> TYPE: DNA
<213> ORGANISM: Homo sapiens

<400> SEQUENCE: 35

```
tataagtgga ggcgtcgcgc                                                  20
```

<210> SEQ ID NO 36
<211> LENGTH: 20
<212> TYPE: DNA
<213> ORGANISM: Homo sapiens

```
<400> SEQUENCE: 36
gagtagcgcg agcacagcta                                              20

<210> SEQ ID NO 37
<211> LENGTH: 20
<212> TYPE: DNA
<213> ORGANISM: Homo sapiens

<400> SEQUENCE: 37
actggacgcg tcgcgctggc                                              20

<210> SEQ ID NO 38
<211> LENGTH: 20
<212> TYPE: DNA
<213> ORGANISM: Homo sapiens

<400> SEQUENCE: 38
aagtggaggc gtcgcgctgg                                              20

<210> SEQ ID NO 39
<211> LENGTH: 20
<212> TYPE: DNA
<213> ORGANISM: Homo sapiens

<400> SEQUENCE: 39
ggccacggag cgagacatct                                              20

<210> SEQ ID NO 40
<211> LENGTH: 20
<212> TYPE: DNA
<213> ORGANISM: Homo sapiens

<400> SEQUENCE: 40
gcccgaatgc tgtcagcttc                                              20

<210> SEQ ID NO 41
<211> LENGTH: 20
<212> TYPE: DNA
<213> ORGANISM: Homo sapiens

<400> SEQUENCE: 41
ctcgcgctac tctctctttc                                              20

<210> SEQ ID NO 42
<211> LENGTH: 20
<212> TYPE: DNA
<213> ORGANISM: Homo sapiens

<400> SEQUENCE: 42
tcctgaagct gacagcattc                                              20

<210> SEQ ID NO 43
<211> LENGTH: 20
<212> TYPE: DNA
<213> ORGANISM: Homo sapiens

<400> SEQUENCE: 43
ttcctgaagc tgacagcatt                                              20
```

```
<210> SEQ ID NO 44
<211> LENGTH: 20
<212> TYPE: DNA
<213> ORGANISM: Homo sapiens

<400> SEQUENCE: 44
actctctctt tctggcctgg                                              20
```

UNIVERSAL DONOR CELLS

RELATED APPLICATIONS

This application is a continuation of U.S. application Ser. No. 16/563,553, filed Sep. 6, 2019, now U.S. Pat. No. 10,724,052, which claims the benefit of U.S. Provisional Application No. 62/728,529, filed Sep. 7, 2018, the disclosure of each is hereby incorporated by reference in its entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Sep. 4, 2019, is named CT109-U.S. Pat. No. 1,000,867-635287-Sequence-Listing_ST25.txt, and is about 36,000 bytes in size.

FIELD OF THE INVENTION

The invention relates to the field of gene editing and, in some embodiments, to genetic modifications for the purposes of generating cells that are compatible with multiple subjects, e.g., universal donor cells.

BACKGROUND

Various approaches have been proposed to overcome allogeneic rejection of transplanted or engrafted cells including HLA-matching, blocking pathways that trigger T-cell activation with antibodies, use of a cocktail of immune suppressive drugs, and autologous cell therapy. Another strategy to dampen graft rejection involves minimization of allogenic differences between transplanted or engrafted cells and the recipient. The cell surface-expressed human leukocyte antigens (HLAs), molecules encoded by genes located in the human major histocompatibility complex on chromosome 6, are the major mediators of immune rejection. Mismatch of a single HLA gene between the donor and subject can cause a robust immune response (Fleischhauer K. et al. "Bone marrow-allograft rejection by T lymphocytes recognizing a single amino acid difference in HLA-B44," N Engl J Med., 1990, 323:1818-1822). HLA genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface.

In contrast to the wide cellular expression of MHC-I genes, expression of MHC-II genes is restricted to antigen-presenting cells such as dendritic cells, macrophages, and B cells. HLA antigen genes are the most polymorphic genes observed in the human genome (Rubinstein P., "HLA matching for bone marrow transplantation—how much is enough?" N Engl J Med., 2001, 345:1842-1844). The generation of a "universal donor" cell that is compatible with any HLA genotype provides an alternative strategy that could resolve the immune rejection and associated economical costs of current methodologies for immune evasion.

To generate such a line of universal donor cell(s), one previous approach has been to functionally disrupt the expression of MHC-I and MHC-II class genes. This could be achieved through genetic disruption, e.g., of both genetic alleles encoding the MHC-I light chain, B2M. The resulting B2M KO cell line and its derivatives would be expected to exhibit greatly reduced surface MHC-I and thus, reduced immunogenicity to allogeneic CD8+ T cells. The transcription activator-like effector nuclease (TALEN) targeting approach has been used to generate B2M-deficient hESC lines by deletion of a few nucleotides in exon 2 of the B2M gene (Lu, P. et al., "Generating hypoimmunogenic human embryonic stem cells by the disruption of beta 2-microglobulin," Stem Cell Rev. 2013, 9:806-813). Although the B2M-targeted hESC lines appeared to be surface HLA-I deficient, they were found to still contain mRNAs specific for B2M and MHC-I. The B2M and MHC-I mRNAs were expressed at levels equivalent to those of untargeted hESCs (both constitutive and IFN-g induced). Thus, concern exists that these TALEN B2M-targeted hESC lines might express residual cell surface MHC-I that would be sufficient to cause immune rejection, such as has been observed with B2M2/2 mouse cells that also express B2M mRNA (Gross, R. and Rappuoli, R. "Pertussis toxin promoter sequences involved in modulation," Proc Natl Acad Sci, 1993, 90:3913-3917). Although the TALEN B2M targeted hESC lines were not examined for off-target cleavage events, the occurrence of nonspecific cleavage when using TALENs remains a significant issue that would impose a major safety concern on their clinical use (Grau, J. et al. "TALENoffer: genome-wide TALEN off-target prediction," Bioinformatics, 2013, 29:2931-2932; Guilinger J. P. et al. "Broad specificity profiling of TALENs results in engineered nucleases with improved DNA-cleavage specificity," Nat Methods 2014, 11:429-435). Further, another report generated IPS cells that escaped allogeneic recognition by knocking out a first B2M allele and knocking in a HLA-E gene at a second B2M allele, which resulted in surface expression of HLA-E dimers or trimers in the absence of surface expression of HLA-A, HLA-B, or HLA-C (Gornalusse, G. G. et al., "HLA-E-expressing pluripotent stem cells escape allogeneic responses and lysis by NK cells," Nature Biotechnology, 2017, 35, 765-773).

A potential limitation of some of the above strategies are that MHC class I-negative cells are susceptible to lysis by natural killer (NK) cells as HLA molecules serve as major ligand inhibitors to natural killer (NK) cells. Host NK cells have been shown to eliminate transplanted or engrafted B2M−/− donor cells, and a similar phenomenon occurs in vitro with MHC class-I-negative human leukemic lines (Bix, M. et al., "Rejection of class I MHC-deficient haemopoietic cells by irradiated MHC-matched mice," Nature, 1991, 349, 329-331; Zarcone, D. et al., "Human leukemia-derived cell lines and clones as models for mechanistic analysis of natural killer cell-mediated cytotoxicity," Cancer Res. 1987, 47, 2674-2682). Thus, there exists a need to improve upon previous methods to generate universal donor cells that can evade the immune response as well as a need to generate cells that can survive post-engraftment. As described herein, cell survival post-engraftment may be mediated by a host of other pathways independent of allogeneic rejection e.g., hypoxia, reactive oxygen species, nutrient deprivation, and oxidative stress. Also as described herein, genetic introduction of survival factors (genes and/or proteins) may help cells to survive post-engraftment. As described herein, a

SUMMARY

In some aspects, the present disclosure encompasses a method for generating a universal donor cell, the method comprising delivering to a pluripotent stem cell (PSC) (a) an RNA-guided nuclease; (b) a guide RNA (gRNA) targeting a target site in a beta-2-microglobulin (B2M) gene locus; and (c) a vector comprising a nucleic acid, the nucleic acid comprising (i) a nucleotide sequence homologous with a region located left of the target site in the B2M gene locus, (ii) a nucleotide sequence encoding a tolerogenic factor, and (iii) a nucleotide sequence homologous with a region located right of the target site in the B2M gene locus, wherein the B2M gene locus is cleaved at the target site and the nucleic acid is inserted into the B2M gene locus within 50 base pairs of the target site, thereby generating a universal donor cell, wherein the universal donor cell has increased immune evasion and/or cell survival compared to a PSC that does not comprise the nucleic acid inserted into the B2M gene locus.

In some embodiments, the gRNA comprises a nucleotide sequence comprising at least one of SEQ ID NOS: 1-3. In some embodiments, (i) in the nucleic acid consists essentially of a nucleotide sequence of SEQ ID NO: 13, and (iii) in the nucleic acid consists essentially of a nucleotide sequence of SEQ ID NO: 19.

In some embodiments, the tolerogenic factor is programmed death ligand 1 (PD-L1) or human leukocyte antigen E (HLA-E). In some embodiments, the nucleotide sequence encoding the tolerogenic factor is operably linked to an exogenous promoter. In some embodiments, the exogenous promoter is constitutive, cell type-specific, tissue-type specific, or temporally regulated. In some embodiments, the exogenous promoter is a CAG promoter.

In some embodiments, the vector is a plasmid vector. In some embodiments, the plasmid vector comprises a nucleotide sequence of SEQ ID NO: 33 or SEQ ID NO: 34.

In some embodiments, the RNA-guided nuclease is a Cas9 nuclease. In some embodiments, the Cas9 nuclease is linked to at least one nuclear localization signal (NLS). In some embodiments, the CRISPR nuclease is a *S. pyogenes* Cas9.

In some embodiments, the PSC is a pluripotent stem cell (PSC), an embryonic stem cell (ESC), an adult stem cell (ASC), an induced pluripotent stem cell (iPSC), or a hematopoietic stem and progenitor cell (HSPC). In some embodiments, the PSC is a human PSC.

In some aspects, the present disclosure provides a method for generating a universal donor cell, the method comprising delivering to a PSC (a) an RNA-guided nuclease; (b) a gRNA targeting a target site in a B2M gene locus; wherein the gRNA comprises a nucleotide sequence of SEQ ID NO: 2; and (c) a vector comprising a nucleic acid, the nucleic acid comprising (i) a nucleotide sequence homologous with a region located left of the target site in the B2M gene locus that consists essentially of SEQ ID NO: 13, (ii) a nucleotide sequence encoding a tolerogenic factor, and (iii) a nucleotide sequence homologous with a region located right of the target site in the B2M gene locus that consists essentially of SEQ ID NO:19, wherein the B2M gene locus is cleaved at the target site and the nucleic acid is inserted into the B2M gene locus within 50 base pairs of the target site, thereby generating the universal donor cell, wherein the universal donor cell has increased immune evasion and/or cell survival compared to a PSC that does not comprise the nucleic acid inserted into the B2M gene locus.

In some embodiments, the tolerogenic factor is programmed PD-L1 or HLA-E. In some embodiments, the nucleotide sequence encoding the tolerogenic factor is operably linked to an exogenous promoter. In some embodiments, the exogenous promoter is constitutive, cell type-specific, tissue-type specific, or temporally regulated. In some embodiments, the exogenous promoter is a CAG promoter.

In some embodiments, the vector is a plasmid vector. In some embodiments, the plasmid vector comprises a nucleotide sequence of SEQ ID NO: 33 or SEQ ID NO: 34.

In some embodiments, the RNA-guided nuclease is a Cas9 nuclease. In some embodiments, the Cas9 nuclease is linked to at least one nuclear localization signal (NLS). In some embodiments, the CRISPR nuclease is a *S. pyogenes* Cas9.

In some embodiments, the PSC is a pluripotent stem cell (PSC), an embryonic stem cell (ESC), an adult stem cell (ASC), an induced pluripotent stem cell (iPSC), or a hematopoietic stem and progenitor cell (HSPC). In some embodiments, the PSC is a human PSC.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiments disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

FIGS. 1A-1C provide specific gene editing strategies for immune evasion. FIG. 1A is a table that describes exemplary modifications for immune evasion in specified cell types.

FIG. 1B provides exemplary strategies for modifying a B2M locus. FIG. 1C provides exemplary strategies for modifying HLA-A, HLA-B/C, and CIITA loci.

FIG. 2 depicts a portion of the B2M gene (SEQ ID NO: 6) and locations of gRNAs (B2M-1, B2M-2, and B2M-3) for targeting exon 1. Also shown are the locations of PCR primers (B2MF2 and B2MR2).

FIG. 3A is a graph showing indel (insertions+deletions) frequencies of each B2M gRNA. B2M-1 gRNA provided an indel frequency of 2.5%+1.1% (n=2). B2M-2 gRNA provided an indel frequency of 87.6% 14.1% (n=2). B2M-3 gRNA provided an indel frequency of 63.9%±0.9% (n=2). FIGS. 3B and 3C are graphs showing a summary of distribution of indel outcomes for the B2M-2 (FIG. 3B) and B2M-3 (FIG. 3C) gRNAs.

FIG. 4A is a graph showing a summary of distribution of indel outcomes for the B2M-2 gRNA in iPSCs. FIG. 4B presents the clones homozygous ("Homo") for B2M knock-out (KO) and the clones heterozygous ("Hets") for B2M KO.

FIG. 6A presents expression in wild type cells. FIG. 6B shows expression in B2M KO clone C4. FIG. 6C presents expression in B2M KO clone C9. FIG. 6D shows expression in B2M KO clone C12.

FIG. 7A presents expression in wild type cells. FIG. 7B shows expression in B2M KO clone C4. FIG. 7C presents expression in B2M KO clone C9. FIG. 7D shows expression in B2M KO clone C12.

FIG. 22A shows B2M expression in wild type cells. FIG. 22B shows B2M expression in B2M KO cells. FIG. 22C shows B2M expression in PD-L1 KI/B2M KO cells. FIG. 22D shows PD-L1 expression in wild type cells.

FIG. 22E shows PD-L1 expression in B2M KO cells. FIG. 22F shows PD-L1 expression in PD-L1 KI/B2M KO cells.

FIG. 23A shows MHC class I expression in wild type cells. FIG. 23B shows MHC class I expression in B2M KO cells.

FIG. 23C shows MHC class I expression in PD-L1 KI/B2M KO cells. FIG. 23D shows MHC class II PD-L1 expression in wild type cells. FIG. 23E shows MHC class II expression in B2M KO cells. FIG. 23F shows MHC class II expression in PD-L1 KI/B2M KO cells.

FIG. 24A shows activation in wild type cells. FIG. 24B shows activation in PD-L1 KI/B2M KO cells. FIG. 24C shows activation in B2M KO cells. FIG. 24D summarizes T-cell activation in the various cells. One-way ANOVA (α=0.05 with Dunnett's multiple comparisons test) with "CFSE-T alone" set as control. *, p<0.05; , p<0.01; *, p<0.001; ****, p<0.0001. n.s.=not significant.

DETAILED DESCRIPTION

1. Definitions

Figure 1B:
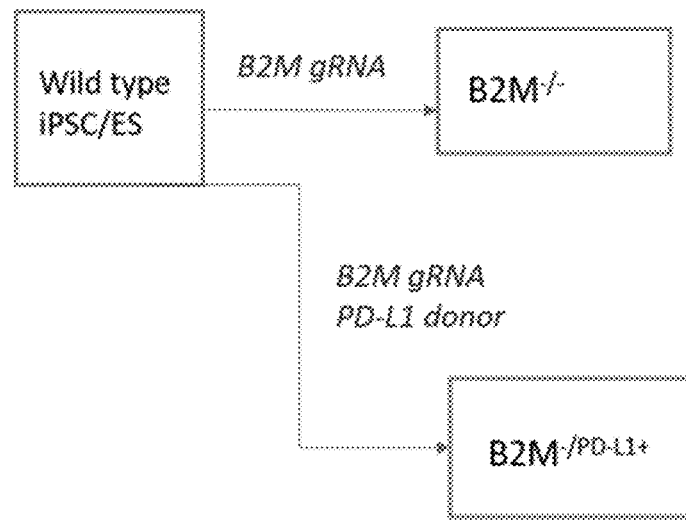

Deletion: As used herein, the term "deletion", which may be used interchangeably with the terms "genetic deletion" or "knock-out", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of an entire target gene, e.g., a B2M gene. In some embodiments, a deletion involves the removal of part of a target gene, e.g., all or part of a promoter and/or coding sequence of a B2M gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell.

Endonuclease:

As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In certain aspects, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

Genetic modification: As used herein, the term "genetic modification" generally refers to a site of genomic DNA that has been genetically edited or manipulated using any molecular biological method, e.g., methods described herein, e.g., by delivering to a site of genomic DNA an endonuclease and at least one gRNA. Example genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product.

Guide RNA (gRNA): As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

Insertion:

As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion occurs at a safe harbor locus. In some embodiments, an insertion involves the introduction of a polynucleotide that encodes a protein of interest. In some embodiments, an insertion involves the introduction of a polynucleotide that encodes a tolerogenic factor. In some embodiments, an insertion involves the introduction of a polynucleotide that encodes a survival factor. In some embodiments, an insertion involves the introduction of an exogenous promoter, e.g., a constitutive promoter, e.g., a CAG promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

Major Histocompatibility Complex Class I (MHC-I):

As used herein, the terms "Major histocompatibility complex class I" or "MHC-I" generally refer to a class of biomolecules that are found on the cell surface of all nucleated cells in vertebrates, including mammals, e.g., humans; and function to display peptides of non-self or foreign antigens, e.g., proteins, from within the cell (i.e. cytosolic) to cytotoxic T cells, e.g., CD8+ T cells, in order to stimulate an immune response. In some embodiments, a MHC-I biomolecule is a MHC-I gene or a MHC-I protein. Complexation of MHC-I proteins with beta-2 microglobulin (B2M) protein is required for the cell surface expression of all MHC-I proteins. In some embodiments, decreasing the expression of a MHC-I human leukocyte antigen (HLA) relative to an unmodified cell involves a decrease (or reduction) in the expression of a MHC-I gene. In some embodiments, decreasing the expression of a MHC-I human leukocyte antigen (HLA) relative to an unmodified cell involves a decrease (or reduction) in the cell surface expression of a MHC-I protein. In some embodiments, a MHC-I biomolecule is HLA-A (NCBI Gene ID No: 3105), HLA-B (NCBI Gene ID No: 3106), HLA-C(NCBI Gene ID No: 3107), or B2M (NCBI Gene ID No: 567).

Major Histocompatibility Complex Class II (MHC-II):

As used herein, the term "Major histocompatibility complex class II" or "MHC-II" generally refer to a class of biomolecules that are typically found on the cell surface of antigen-presenting cells in vertebrates, including mammals, e.g., humans; and function to display peptides of non-self or foreign antigens, e.g., proteins, from outside of the cell (extracellular) to cytotoxic T cells, e.g., CD8+ T cells, in order to stimulate an immune response. In some embodiments, an antigen-presenting cell is a dendritic cell, macrophage, or a B cell. In some embodiments, a MHC-II biomolecule is a MHC-I gene or a MHC-II protein. In some embodiments, decreasing the expression of a MHC-II human leukocyte antigen (HLA) relative to an unmodified cell involves a decrease (or reduction) in the expression of a MHC-II gene. In some embodiments, decreasing the expression of a MHC-II human leukocyte antigen (HLA) relative to an unmodified cell involves a decrease (or reduction) in the cell surface expression of a MHC-II protein. In some embodiments, a MHC-II biomolecule is HLA-DPA (NCBI Gene ID No: 3113), HLA-DPB (NCBI Gene ID No: 3115), HLA-DMA (NCBI Gene ID No: 3108), HLA-DMB (NCBI Gene ID No: 3109), HLA-DOA (NCBI Gene ID No: 3111), HLA-DOB (NCBI Gene ID No: 3112), HLA-DQA (NCBI Gene ID No: 3117), HLA-DQB (NCBI Gene ID No: 3119), HLA-DRA (NCBI Gene ID No: 3122), or HLA-DRB (NCBI Gene ID No: 3123).

Polynucleotide:

As used herein, the term "polynucleotide", which may be used interchangeably with the term "nucleic acid" generally refers to a biomolecule that comprises two or more nucleotides. In some embodiments, a polynucleotide comprises at least two, at least five at least ten, at least twenty, at least 30, at least 40, at least 50, at least 100, at least 200, at least 250, at least 500, or any number of nucleotides. A polynucleotide may be a DNA or RNA molecule or a hybrid DNA/RNA molecule. A polynucleotide may be single-stranded or double-stranded. In some embodiments, a polynucleotide is a site or region of genomic DNA. In some embodiments, a polynucleotide is an endogenous gene that is comprised within the genome of an unmodified cell or universal donor cell. In some embodiments, a polynucleotide is an exogenous polynucleotide that is not integrated into genomic DNA. In some embodiments, a polynucleotide is an exogenous polynucleotide that is integrated into genomic DNA. In some embodiments, a polynucleotide is a plasmid or an adeno-associated viral vector. In some embodiments, a polynucleotide is a circular or linear molecule.

Safe Harbor Locus:

As used herein, the term "safe harbor locus" generally refers to any location, site, or region of genomic DNA that may be able to accommodate a genetic insertion into said location, site, or region without adverse effects on a cell. In some embodiments, a safe harbor locus is an intragenic or extragenic region. In some embodiments, a safe harbor locus is a region of genomic DNA that is typically transcriptionally silent. In some embodiments, a safe harbor locus is a AAVS1 (PPP1 R12C), ALB, Angptl3, ApoC3, ASGR2, CCR5, FIX (F9), G6PC, Gys2, HGD, Lp(a), Pcsk9, Serpina1, TF, or TTR locus. In some embodiments, a safe harbor locus is described in Sadelain, M. et al., "Safe harbours for the integration of new DNA in the human genome," Nature Reviews Cancer, 2012, Vol 12, pages 51-58.

Safety Switch:

As used herein, the term "safety switch" generally refers to a biomolecule that leads a cell to undergo apoptosis. In some embodiments, a safety switch is a protein or gene. In some embodiments, a safety switch is a suicide gene. In some embodiments, a safety switch, e.g., herpes simplex virus thymidine kinase (HSV-tk), leads a cell to undergo apoptosis by metabolizing a prodrug, e.g., ganciclovir. In some embodiments, the overexpressed presence of a safety switch on its own leads a cell to undergo apoptosis. In some embodiments, a safety switch is a p53-based molecule, HSV-tk, or inducible caspase-9.

Subject:

As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

Survivalfactor:

As used herein, the term "survival factor" generally refers to a protein (e.g., expressed by a polynucleotide as described herein) that, when increased or decreased in a cell, enables the cell, e.g., a universal donor cell, to survive after transplantation or engraftment into a host subject at higher survival rates relative to an unmodified cell. In some embodiments, a survival factor is a human survival factor. In some embodiments, a survival factor is a member of a critical pathway involved in cell survival. In some embodiments, a critical pathway involved in cell survival has implications on hypoxia, reactive oxygen species, nutrient deprivation, and/or oxidative stress. In some embodiments, the genetic modification, e.g., deletion or insertion, of at least one survival factor enables a universal donor cell to survive for a longer time period, e.g., at least 1.05, at least 1.1, at least 1.25, at least 1.5, at least 2, at least 3, at least 4, at least 5, at least 10, at least 20, or at least 50 times longer time period, than an unmodified cell following engraftment. In some embodiments, a survival factor is ZNF143 (NCBI Gene ID No: 7702), TXNIP (NCBI Gene ID No: 10628), FOXO1 (NCBI Gene ID No: 2308), JNK (NCBI Gene ID No: 5599), or MANF (NCBI Gene ID No: 7873). In some embodiments, a survival factor is inserted into a cell, e.g., a universal donor cell. In some embodiments, a survival factor is deleted from a cell, a universal donor cell. In some embodiments, an insertion of a polynucleotide that encodes MANF enables a cell, e.g., a universal donor cell, to survive after transplantation or engraftment into a host subject at higher survival rates relative to an unmodified cell. In some embodiments, a deletion or insertion-deletion mutation within or near a ZNF143, TXNIP, FOXO1, or JNK gene enables a cell, e.g., a universal donor cell, to survive after transplantation or engraftment into a host subject at higher survival rates relative to an unmodified cell.

Tolerogenic Factor:

As used herein, the term "tolerogenic factor" generally refers to a protein (e.g., expressed by a polynucleotide as described herein) that, when increased or decreased in a cell, enables the cell, e.g., a universal donor cell, to inhibit or evade immune rejection after transplantation or engraftment into a host subject at higher rates relative to an unmodified cell. In some embodiments, a tolerogenic factor is a human tolerogenic factor. In some embodiments, the genetic modification of at least one tolerogenic factor (e.g., the insertion or deletion of at least one tolerogenic factor) enables a cell, e.g., a universal donor cell. to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, a tolerogenic factor is HLA-E (NCBI Gene ID No: 3133), HLA-G (NCBI Gene ID No: 3135), CTLA-4 (NCBI Gene ID No: 1493), CD47 (NCBI Gene ID No: 961), or PD-L1 (NCBI Gene ID No: 29126). In some embodiments, a tolerogenic factor is inserted into a cell, e.g., a universal donor cell. In some embodiments, a tolerogenic factor is deleted from a cell, e.g., a universal donor cell. In some embodiments, an insertion of a polynucleotide that encodes HLA-E, HLA-G, CTLA-4, CD47, and/or PD-L1 enables a cell, e.g., a universal donor cell, to inhibit or evade immune rejection after transplantation or engraftment into a host subject.

Transcriptional Regulator of MHC-I or MHC-II:

As used herein, the term "transcriptional regulator of MHC-I or MHC-II" generally refers to a biomolecule that modulates, e.g., increases or decreases, the expression of a MHC-I and/or MHC-II human leukocyte antigen. In some embodiments, a biomolecule is a polynucleotide, e.g., a gene, or a protein. In some embodiments, a transcriptional regulator of MHC-I or MHC-II will increase or decrease the cell surface expression of at least one MHC-I or MHC-II protein. In some embodiments, a transcriptional regulator of MHC-I or MHC-II will increase or decrease the expression of at least one MHC-I or MHC-II gene. In some embodiments, the transcriptional regulator is CIITA (NCBI Gene ID No: 4261) or NLRC5 (NCBI Gene ID No: 84166). In some embodiments, deletion or reduction of expression of CIITA or NLRC5 decreases expression of at least one MHC-I or MHC-II gene.

Universal Donor Cell:

As used herein, the term "universal donor cell" generally refers to a genetically modified cell that is less susceptible to allogeneic rejection during a cellular transplant and/or demonstrates increased survival after transplantation, relative to an unmodified cell. In some embodiments, a genetically modified cell as described herein is a universal donor cell. In some embodiments, the universal donor cell has increased immune evasion and/or cell survival compared to an unmodified cell. In some embodiments, the universal donor cell has increased cell survival compared to an unmodified cell. In some embodiments, a universal donor cell may be a stem cell. In some embodiments, a universal donor cell may be an embryonic stem cell (ESC), an adult stem cell (ASC), an induced pluripotent stem cell (iPSC), or a hematopoietic stem or progenitor cell (HSPC). In some embodiments, a universal donor cell may be a differentiated cell. In some embodiments, a universal donor cell may be a somatic cell (e.g., immune system cells). In some embodiments, a universal donor cell is administered to a subject. In some embodiments, a universal donor cell is administered to a subject who has, is suspected of having, or is at risk for a disease. In some embodiments, the universal donor cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells.

Unmodified Cell:

As used herein, the term "unmodified cell" refers to a cell that has not been subjected to a genetic modification involving a polynucleotide or gene that encodes a MHC-I, MHC-I, transcriptional regulator of MHC-I or MHC-II, survival factor, and/or tolerogenic factor. In some embodiments, an unmodified cell may be a stem cell. In some embodiments, an unmodified cell may be an embryonic stem cell (ESC), an adult stem cell (ASC), an induced pluripotent stem cell (iPSC), or a hematopoietic stem or progenitor cell (HSPC). In some embodiments, an unmodified cell may be a differentiated cell. In some embodiments, an unmodified cell may be selected from somatic cells (e.g., immune system cells, e.g., a T cell, e.g., a CD8+ T cell). If a universal donor cell is compared "relative to an unmodified cell", the universal donor cell and the unmodified cell are the same cell type or share a common parent cell line, e.g., a universal donor iPSC is compared relative to an unmodified iPSC.

Within or Near a Gene:

As used herein, the term "within or near a gene" refers to a site or region of genomic DNA that is an intronic or extronic component of a said gene or is located proximal to a said gene. In some embodiments, a site of genomic DNA is within a gene if it comprises at least a portion of an intron or exon of said gene. In some embodiments, a site of genomic DNA located near a gene may be at the 5' or 3' end of said gene (e.g., the 5' or 3' end of the coding region of said gene). In some embodiments, a site of genomic DNA located near a gene may be a promoter region or repressor region that modulates the expression of said gene. In some embodiments, a site of genomic DNA located near a gene may be on the same chromosome as said gene. In some embodiments, a site or region of genomic DNA is near a gene if it is within 50 Kb, 40 Kb, 30 Kb, 20 Kb, 10 Kb, 5 Kb, 1 Kb, or closer to the 5' or 3' end of said gene (e.g., the 5' or 3' end of the coding region of said gene).

II. Genome Editing Methods

Genome editing generally refers to the process of modifying the nucleotide sequence of a genome, preferably in a precise or pre-determined manner. In some embodiments, genome editing methods as described herein, e.g., the CRISPR-endonuclease system, may be used to genetically modify a cell as described herein, e.g., to create a universal donor cell. In some embodiments, genome editing methods as described herein, e.g., the CRISPR-endonuclease system, may be used to genetically modify a cell as described herein, e.g., to introduce at least one genetic modification within or near at least one gene that decreases the expression of one or more MHC-I and/or MHC-II human leukocyte antigens or other components of the MHC-I or MHC-II complex relative to an unmodified cell; to introduce at least one genetic modification that increases the expression of at least one polynucleotide that encodes a tolerogenic factor relative to an unmodified cell; and/or to introduce at least one genetic modification that increases or decreases the expression of at least one gene that encodes a survival factor relative to an unmodified cell.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonuclease s, as described and illustrated herein.

CRISPR Endonuclease System

The CRISPR-endonuclease system is a naturally occurring defense mechanism in prokaryotes that has been repurposed as a RNA-guided DNA-targeting platform used for gene editing. CRISPR systems include Types I, II, III, IV, V, and VI systems. In some aspects, the CRISPR system is a Type II CRISPR/Cas9 system. In other aspects, the CRISPR system is a Type V CRISPR/Cprf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from *Streptococcus pyogenes*, although other Cas9 homologs may be used, e.g., *S. aureus* Cas9, *N. meningitidis* Cas9, *S. thermophilus* CRISPR 1 Cas9, *S. thermophilus* CRISPR 3 Cas9, or *T. denticola* Cas9. In other instance s, the CRISPR endonuclease is Cpf1, e.g., *L. bacterium* ND2006 Cpf1 or *Acidaminococcus* sp. BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Nal Acad Sci, 1999 96(6):2758-63; Dreier B et al., J Mol Biol., 2000, 303(4):489-502; Liu Q et al., J Biol Chem., 2002, 277(6):3850-6: Dreier et al., J Biol Chem., 2005, 280(42):35588-97; and Dreier et al., J Biol Chem. 2001, 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthononas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefited from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; L1 et al., Nucleic Acids Res., 2011, 39(14):6315-25; Weber et al., PLoS One., 2011, 6(2):e16765; Wang et al., J Genet Genomics, 2014, 41(6):339-47; and Cermak T et al., Methods Mol Biol., 2015 1239:133-59.

Honing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H—N—H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCa9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because Fod must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from *S. pyogenes*, US2014/0068797 Sequence ID No. 8 or Sapranauskas et al., *Nucleic Acids Res*, 39(21): 9275-9282 (2011). The endonuclease can comprise at least 70, 75, 80, 85, 90, 95, 97, 99, or 100% identity to a wild-type endonuclease (e.g., Cas9 from *S. pyogenes*, supra) over 10 contiguous amino acids. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from *S. pyogenes*, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

Guide RNAs

The present disclosure provides a guide RNAs (gRNAs) that can direct the activities of an associated endonuclease to a specific target site within a polynucleotide. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., *Science*, 2012, 337, 816-821 and Deltcheva et al., *Nature*, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonucleases binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, *S. pyogenes* Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonucleases binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3'end of the sgRNA sequence. In some embodiments, a sgRNA does comprise one or more uracils, e.g., at the 3'end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise a modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, $SCH_3$, F, OCN, $OCH_3$, $OCH_3$ $O(CH_2)n$ $CH_3$, $O(CH_2)n$ $NH_2$, or $O(CH_2)n$ $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O—, S—, or N-alkyl, O—, S—, or N-alkenyl; SOCH$_3$; SO$_2$ CH$_3$; ON$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—CH$_3$); 2'-propoxy (2'-OCH$_2$ CH$_2$CH$_3$); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77, 1980; Gebeyehu et al., Nucl Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Complexes of a Genome-Targeting Nucleic Acid and a Endonuclease

A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to endonuclease in the RNP can be 1:1. For example, the weight ratio of sgRNA to Cas9 endonuclease in the RNP can be 1:1.

Nucleic Acids Encoding System Components

The present disclosure provides a nucleic acid comprising a nucleotide sequence encoding a genome-targeting nucleic acid of the disclosure, an endonuclease of the disclosure, and/or any nucleic acid or proteinaceous molecule necessary to carry out the aspects of the methods of the disclosure. The encoding nucleic acids can be RNA, DNA, or a combination thereof.

The nucleic acid encoding a genome-targeting nucleic acid of the disclosure, an endonuclease of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology, 1990, 185, Academic Press, San Diego, Calif. Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), chicken beta-actin promoter (CBA), ubiquitin C promoter (UBC), a hybrid construct comprising the cytomegalovirus enhancer fused to the chicken beta-actin promoter (CAG), a hybrid construct comprising the cytomegalovirus enhancer fused to the promoter, the first exon, and the first intron of chicken beta-actin gene (CAG or CAGGS), murine stem cell virus promoter (MSCV), phosphoglycerate kinase-1 locus promoter (PGK), and mouse metallothionein-I promoter.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter, CAG promoter). In some cases, the promoter can be a spatially restricted and/or temporally restricted promoter (e.g., a tissue specific promoter, a cell type specific promoter, etc.).

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

III. Strategies to Evade Immune Response and Increase Survival

Described herein are strategies to enable genetically modified cells, i.e., universal donor cells, to evade immune response and/or increase their survival, or viability following engraftment into a subject. In some embodiments, these strategies enable universal donor cells to evade immune response and/or survive at higher success rates than an unmodified cell. In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell; and/or at least one genetic modification that alters the expression of at least one gene that encodes a survival factor relative to an unmodified cell.

In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell; and at least one genetic modification that alters the expression of at least one gene that encodes a survival factor relative to an unmodified cell. In other embodiments, genetically modified cells comprise at least one deletion or insertion-deletion mutation within or near at least one gene that alters the expression of one or more MHC-I and MHC-II human leukocyte antigens relative to an unmodified cell; and at least one insertion of a polynucleotide that encodes at least one tolerogenic factor at a site that partially overlaps, completely overlaps, or is contained within, the site of a deletion of a gene that alters the expression of one or more MHC-I and MHC-I HLAs. In yet other embodiments, genetically modified cells comprise at least one genetic modification that alters the expression of at least one gene that encodes a survival factor relative to an unmodified cell.

The genes that encode the major histocompatibility complex (MHC) are located on human Chr. 6p21. The resultant proteins coded by the MHC genes are a series of surface proteins that are essential in donor compatibility during cellular transplantation. MHC genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface. In addition, there are three non-classical MHC-Ib molecules (HLA-E, HLA-F, and HLA-G), which have immune regulatory functions. MHC-II biomolecule include HLA-DP, HLA-DM, HLA-DOA, HLA-DOB, HLA-DQ, and HLA-DR. Due to their primary function in the immune response, MHC-I and MHC-II biomolecules contribute to immune rejection following cellular engrafiment of non-host cells, e.g., cellular engraftment for purposes of regenerative medicine.

MHC-I cell surface molecules are composed of MHC-encoded heavy chains (HLA-A, HLA-B, or HLA-C) and the invariant subunit beta-2-microglobulin (B2M). Thus, a reduction in the concentration of B2M within a cell allows for an effective method of reducing the cell surface expression of MHC-I cell surface molecules.

In some embodiments, a cell comprises a genomic modification of one or more MHC-I or MHC-II genes. In some embodiments, a cell comprises a genomic modification of one or more polynucleotide sequences that regulates the expression of MHC-I and/or MHC-II. In some embodiments, a genetic modification of the disclosure is performed using any gene editing method including but not limited to those methods described herein.

In some embodiments, decreasing the expression of one or more MHC-I and MHC-II human leukocyte antigens relative to an unmodified cell is accomplished by targeting, e.g., for genetic deletion and/or insertion of at least one base pair, in a MHC-I and/or MHC-II gene directly. In some embodiments, decreasing the expression of one or more MHC-I and MHC-II human leukocyte antigens relative to an unmodified cell is accomplished by targeting, e.g., for genetic deletion, a CIITA gene. In some embodiments, decreasing the expression of one or more MHC-I and MHC-II human leukocyte antigens relative to an unmodified cell is accomplished by targeting, e.g., for genetic deletion, at least one transcriptional regulator of MHC-I or MHC-II. In some embodiments, a transcriptional regulator of MHC-I or MHC-II is a NLRC5, or CIITA gene. In some embodiments, a transcriptional regulator of MHC-I or MHC-II is a RFX5, RFXAP, RFXANK, NFY-A, NFY-B, NFY-C, IRF-1, and/or TAP1 gene.

In some embodiments, the genome of a cell has been modified to delete the entirety or a portion of a HLA-A, HLA-B, and/or HLA-C gene. In some embodiments, the genome of a cell has been modified to delete the entirety or a portion of a promoter region of a HLA-A, HLA-B, and/or HLA-C gene. In some embodiments, the genome of a cell has been modified to delete the entirety or a portion of a gene that encodes a transcriptional regulator of MHC-I or MHC-II. In some embodiments, the genome of a cell has been modified to delete the entirety or a portion of a promoter region of a gene that encodes a transcriptional regulator of MHC-I or MHC-II.

In some embodiments, the genome of a cell has been modified to decrease the expression of beta-2-microglobulin (B2M). B2M is a non-polymorphic gene that encodes a common protein subunit required for surface expression of all polymorphic MHC class I heavy chains. HLA-I proteins are intimately associated with B2M in the endoplasmic reticulum, which is essential for forming functional, cell-surface expressed HLA-I molecules. In some embodiments, the gRNA targets a site within the B2M gene comprising a 5' GCTACTCTCTCTTTCTGGCC 3' sequence (SEQ ID NO: 1). In some embodiments, the gRNA targets a site within the B2M gene comprising a 5' GGCCGAGATGTCTCGCTCCG 3' sequence (SEQ ID NO: 2). In some embodiments, the gRNA targets a site within the B2M gene comprising a 5' CGCGAGCACAGCTAAGGCCA 3' sequence (SEQ ID NO: 3). In alternate embodiments, the gRNA targets a site within the B2M gene comprising any of the following sequences: 5'-TATAAGTGGAGGCGTCGCGC-3' (SEQ ID NO: 35), 5'-GAGTAGCGCGAGCACAGCTA-3' (SEQ ID NO: 36), 5'-ACTGGACGCGTCGCGCTGGC-3' (SEQ ID NO: 37), 5'-AAGTGGAGGCGTCGCGCTGG-3' (SEQ ID NO: 38), 5-GGCCACGGAGCGAGACATCT-3' (SEQ ID NO: 39), 5'-GCCCGAATGCTGTCAGCTTC-3' (SEQ ID NO: 40). 5'-CTCGCGCTACTCTCTCTTTC-3' (SEQ ID NO: 41), 5'-TCCTGAAGCTGACAGCATTC-3' (SEQ ID NO: 42), 5'-TTCCTGAAGCTGACAGCATT-3' (SEQ ID NO: 43), or 5'-ACTCTCTCTTTCTGGCCTGG-3' (SEQ ID NO: 44). In some embodiments, the gRNA comprises a polynucleotide sequence of any one of SEQ ID NO: 1, SEQ ID NO: 2, SEQ ID NO: 3, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, or SEQ ID NO: 44. The gRNA/CRISPR nuclease complex targets and cleaves a target site in the B2M locus. Repair of a double-stranded break by NHEJ can result in a deletion of at least on nucleotide and/or an insertion of at least one nucleotide, thereby disrupting or eliminating expression of B2M. Alternatively, the B2M locus can be targeted by at least two CRISPR systems each comprising a different gRNA, such that cleavage at two sites in the B2M locus leads to a deletion of the sequence between the two cuts, thereby eliminating expression of B2M.

In some embodiments, the genome of a cell has been modified to decrease the expression of Class II transactivator (CIITA). CIITA is a member of the LR or nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-γ in most cell types.

In some embodiments, the genome of a cell has been modified to decrease the expression of the NLR family, CARD domain containing 5 (NLRC5). NLRC5 is a critical regulator of MHC-I-mediated immune responses and, similar to CIITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some embodiments, tolerogenic factors can be inserted or reinserted into genetically modified cells to create immune-privileged universal donor cells. In some embodiments, the universal donor cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, CI-inhibitor, and IL-35. In some embodiments, the genetic modification, e.g., insertion, of at least one polynucleotide encoding at least one tolerogenic factor enables a universal donor cell to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, an insertion of a polynucleotide that encodes HLA-E, HLA-G, CTLA-4, CD47, and/or PD-L1 enables a universal donor cell to inhibit or evade immune rejection after transplantation or engraftment into a host subject.

The polynucleotide encoding the tolerogenic factor generally comprises left and right homology arms that flank the sequence encoding the tolerogenic factor. The homology arms have substantial sequence homology to genomic DNA at or near the targeted insertion site. For example, the left homology arm can be a nucleotide sequence homologous with a region located to the left or upstream of the target site or cut site and the right homology arm can be a nucleotide sequence homologous with a region located to the right or downstream of the target site or cut site. The proximal end of each homology arm can be homologous to genomic DNA sequence abutting the cut site. Alternatively, the proximal end of each homology arm can be homologous to genomic DNA sequence located up to about 10, 20, 30, 40, 50, 60, or 70 nucleobases away from the cut site. As such, the polynucleotide encoding the tolerogenic factor can be inserted into the targeted gene locus within about 10, 20, 30, 40, 50, 60, or 70 base pairs of the cut site, and additional genomic DNA bordering the cut site (and having no homology to a homolog arm) can be deleted. The homology arms can range in length from about 50 nucleotides to several of thousands of nucleotides. In some embodiments, the homology arms can range in length from about 500 nucleotides to about 1000 nucleotides. The substantial sequence homology between the homology arms and the genomic DNA can be at least about 80%, at least about 85%, at least about 90%, at least about 95%, or at least about 99%.

In some embodiments, the homology arms are used with B2M guides (e.g., gRNAs comprising a nucleotide sequence of SEQ ID NO: 1-3 or 35-44). In some embodiments, the homology arms are designed to be used with any B2M guide that would eliminate the start site of the B2M gene. In some embodiments, the B2M homology arms can comprise or consist essentially of a polynucleotide sequence of SEQ ID NO: 13 or 19, or a polynucleotide sequence having at least 85%, 90%, 95%, or 99% sequence identity with that of SEQ ID NO: 13 or 19. In some embodiments, the left B2M homology arm can comprise or consist essentially of SEQ ID NO: 13, or a polynucleotide sequence having at least 85%, 90%, 95%, or 99% sequence identity with that of SEQ ID NO: 13. In some embodiments, the right B2M homology arm can comprise or consist essentially of SEQ ID NO: 19, or a polynucleotide sequence having at least 85%, 90%, 95%, or 99% sequence identity with that of SEQ ID NO: 19.

The at least one polynucleotide encoding at least one tolerogenic factor can be operably linked to an exogenous promoter. The exogenous promoter can be a constitutive, inducible, temporal-, tissue-, or cell type-specific promoter. In some embodiments, the exogenous promoter is a CMV, EFla, PGK, CAG, or UBC promoter.

In some embodiments, the at least one polynucleotide encoding at least one tolerogenic factor is inserted into a safe harbor locus, e.g., the AAVS 1 locus. In some embodiments, the at least one polynucleotide encoding at least one tolerogenic factor is inserted into a site or region of genomic DNA that partially overlaps, completely overlaps, or is contained within (i.e., is within or near) a MHC-I gene, MHC-II gene, or a transcriptional regulator of MHC-I or MHC-II.

In some embodiments, a polynucleotide encoding PD-L is inserted at a site within or near a B2M gene locus. In some embodiments, a polynucleotide encoding PD-L1 is inserted at a site within or near a B2M gene locus concurrent with, or following a deletion of all or part of a B2M gene or promoter. The polynucleotide encoding PD-L1 is operably linked to an exogenous promoter. The exogenous promoter can be a CMV promoter.

In some embodiments, a polynucleotide encoding HLA-E is inserted at a site within or near a B2M gene locus. In some embodiments, a polynucleotide encoding HLA-E is inserted at a site within or near a B2M gene locus concurrent with, or following a deletion of all or part of a B2M gene or promoter. The polynucleotide encoding HLA-E is operably linked to an exogenous promoter. The exogenous promoter can be a CMV promoter.

In some embodiments, a polynucleotide encoding HLA-G is inserted at a site within or near a HLA-A, HLA-B, or HLA-C gene locus. In some embodiments, a polynucleotide encoding HLA-G is inserted at a site within or near a HLA-A, HLA-B, or HLA-C gene locus concurrent with, or following a deletion of a HLA-A, HLA-B, or HLA-C gene or promoter.

In some embodiments, a polynucleotide encoding CD47 is inserted at a site within or near a CIITA gene locus. In some embodiments, a polynucleotide encoding CD47 is inserted at a site within or near a CIITA gene locus concurrent with, or following a deletion of a CIITA gene or promoter.

In some embodiments, a polynucleotide encoding HLA-G is inserted at a site within or near a HLA-A, HLA-B, or HLA-C gene locus concurrent with insertion of a polynucleotide encoding CD47 at a site within or near a CIITA gene locus.

In some embodiments, a cell comprises increased or decreased expression of one or more survival factors. In some embodiments, a cell comprises an insertion of one or more polynucleotide sequences that encodes a survival factor. In some embodiments, a cell comprises a deletion of one of more survival factors. In some embodiments, a genetic modification of the disclosure is performed using any gene editing method including but not limited to those methods described herein. In some embodiments, a cell comprises increased or decreased expression of at least one survival factor relative to an unmodified cell. In some embodiments, a survival factor is a member or a critical pathway involved in cell survival, e.g., hypoxia, reactive oxygen species, nutrient deprivation, and/or oxidative stress. In some embodiments, the genetic modification of at least one survival factor enables a universal donor cell to survive for a longer time period, e.g., at least 1.05, at least 1.1, at least 1.25, at least 1.5, at least 2, at least 3, at least 4, at least 5, at least 10, at least 20, or at least 50 times longer time period, than an unmodified cell following engraftment. In some embodiments, a survival factor is ZNF143, TXNIP, FOXO1, JNK, or MANF.

In some embodiments, a cell comprises an insertion of a polynucleotide that encodes MANF enables a universal donor cell to survive after transplantation or engraftment into a host subject at higher survival rates relative to an unmodified cell. In some embodiments, a polynucleotide that encodes MANF is inserted into a safe harbor locus. In some embodiments, a polynucleotide that encodes MANF is inserted into a gene belonging to a MHC-I, MHC-II, or transcriptional regulator of MHC-I or MHC-II.

In some embodiments, the genome of a cell has been modified to delete the entirety or a portion of a ZNF143, TXNIP, FOXO1, and/or JNK gene. In some embodiments, the genome of a cell has been modified to delete the entirety or a portion of a promoter region of a ZNF143, TXNIP, FOXO1, and/or JNK gene.

In some embodiments, more than one survival factor is genetically modified within a cell.

In certain embodiments, cells having no MHC-II expression and moderate expression of MHC-I are genetically modified to have no surface expression of MHC-I or MHC-II. In another embodiment, cells with no surface expression of MHC-I/II are further edited to have expression of PD-L1, e.g., insertion of a polynucleotide encoding PD-L1. In yet another embodiment, cells with no surface expression of MHC-I/I are further edited to have expression of PD-L1, e.g., insertion of a polynucleotide encoding PD-L1, and are also genetically modified to increase or decrease the expression of at least one gene that encodes a survival factor relative to an unmodified cell.

In some embodiments, the cells further comprise increased or decreased expression, e.g., by a genetic modification, of one or more additional genes that are not necessarily implicated in either immune evasion or cell survival post-engraftment. In some embodiments, the cells further comprise increased expression of one or more safety switch proteins relative to an unmodified cell. In some embodiments, the cells comprise increased expression of one or more additional genes that encode a safety switch protein. In some embodiments, a safety switch is also a suicide gene. In some embodiments, a safety switch is herpes simplex virus-1 thymidine kinase (HSV-tk) or inducible caspase-9. In some embodiments, a polynucleotide that encodes at least one safety switch is inserted into a genome, e.g., into a safe harbor locus. In some other embodiments, the one or more additional genes that are genetically modified encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival thereof integrated with the construct.

One aspect of the present invention provides a method of generating genome-engineered universal donor cells, wherein a universal donor cell comprises at least one targeted genomic modification at one or more selected sites in genome, the method comprising genetically engineering a cell type as described herein by introducing into said cells one or more construct of to allow targeted modification at selected site; introducing into said cells one or more double strand breaks at the selected sites using one or more endonuclease capable of selected site recognition; and culturing the edited cells to allow endogenous DNA repair to generate targeted insertions or deletions at the selected sites; thereby obtaining genome-modified universal donor cells. The universal donor cells generated by this method will comprise at least one functional targeted genomic modification, and wherein the genome-modified cells, if they are stem cells, are then capable of being differentiated into progenitor cells or fully-differentiated cells.

In some other embodiments, the genome-engineered universal donor cells comprise introduced or increased expression in at least one of HLA-E, HLA-G, CD47, or D-L1. In some embodiments, the genome-engineered universal donor cells are HLA class I and/or class II deficient. In some embodiment, the genome-engineered universal donor cells comprise B2M null or low. In some embodiments, the genome-engineered universal donor cells comprise integrated or non-integrated exogenous polynucleotide encoding one or more of HLA-E, HLA-G, and PD-L1 proteins. In some embodiments, said introduced expression is an increased expression from either non-expressed or lowly expressed genes comprised in said cells. In some embodiments, the non-integrated exogenous polynucleotides are introduced using Sendai virus, AAV, episomal, or plasmid. In some embodiment, the universal donor cells are B2M null, with introduced expression of one or more of HLA-E, HLA-G, PD-L1, and increased or decreased expression of at least one safety switch protein. In another embodiment, the universal donor cells are HLA-A, HLA-B, and HLA-C null, with introduced expression of one or more of HLA-E, HLA-G, PD-L1, and at least one safety switch protein. In some embodiment, the universal donor cells are B2M null, with introduced expression of one or more of HLA-E, HLA-G PD-L1, and increased or decreased expression of at least one survival factor, e.g., MANF. Methods of generating any of the genetically modified cells described herein are contemplated to be performed using at least any of the gene editing methods described herein.

IV. Cell Types

Cells as described herein, e.g., universal donor cells (and corresponding unmodified cells) may belong to any possible class of cell type. In some embodiments, a cell, e.g., universal donor cell (and corresponding unmodified cell) may be a mammalian cell. In some embodiments, a cell, e.g., universal donor cell (and corresponding unmodified cell) may be a human cell. In some embodiments, a cell, e.g., universal donor cell (and corresponding unmodified cell) may be a stem cell. In some embodiments, a cell, e.g., universal donor cell (and corresponding unmodified cell) may be a pluripotent stem cell (PSC). In some embodiments, a cell, e.g., a universal donor cell (and corresponding unmodified cell) may be an embryonic stem cell (ESC), an adult stem cell (ASC), an induced pluripotent stem cell (iPSC), or a hematopoietic stem or progenitor cell (HSPC). In some embodiments, a cell, e.g., universal donor cell (and corresponding unmodified cell) may be a differentiated cell. In some embodiments, a cell, e.g., universal donor cell (and corresponding unmodified cell) may be a somatic cell, e.g., an immune system cell or a contractile cell, e.g., a skeletal muscle cell.

The cells, e.g., universal donor stem cells, described herein may be differentiated into relevant cell types to assess HLA expression, as well as the evaluation of immunogenicity of the universal stem cell lines. In general, differentiation comprises maintaining the cells of interest for a period time and under conditions sufficient for the cells to differentiate into the differentiated cells of interest. For example, the universal stem cells disclosed herein may be differentiated into mesenchymal progenitor cells (MPCs), hypoimmunogenic cardiomyocytes, muscle progenitor cells, blast cells, endothelial cells (ECs), macrophages, hepatocytes, beta cells (e.g., pancreatic beta cells), pancreatic endoderm progenitors, pancreatic endocrine progenitors, or neural progenitor cells (NPCs).

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further.

Embryonic Stem Cells

The cells described herein may be embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as universal donor cells.

Adult Stem Cells

The cells described herein may be adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells.

Induced Pluripotent Stem Cells

The cells described herein may be induced pluripotent stem cells (iPSCs). An iPSC may be generated directly from an adult human cell by introducing genes that encode critical transcription factors involved in pluripotency, e.g., Oct4, Sox2, cMyc, and Klf4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain.

Human Hematopoietic Stem and Progenitor Cells

The cells described herein may be human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation.

Differentiation of Cells into Other Cell Types

Another step of the methods of the present disclosure may comprise differentiating cells into differentiated cells. The differentiating step may be performed according to any method known in the art. For example, human iPSCs are differentiated into definitive endoderm using various treatments, including activin and B27 supplement (Life Technologies). The definitive endoderm is further differentiated into hepatocyte, the treatment includes: FGF4, HGF, BMP2, BMP4, Oncostatin M, Dexamethason, etc. (Duan et al, Stem Cells, 2010; 28:674-686; Ma et al, Stem Cells Translational Medicine, 2013; 2:409-419). In another embodiment, the differentiating step may be performed according to Sawitza et al, Sci Rep. 2015; 5: 13320. A differentiated cell may be any somatic cell of a mammal, e.g., a human. In some embodiments, a somatic cell may be an endocrine secretory epithelial cell (e.g., thyroid hormone secreting cells, adrenal cortical cells), an exocrine secretory epithelial cell (e.g., salivary gland mucous cell, prostate gland cell), a hormone-secreting cell (e.g., anterior pituitary cell, pancreatic islet cell), a keratinizing epithelial cell (e.g., epidermal keratinocyte), a wet stratified barrier epithelial cell, a sensory transducer cell (e.g., a photoreceptor), an autonomic neuron cells, a sense organ and peripheral neuron supporting cell (e.g., Schwann cell), a central nervous system neuron, a glial cell (e.g., astrocyte, oligodendrocyte), a lens cell, an adipocyte, a kidney cell, a barrier function cell (e.g., a duct cell), an extracellular matrix cell, a contractile cell (e.g., skeletal muscle cell, heart muscle cell, smooth muscle cell), a blood cell (e.g., erythrocyte), an immune system cell (e.g., megakaryocyte, microglial cell, neutrophil, mast cell, a T cell, a B cell, a Natural Killer cell), a germ cell (e.g., spermatid), a nurse cell, or an interstitial cell.

V. Formulations and Administrations

Formulation and Delivery for Gene Editing

Guide RNAs, polynucleotides, e.g., polynucleotides that encode a tolerogenic factor or polynucleotides that encode an endonuclease, and endonucleases as described herein may be formulated and delivered to cells in any manner known in the art.

Guide RNAs and/or polynucleotides may be formulated with pharmaceutically acceptable excipients such as carriers, solvents, stabilizers, adjuvants, diluents, etc., depending upon the particular mode of administration and dosage form. Guide RNAs and/or polynucleotides compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 2011, 18: 1127-1133 (which focuses on non-viral delivery vehicles for siRNA that are also useful for delivery of other polynucleotides).

For polynucleotides of the disclosure, the formulation may be selected from any of those taught, for example, in International Application PCT/US2012/069610.

Polynucleotides, such as guide RNA, sgRNA, and mRNA encoding an endonuclease, may be delivered to a cell or a subject by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 01/83692.

Formulation and Administration of Cells, e.g., Universal Donor Cells

Genetically modified cells, e.g., universal donor cells, as described herein may be formulated and administered to a subject by any manner known in the art.

The terms "administering," "introducing", "implanting", "engrafting" and "transplanting" are used interchangeably in the context of the placement of cells, e.g., progenitor cells, into a subject, by a method or route that results in at least partial localization of the introduced cells at a desired site. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment.

A genetically modified cell, e.g., universal donor cell, as described herein may be viable after administration to a subject for a period that is longer than that of an unmodified cell.

In some embodiments, a composition comprising cells as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

In some embodiments, a composition comprising cells may be administered to a subject, e.g., a human subject, who has, is suspected of having, or is at risk for a disease. In some embodiments, a composition may be administered to a subject who does not have, is not suspected of having or is not at risk for a disease. In some embodiments, a subject is a healthy human. In some embodiments, a subject e.g., a human subject, who has, is suspected of having, or is at risk for a genetically inheritable disease. In some embodiments, the subject is suffering or is at risk of developing symptoms indicative of a disease.

VI. Specific Compositions and Methods of the Disclosure

Accordingly, the present disclosure relates in particular to the following non-limiting compositions and methods.

In a first composition, Composition 1, the present disclosure a composition comprising cells that comprise (i) at least one genetic modification within or near at least one gene that encodes one or more MHC-I and MHC-II human leukocyte antigens or other components or transcriptional regulators of the MHC-I or MHC-II complex; (ii) at least one genetic modification that increases the expression of at least one polynucleotide that encodes a tolerogenic factor relative to an unmodified cell; and (iii) at least one genetic modification that increases or decreases the expression of at least one gene that encodes a survival factor relative to an unmodified cell.

In another composition, Composition 2, the present disclosure provides a composition comprising cells that comprise (i) at least one deletion and/or insertion of at least one base pair within or near at least one gene that encodes one or more MHC-I and MHC-II human leukocyte antigens or other components or transcriptional regulators of the MHC-I or MHC-II complex; and (ii) at least one insertion of a polynucleotide that encodes at least one tolerogenic factor at a site that partially overlaps, completely overlaps, or is contained within, the site of a genetic deletion of (i).

In another composition, Composition 3, the present disclosure provides a composition comprising cells that comprise at least one genetic modification that increases or decreases the expression of at least one gene that encodes a survival factor relative to an unmodified cell.

In another composition, Composition 4, the present disclosure provides a composition, as provided in Composition 1, wherein the genetic modification of (i) is a deletion.

In another composition, Composition 5, the present disclosure provides a composition, as provided in Composition 1, wherein the genetic modification of (ii) is an insertion of a polynucleotide that encodes a tolerogenic factor at a safe harbor locus or at a site that partially overlaps, completely overlaps, or is contained within, the site of a genetic modification of (i).

In another composition, Composition 6, the present disclosure provides a composition, as provided in Composition 1, wherein the genetic modification of (i) is a deletion of a gene that encodes one or more MHC-I and MHC-II human leukocyte antigens or other components or transcriptional regulators of the MHC-I or MHC-II complex; and the genetic modification of (ii) is an insertion of a polynucleotide that encodes at least one tolerogenic factor at a site that partially overlaps, completely overlaps, or is contained within, the site of a genetic modification of (i).

In another composition, Composition 7, the present disclosure provides a composition, as provided in any one of Compositions 1, 2, or 4 to 6, wherein the at least one gene that encodes one or more MHC-I and MHC-II human leukocyte antigens or other components or transcriptional regulators of the MHC-I or MHC-II complex is one or more of a MHC-I gene (e.g., HLA-A, HLA-B and HLA-C), a MHC-II gene (e.g., HLA-DP, HLA-DM, HLA-DOA, HLA-DOB, HLA-DQ, and HLA-DR), or a gene that encodes a transcriptional regulator of MHC-I or MHC-II or other component of the MHC-I complex (e.g., B2M, NLRC5, and CIITA).

In another composition, Composition 8, the present disclosure provides a composition, as provided in of any one of Compositions 1, 2, or 4 to 6, wherein the at least one gene that encodes one or more MHC-I and MHC-I human leukocyte antigens or other components or transcriptional regulators of the MHC-I or MHC-II complex is one or more of HLA-A, HLA-B, HLA-C, B2M, or CIITA.

In another composition, Composition 9, the present disclosure provides a composition, as provided in Composition 1 or 2, wherein (i) is a deletion within or near one or more of HLA-A, HLA-B, HLA-C, B2M, or CIITA.

In another composition, Composition 10, the present disclosure provides a composition, as provided in Composition 9, wherein (i) is a deletion within or near HLA-A, a deletion within or near HLA-B, a deletion within or near HLA-C, or a deletion within or near B2M.

In another composition, Composition 11, the present disclosure provides a composition, as provided in Composition 9, wherein (i) is a deletion within or near HLA-A, a deletion within or near HLA-B, a deletion within or near HLA-C, or a deletion within or near CIITA.

In another composition, Composition 12, the present disclosure provides a composition, as provided in any one of Compositions 1, 2, or 4 to 11, wherein the at least one polynucleotide that encodes a tolerogenic factor is one or more polynucleotides that encode one or more of HLA-E, HLA-G, CTLA-4, CD47, or PD-L1.

In another composition, Composition 13, the present disclosure provides a composition, as provided in Composition 12, wherein (i) is a deletion within or near B2M and (ii) is an insertion of a polynucleotide encoding PD-L1 at a site that partially overlaps, completely overlaps, or is contained within the deletion in (i).

In another composition, Composition 14, the present disclosure provides a composition, as provided in Composition 12, wherein (i) is a deletion within or near HLA-A, a deletion within or near HLA-B, or a deletion within or near HLA-C and (ii) is an insertion of a polynucleotide that encodes HLA-G at a site that partially overlaps, completely overlaps, or is contained within a deletion in (i) (e.g., the HLA-A deletion).

In another composition, Composition 15, the present disclosure provides a composition, as provided in Composition 12, wherein (i) is a deletion within or near HLA-A, a deletion within or near HLA-B, a deletion within or near HLA-C, or a deletion within or near CIITA and (ii) is an insertion of a polynucleotide that encodes HLA-G at a site that partially overlaps, completely overlaps, or is contained within the deletion within or near HLA-A and insertion of a polynucleotide that encodes CD47 at a site that partially overlaps, completely overlaps, or is contained within the deletion within or near CIITA.

In another composition, Composition 16, the present disclosure provides a composition, as provided in any one of Compositions 1 or 3 to 15, wherein the at least one gene that encodes a survival factor is one or more genes that encode one or more of ZNF143, TXNIP, FOXO1, JNK, or MANF.

In another composition, Composition 17, the present disclosure provides a composition, as provided in any one of Compositions 1 or 3 to 16, wherein the genetic modification that increases or decreases the expression of a gene that encodes a survival factor relative to an unmodified cell is an insertion of a polynucleotide that encodes MANF, e.g., at a safe harbor locus.

In another composition, Composition 18, the present disclosure provides a composition, as provided in any one of Compositions 1 or 3 to 16, wherein the genetic modification that increases or decreases the expression of a gene that encodes a survival factor relative to an unmodified cell is a deletion within or near a ZNF143, TXNIP, FOXO1, or JNK gene, which reduces or eliminates expression of the ZNF143, TXNIP, FOXO1, or JNK gene relative to an unmodified cell.

In another composition, Composition 19, the present disclosure provides a composition, as provided in any one of Compositions 1 to 18, wherein the cells further comprise an exogenous polynucleotide that is not integrated into the genomic DNA of the cells.

In another composition, Composition 20, the present disclosure provides a composition, as provided in Composition 19, wherein the exogenous polynucleotide encodes HLA-E, HLA-G, CTLA-4, CD47, MANF, and/or PD-L1.

In another composition, Composition 21, the present disclosure provides a composition, as provided in any one of Compositions 1 to 20, wherein the cells further comprise increased expression of one or more safety switch relative to an unmodified cell.

In another composition, Composition 22, the present disclosure provides a composition, as provided in Composition 21, wherein a safety switch is herpes simplex virus-1 thymidine kinase (HSV-tk) or inducible caspase-9.

In another composition, Composition 23, the present disclosure provides a composition, as provided in Composition 21 or 22, wherein increased expression of one or more safety switches results from a genetic insertion of a polynucleotide that encodes a safety switch protein, e.g., into a safe harbor locus.

In another composition, Composition 24, the present disclosure provides a composition, as provided in any one of Compositions 5, 17, or 23, wherein the safe harbor locus is selected from the group consisting of AAVS1 (PPP1 R12C), ALB, Angptl3, ApoC3, ASGR2, CCR5, FIX (F9), G6PC, Gys2, HGD, Lp(a), Pcsk9, Serpina1, TF, and TTR.

In another composition, Composition 25, the present disclosure provides a composition, as provided in any one of Compositions 1 to 24, wherein the cells further comprise an additional genetic modification that decreases the expression of any additional gene.

In another composition, Composition 26, the present disclosure provides a composition, as provided in any one of Compositions 1 to 25, wherein the genetic modification, genetic deletion, or genetic insertion is produced by delivering to the cells an endonuclease and a guide RNA (gRNA).

In another composition, Composition 27, the present disclosure provides a composition, as provided in Composition 26, wherein the endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

In another composition, Composition 28, the present disclosure provides a composition, as provided in Composition 27, wherein the endonuclease is a Cas9, optionally a *S. pyogenes* Cas9, or a variant thereof comprising a N-terminus SV40 NLS and a C-terminus SV40 NLS.

In another composition, Composition 29, the present disclosure provides a composition, as provided in Composition 26, wherein the weight ratio of said gRNA to said endonuclease is 1:1.

In another composition, Composition 30, the present disclosure provides a composition, as provided in any one of Compositions 2, 5, 6, 12 to 15, 17, 19, 20, or 23 wherein the polynucleotide comprises an exogenous promoter.

In another composition, Composition 31, the present disclosure provides a composition, as provided in Composition 30, wherein the exogenous promoter is a CMV, EF1a, PGK, CAG, UBC, or other constitutive, inducible, temporal-, tissue-, or cell type-specific promoter.

In another composition, Composition 32, the present disclosure provides a composition, as provided in Composition 31, wherein the exogenous promoter is a CAG promoter.

In another composition, Composition 33, the present disclosure provides a composition, as provided in any one of Compositions 1 to 32, wherein the cells are stem cells (e.g., human stem cells).

In another composition, Composition 34, the present disclosure provides a composition, as provided in any one of Compositions 1 to 33, wherein the cells are embryonic stem cells (ESCs), adult stem cells (ASCs), induced pluripotent stem cells (iPSCs), or hematopoietic stem and progenitor cells (HSPCs).

In another composition, Composition 35, the present disclosure provides a composition, as provided in any one of Compositions 1 to 32, wherein the cells are differentiated cells.

In another composition, Composition 36, the present disclosure provides a composition, as provided in any one of Composition 1 to 32 or 35, wherein the cells are somatic cells.

In a first method, Method 1, the present disclosure provides a method of generating modified cells, the method comprising: (i) introducing at least one genetic modification within or near at least one gene that encodes one or more MHC-I and MHC-II human leukocyte antigens or other components or transcriptional regulators of the MHC-I or MHC-II complex; (ii) introducing at least one genetic modification that increases the expression of at least one polynucleotide that encodes a tolerogenic factor in the cells; and (iii) introducing at least one genetic modification that increases or decreases the expression of at least one gene that encodes a survival factor in the universal donor cells.

In another method, Method 2, the present disclosure provides a method of generating universal donor cells, the method comprising: (i) introducing at least one deletion of at least one region of genomic DNA within or near at least one gene that encodes one or more MHC-I and MHC-II human leukocyte antigens or other components or transcriptional regulators of the MHC-I or MHC-II complex; and (ii) introducing at least one insertion of at least one polynucleotide that encodes a tolerogenic factor at a site that partially overlaps, completely overlaps, or is contained within, the site of a deletion of (i).

In another method, Method 3, the present disclosure provides a method of generating universal donor cells, the method comprising introducing at least one genetic modification that increases or decreases the expression of at least one gene that encodes a survival factor.

In another method, Method 4, the present disclosure provides a method as provided in Method 1, wherein the genetic modification of (i) is a deletion.

In another method, Method 5, the present disclosure provides a method as provided in Method 1, wherein the genetic modification of (ii) is an insertion of a polynucleotide that encodes a tolerogenic factor at a safe harbor locus or at a site that partially overlaps, completely overlaps, or is contained within, the site of a genetic modification of (i).

In another method, Method 6, the present disclosure provides a method as provided in Method 1, wherein the genetic modification of (i) is a deletion of a gene that encodes one or more MHC-I and MHC-II human leukocyte antigens or other components or transcriptional regulators of the MHC-I or MHC-II complex; and the genetic modification of (ii) is an insertion of a polynucleotide that encodes at least one tolerogenic factor at a site that partially overlaps, completely overlaps, or is contained within, the site of a genetic modification of (i).

In another method, Method 7, the present disclosure provides a method as provided in any one of Methods 1, 2, or 4 to 6, wherein the at least one gene that encodes one or more MHC-I and MHC-II human leukocyte antigens or other components or transcriptional regulators of the MHC-I or MHC-II complex is one or more of a MHC-I gene (e.g., HLA-A, HLA-B and HLA-C), a MHC-II gene (e.g., HLA-DP, HLA-DM, HLA-DOA, HLA-DOB, HLA-DQ, and HLA-DR), or a gene that encodes a transcriptional regulator of MHC-I or MHC-I (e.g., B2M, NLRC5, and CIITA).

In another method, Method 8, the present disclosure provides a method as provided in any one of Methods 1, 2, or 4 to 6, wherein the at least one gene that encodes one or more MHC-I and MHC-II human leukocyte antigens or other components or transcriptional regulators of the MHC-I or MHC-II complex is one or more of HLA-A, HLA-B, HLA-C, B2M, or CTA.

In another method, Method 9, the present disclosure provides a method as provided in Method 1 or 2, wherein (i) is a deletion within or near one or more of HLA-A, HLA-B, HLA-C, B2M, or CIITA.

In another method, Method 10, the present disclosure provides a method as provided in Method 9, wherein (i) is a deletion within or near HLA-A, a deletion within or near HLA-B, a deletion within or near HLA-C, and a deletion within or near B2M.

In another method, Method 11, the present disclosure provides a method as provided in Method 9, wherein (i) is a deletion within or near HLA-A, a deletion within or near HLA-B, a deletion within or near HLA-C, and a deletion within or near CIITA.

In another method, Method 12, the present disclosure provides a method as provided in any one of Methods 1, 2, or 4 to 11, wherein the at least one polynucleotide that encodes a tolerogenic factor is one or more polynucleotides that encode one or more of HLA-E, HLA-G, CTLA-4, CD47, or PD-L1.

In another method, Method 13, the present disclosure provides a method as provided in Method 12, wherein (i) is a deletion within or near B2M and (ii) is an insertion of a polynucleotide encoding PD-L1 at a site that partially overlaps, completely overlaps, or is contained within the deletion in (i).

In another method, Method 14, the present disclosure provides a method as provided in Method 12, wherein (i) is a deletion within or near HLA-A, a deletion within or near HLA-B, and a deletion within or near HLA-C and (ii) is an insertion of a polynucleotide that encodes HLA-G at a site that partially overlaps, completely overlaps, or is contained within a deletion in (i) (e.g., the HLA-A deletion).

In another method, Method 15, the present disclosure provides a method as provided in Method 12, wherein (i) is a deletion within or near HLA-A, a deletion within or near HLA-B, a deletion within or near HLA-C, and a deletion within or near CIITA and (ii) is an insertion of a polynucleotide that encodes HLA-G at a site that partially overlaps, completely overlaps, or is contained within the deletion within or near HLA-A and insertion of a polynucleotide that encodes CD47 at a site that partially overlaps, completely overlaps, or is contained within the deletion within or near CIITA.

In another method, Method 16, the present disclosure provides a method as provided in any one of Methods 1 or 3 to 15, wherein the at least one gene that encodes a survival factor is one or more genes that encode one or more of a ZNF143, TXNIP, FOXO1, JNK, or MANF.

In another method, Method 17, the present disclosure provides a method as provided in any one of Methods 1 or 3 to 16, wherein the genetic modification that increases or decreases the expression of a gene that encodes a survival factor is an insertion of a polynucleotide that encodes MANF, e.g., at a safe harbor locus.

In another method, Method 18, the present disclosure provides a method as provided in any one of Methods 1 or 3 to 16, wherein the genetic modification that increases or decreases the expression of a gene that encodes a survival factor is a deletion within or near a ZNF143, TXNIP, FOXO1, or JNK gene, which reduces or eliminates expression of the ZNF143, TXNIP, FOXO1, or JNK gene relative to an unmodified cell.

In another method, Method 19, the present disclosure provides a method as provided in any one of Methods 1 to 18, wherein the cells are stem cells (e.g., human stem cells).

In another method, Method 20, the present disclosure provides a method as provided in any one of Methods 1 to 19, wherein the cells are embryonic stem cells (ESCs), adult stem cells (ASCs), induced pluripotent stem cells (iPSCs), or hematopoietic stem and progenitor cells (HSPCs).

In another method, Method 21, the present disclosure provides a method as provided in any one of Methods 1 to 18, wherein the cells are differentiated cells.

In another method, Method 22, the present disclosure provides a method as provided in any one of Methods 1 to 18 or 21, wherein the cells are somatic cells.

In another method, Method 23, the present disclosure provides a method as provided in any one of Methods 1 to 22, wherein the method further comprises introducing an exogenous polynucleotide into the cells that does not become integrated into the genomic DNA of the cells.

In another method, Method 24, the present disclosure provides a method as provided in Method 23, wherein the exogenous polynucleotide encodes HLA-E, HLA-G, CTLA-4, CD47, MANF and/or PD-L1.

In another method, Method 25, the present disclosure provides a method as provided in any one of Methods 1 to 24, wherein the method further comprises increasing expression of one or more safety switches relative to an unmodified cell.

In another method, Method 26, the present disclosure provides a method as provided in Method 25, wherein a safety switch is herpes simplex virus-1 thymidine kinase (HSV-tk) or inducible caspase-9.

In another method, Method 27, the present disclosure provides a method as provided in Method 25 or 26, wherein increasing expression of one or more safety switches results from a genetic insertion of a polynucleotide that encodes a safety switch, e.g., into a safe harbor locus.

In another method, Method 28, the present disclosure provides a method as provided in any one of Methods 5, 17, or 27, wherein the safe harbor locus is selected from the group consisting of AAVS1 (PPP1 R12C), ALB, Angptl3, ApoC3, ASGR2, CCR5, FIX (F9), G6PC, Gys2, HGD, Lp(a), Pcsk9, Serpina1, TF, and TTR.

In another method, Method 29, the present disclosure provides a method as provided in any one of Methods 1 to 28, wherein the method further comprises introducing an additional genetic modification that decreases the expression of any additional gene.

In another method, Method 30, the present disclosure provides a method as provided in any one of Methods 1 to 29, wherein the genetic modification, deletion, or insertion is produced by delivering to the cells an endonuclease and at least one guide RNA (gRNA).

In another method, Method 31, the present disclosure provides a method as provided in Method 30, wherein the endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

In another method, Method 32, the present disclosure provides a method as provided in Method 31, wherein the endonuclease is a Cas9, optionally a *S. pyogenes* Cas9, or a variant thereof comprising an N-terminus SV40 NLS and a C-terminus SV40 NLS.

In another method, Method 33, the present disclosure provides a method as provided in Method 30, wherein the weight ratio of said gRNA(s) to said endonuclease is 1:1.

In another method, Method 34, the present disclosure provides a method as provided in any one of Methods 2, 5, 6, 12 to 15, 17, 23, 25, or 27, wherein the polynucleotide comprises an exogenous promoter.

In another method, Method 35, the present disclosure provides a method as provided in Method 34, wherein the exogenous promoter is a CMV, EFla, PGK, CAG, UBC, or other constitutive, inducible, temporal-, tissue-, or cell type-specific promoter.

In another method, Method 36, the present disclosure provides a method as provided in Method 35, wherein the exogenous promoter is a CAG promoter.

In another method, Method 37, the present disclosure provides a method comprising administering to a subject a composition of cells as provided in any one of Compositions 1 to 36 or a composition comprising a plurality of cells generated by any one of Methods 1 to 36.

In another method, Method 38, the present disclosure provides a method comprising (i) obtaining a composition of cells as provided in any one of Compositions 1 to 34; (ii) differentiating the cells into lineage-restricted cells or fully differentiated cells; and (iii) administering the lineage-restricted cells or fully differentiated cells to a subject in need thereof.

In another method, Method 39, the present disclosure provides a method as provided in Method 37 or 38, wherein the subject is a human who has, is suspected of having, or is at risk for a disease.

In another method, Method 40, the present disclosure provides a method as provided in Method 39, wherein the disease is a genetically inheritable disease.

In another method, Method 41, the present disclosure provides a method as provided in Method 39 or 40, wherein the cells further comprise a genetic modification that decreases the expression of a gene or protein that is associated with the disease.

In another method, Method 42, the present disclosure provides a method as provided in any one of Methods 39 to 41, wherein the genetic modification is capable of treating the disease or symptoms of the disease.

In another method, Method 43, the present disclosure provides a method as provided in any one of Methods 37 to 42, wherein the cells are obtained from a source other than the subject.

In another method, Method 44, the present disclosure provides a method of generating a universal donor cell, the method comprising genetically modifying a cell by (i) introducing a deletion and/or insertion of at least one base pair in the genome of the cell at a site within or near at least one gene that encodes one or more of a MHC-I or MHC-II human leukocyte antigens or a component or a transcriptional regulator of a MHC-I or MHC-II complex; and (ii) introducing in the genome of the cell an insertion of at least one polynucleotide that encodes a tolerogenic factor, at a site that partially overlaps, completely overlaps, or is contained within, the site of (i), thereby generating the universal donor cell.

In another method, Method 45, the present disclosure provides a method of generating a universal donor cell, the method comprising genetically modifying a cell by (i) introducing a deletion and/or insertion of at least one base pair in the genome of the cell at a site within or near at least one gene that encodes one or more of a MHC-I or MHC-11 human leukocyte antigens or a component or a transcriptional regulator of a MHC-I or MHC-II complex; and (ii) introducing in the genome of the cell an insertion of at least one polynucleotide that encodes a tolerogenic factor into a safe harbor locus, thereby generating the universal donor cell.

In another method, Method 46, the present disclosure provides a method as provided in Methods 44 or 45, wherein the universal donor cell has increased immune evasion and/or cell survival compared to an unmodified cell.

In another method, Method 47, the present disclosure provides a method as provided in any one of Methods 44 to 46, wherein the at least one gene that encodes one or more MHC-I or MHC-I human leukocyte antigens or the component or the transcriptional regulator of the MHC-I or MHC-II complex is a MHC-I gene chosen from HLA-A, HLA-B, or HLA-C, a MHC-II gene chosen from HLA-DP, HLA-DM, HLA-DOA, HLA-DOB, HLA-DQ, or HLA-DR, or a gene chosen from B2M, NLRC5, CIITA, RFX5, RFXAP, or RFXANK.

In another method, Method 48, the present disclosure provides a method as provided in any one of Methods 44 to 47, wherein the at least one polynucleotide that encodes a tolerogenic factor is one or more polynucleotides that encode one or more of PD-L1, HLA-E, HLA-G, CTLA-4, or CD47.

In another method, Method 49, the present disclosure provides a method as provided in any one of Methods 44 to 48, wherein the at least one polynucleotide that encodes a tolerogenic factor is operably linked to an exogenous promoter.

In another method, Method 50, the present disclosure provides a method as provided in Method 49, wherein the exogenous promoter is a constitutive, inducible, temporal-, tissue-, or cell type-specific promoter, the constitutive promoter being a CMV, EFla, PGK, CAG, or UBC promoter.

In another method, Method 51, the present disclosure provides a method as provided in any one of Methods 44 to 50, wherein the deletion and/or insertion of (i) is within or near B2M, and the insertion of (ii) is a polynucleotide encoding PD-L1 or HLA-E.

In another method, Method 52, the present disclosure provides a method as provided in any one of Methods 44 to 51, wherein the method further comprises introducing at least one genetic modification that increases or decreases expression of at least a survival factor relative to an unmodified cell.

In another method, Method 53, the present disclosure provides a method as provided in Method 52, wherein the at least one genetic modification that increases or decreases expression of at least a survival factor is an insertion of a polynucleotide that encodes MANF, which increases expression of MANF relative to the unmodified cell; or a deletion and/or insertion of at least one base pair within or near a gene that encodes ZNF143, TXNIP, FOXO1, or JNK, which reduces or eliminates expression of ZNF143, TXNIP, FOXO1, or JNK relative to the unmodified cell.

In another method, Method 54, the present disclosure provides a method as provided in Method 53, wherein the polynucleotide that encodes MANF is inserted into a safe harbor locus or into a gene belonging to a MHC-I, MHC-II, or transcriptional regulator of MHC-I or MHC-II.

In another method, Method 55, the present disclosure provides a method as provided in any one of Methods 44 to 54, wherein the genetically modifying comprises delivering at least one RNA-guided endonuclease system to the cell.

In another method, Method 56, the present disclosure provides a method as provided in Method 55, wherein the at least one RNA-guided endonuclease system is a CRISPR system comprising a CRISPR nuclease and a guide RNA.

In another method, Method 57, the present disclosure provides a method as provided in Method 56, wherein the CRISPR nuclease is Cas9, Cpf1, a homolog thereof, a modified version thereof, a codon-optimized version thereof, or any combination thereof.

In another method, Method 58, the present disclosure provides a method as provided in Method 56 or 57, wherein the CRISPR nuclease is a *S. pyogenes* Cas9.

In another method, Method 59, the present disclosure provides a method as provided in any one of Methods 56 to 58, wherein the CRISPR nuclease comprises an N-terminus nuclear localization signal (NLS) and/or a C-terminus NLS.

In another method, Method 60, the present disclosure provides a method as provided in any one of Methods 56 to 59, wherein the CRISPR nuclease and the guide RNA are present at a weight ratio of 1:1.

In another method, Method 61, the present disclosure provides a method as provided in any one of Methods 44 or 46 to 60, wherein the deletion and/or insertion of (i) is within or near a B2M gene locus, and the insertion of (ii) is a polynucleotide encoding PD-L1.

In another method, Method 62, the present disclosure provides a method as provided in Method 61, wherein the guide RNA used for (i) and (ii) comprises a nucleotide sequence comprising at least one of SEQ ID NOS: 1-3 or 35-44.

In another method, Method 63, the present disclosure provides a method as provided in Method 61 or 62, wherein the polynucleotide encoding PD-L1 is flanked by (a) a nucleotide sequence having sequence homology with a region located left of the site in (i) and (b) a nucleotide sequence having sequence homology with a region located right of the site in (i).

In another method, Method 64, the present disclosure provides a method as provided in Method 63, wherein the polynucleotide encoding PD-L1 is inserted into the B2M gene locus within 50 base pairs of the site in (i).

In another method, Method 65, the present disclosure provides a method as provided in Method 63 or 64, wherein (a) consists essentially of a nucleotide sequence of SEQ ID NO: 13, and (b) consists essentially of a nucleotide sequence of SEQ ID NO: 19.

In another method, Method 66, the present disclosure provides a method as provided in any one of Methods 61 to 65, wherein the polynucleotide encoding PD-L1 is operably linked to an exogenous promoter, optionally wherein the exogenous promoter is a CAG promoter.

In another method, Method 67, the present disclosure provides a method as provided in any one of Methods 44 to 66, wherein the cell is a mammalian cell, optionally wherein the cell is a human cell.

In another method, Method 68, the present disclosure provides a method as provided in any one of Methods 44 to 67, wherein the cell is a stem cell.

In another method, Method 69, the present disclosure provides a method as provided in any one of Methods 44 to 68, wherein the cell is a pluripotent stem cell (PSC), an embryonic stem cell (ESC), an adult stem cell (ASC), an induced pluripotent stem cell (iPSC), or a hematopoietic stem and progenitor cell (HSPC).

In another method, Method 70, the present disclosure provides a method as provided in any one of Methods 44 to 69, wherein the cell is a differentiated cell or a somatic cell.

In another method, Method 71, the present disclosure provides a method as provided in any one of Methods 44 to 69, wherein the universal donor cell is capable of being differentiated into lineage-restricted progenitor cells or fully differentiated somatic cells.

In another method, Method 72, the present disclosure provides a method as provided in Method 71, wherein the lineage-restricted progenitor cells are pancreatic endoderm progenitors, pancreatic endocrine progenitors, mesenchymal progenitor cells, muscle progenitor cells, blast cells, or neural progenitor cells.

In another method, Method 73, the present disclosure provides a method as provided in Method 71, wherein the fully differentiated somatic cells are endocrine secretory cells such as pancreatic beta cells, epithelial cells, endodermal cells, macrophages, hepatocytes, adipocytes, kidney cells, blood cells, or immune system cells.

In another composition, Composition 37, the present disclosure provides a composition comprising a plurality of universal donor cells generated by a method as provided in any one of Methods 44 to 73.

In another composition, Composition 38, the present disclosure provides a composition as provided in Composition 37, wherein the plurality of universal donor cells can be maintained for a time and under conditions sufficient for the cells to undergo differentiation.

In another composition, Composition 39, the present disclosure provides a composition comprising cells that comprise (i) at least one deletion within or near at least one gene that encodes one or more MHC-1 and MHC-II human leukocyte antigens or a components or a transcriptional regulator of a MHC-I or MHC-II complex; and (ii) at least one insertion of a polynucleotide that encodes at least one tolerogenic factor at a site that partially overlaps, completely overlaps, or is contained within, the site of a genetic deletion of (i).

In another method, Method 74, the present disclosure provides a method comprising administering to a subject the plurality of universal donor cells of Composition 37 or 38.

In another method, Method 75, the present disclosure provides a method for treating of a subject in need thereof, the method comprising (i) obtaining or having obtained the plurality of universal donor cells of Composition 37 or 38 following differentiation into lineage-restricted progenitor cells or fully differentiated somatic cells; and (ii) administering the lineage-restricted progenitor cells or fully differentiated somatic cells to the subject.

In another method, Method 76, the present disclosure provides a method of obtaining cells for administration to a subject in need thereof, the method comprising (i) obtaining or having obtained the universal donor cells of Composition 37 or 38; and (ii) maintaining the universal donor cells for a time and under conditions sufficient for the cells to differentiate into lineage-restricted progenitor cells or fully differentiated somatic cells.

In another method, Method 77, the present disclosure provides a method as provided in Method 75 or 76, wherein the lineage-restricted progenitor cells are pancreatic endoderm progenitors, pancreatic endocrine progenitors, mesenchymal progenitor cells, muscle progenitor cells, blast cells, or neural progenitor cells.

In another method, Method 78, the present disclosure provides a method as provided in Method 75 or 76, wherein the fully differentiated somatic cells are endocrine secretory cells such as pancreatic beta cells, epithelial cells, endodermal cells, macrophages, hepatocytes, adipocytes, kidney cells, blood cells, or immune system cells.

In another method, Method 79, the present disclosure provides a method as provided in any one of Methods 74 to 78, wherein the subject is a human who has, is suspected of having, or is at risk for a disease.

In another method, Method 80, the present disclosure provides a method as provided in Method 79, wherein the disease is a genetically inheritable disease.

In another method, Method 81, the present disclosure provides a method for generating a universal donor cell, the method comprising delivering to a pluripotent stem cell (PSC) (a) an RNA-guided nuclease; (b) a guide RNA (gRNA) targeting a target site in a beta-2-microglobulin (B2M) gene locus; and (c) a vector comprising a nucleic acid, the nucleic acid comprising (i) a nucleotide sequence homologous with a region located left of the target site in the B2M gene locus, (ii) a nucleotide sequence encoding a tolerogenic factor, and (iii) a nucleotide sequence homologous with a region located right of the target site in the B2M gene locus, wherein the B2M gene locus is cleaved at the target site and the nucleic acid is inserted into the B2M gene locus within 50 base pairs of the target site, thereby generating a universal donor cell, wherein the universal donor cell has increased immune evasion and/or cell survival compared to a PSC that does not comprise the nucleic acid inserted into the B2M gene locus.

In another method, Method 82, the present disclosure provides a method as provided in Method 81, wherein the gRNA comprises a nucleotide sequence chosen from SEQ ID NO: 1, SEQ ID NO: 2, or SEQ ID NO: 3.

In another method, Method 83, the present disclosure provides a method as provided in Method 81 or 82, wherein (i) consists essentially of a nucleotide sequence of SEQ ID NO: 13, and (iii) consists essentially of a nucleotide sequence of SEQ ID NO: 19.

In another method, Method 84, the present disclosure provides a method as provided in any one of Methods 81 to 83, wherein the tolerogenic factor is programmed death ligand 1 (PD-L1) or human leukocyte antigen E (HLA-E).

In another method, Method 85, the present disclosure provides a method as provided in any one of Methods 81 to 84, wherein the nucleotide sequence encoding the tolerogenic factor is operably linked to an exogenous promoter.

In another method, Method 86, the present disclosure provides a method as provided in Method 85, wherein the exogenous promoter is constitutive, cell type-specific, tissue-type specific, or temporally regulated.

In another method, Method 87, the present disclosure provides a method as provided in Method 85 or 86, wherein the exogenous promoter is a CAG promoter.

In another method, Method 88, the present disclosure provides a method as provided in any one of Methods 81 to 87, wherein the vector is a plasmid vector.

In another method, Method 89, the present disclosure provides a method as provided in Method 88, wherein the plasmid vector comprises a nucleotide sequence of SEQ ID NO: 33 or SEQ ID NO: 34.

In another method, Method 90, the present disclosure provides a method as provided in any one of Methods 81 to 89, wherein the RNA-guided nuclease is a Cas9 nuclease.

In another method, Method 91, the present disclosure provides a method as provided in Method 90, wherein the Cas9 nuclease is linked to at least one nuclear localization signal (NLS).

In another method, Method 92, the present disclosure provides a method as provided in Method 90 or 91, wherein the Cas9 nuclease is a *S. pyogenes* Cas9.

In another method, Method 93, the present disclosure provides a method as provided in any one of Methods 81 to 92, wherein the PSC is an embryonic stem cell (ESC), an adult stem cell (ASC), an induced pluripotent stem cell (iPSC), or a hematopoietic stem and progenitor cell (HSPC).

In another method, Method 94, the present disclosure provides a method as provided in any one of Methods 81 to 93, wherein the PSC is a human PSC.

In another method, Method 95, the present disclosure provides a method for generating a universal donor cell, the method comprising delivering to a pluripotent stem cell (PSC) (a) an RNA-guided nuclease; (b) a guide RNA (gRNA) targeting a target site in a beta-2-microglobulin (B2M) gene locus, wherein the gRNA comprises a nucleotide sequence of SEQ ID NO: 2; and (c) a vector comprising a nucleic acid, the nucleic acid comprising (i) a nucleotide sequence homologous with a region located left of the target site in the B2M gene locus that consists essentially of SEQ ID NO: 13, (ii) a nucleotide sequence encoding a tolerogenic factor, and (iii) a nucleotide sequence homologous with a region located right of the target site in the B2M gene locus that consists essentially of SEQ ID NO:19, wherein the B2M gene locus is cleaved at the target site and the nucleic acid is inserted into the B2M gene locus within 50 base pairs of the target site, thereby generating the universal donor cell, wherein the universal donor cell has increased immune evasion and/or cell survival compared to a PSC that does not comprise the nucleic acid inserted into the B2M gene locus.

In another method, Method 96, the present disclosure provides a method as provided in Method 95, wherein the tolerogenic factor is programmed death ligand 1 (PD-L1) or human leukocyte antigen E (HLA-E).

In another method, Method 97, the present disclosure provides a method as provided in Method 95 or 96, wherein the nucleotide sequence encoding the tolerogenic factor is operably linked to an exogenous promoter.

In another method, Method 98, the present disclosure provides a method as provided in Method 97, wherein the exogenous promoter is constitutive, cell type-specific, tissue-type specific, or temporally regulated.

In another method, Method 99, the present disclosure provides a method as provided in Method 97 or 98, wherein the exogenous promoter is a CAG promoter.

In another method, Method 100, the present disclosure provides a method as provided in any one of Methods 95 to 99, wherein the vector is a plasmid vector.

In another method, Method 101, the present disclosure provides a method as provided in Method 100, wherein the plasmid vector comprises a nucleotide sequence of SEQ ID NO: 33 or SEQ ID NO: 34.

In another method, Method 102, the present disclosure provides a method as provided in any one of Methods 95 to 101, wherein the RNA-guided nuclease is a Cas9 nuclease.

In another method, Method 103, the present disclosure provides a method as provided in Method 102, wherein the Cas9 nuclease is linked to at least one nuclear localization signal (NLS).

In another method, Method 104, the present disclosure provides a method as provided in Method 102 or 103, wherein the Cas9 nuclease is a *S. pyogenes* Cas9.

In another method, Method 105, the present disclosure provides a method as provided in any one of Methods 95 to 104, wherein the PSC is an embryonic stem cell (ESC), an adult stem cell (ASC), an induced pluripotent stem cell (iPSC), or a hematopoietic stem and progenitor cell (HSPC).

In another method, Method 106, the present disclosure provides a method as provided in any one of Methods 95 to 105, wherein the PSC is a human PSC.

VII. Examples

Figure 1C:
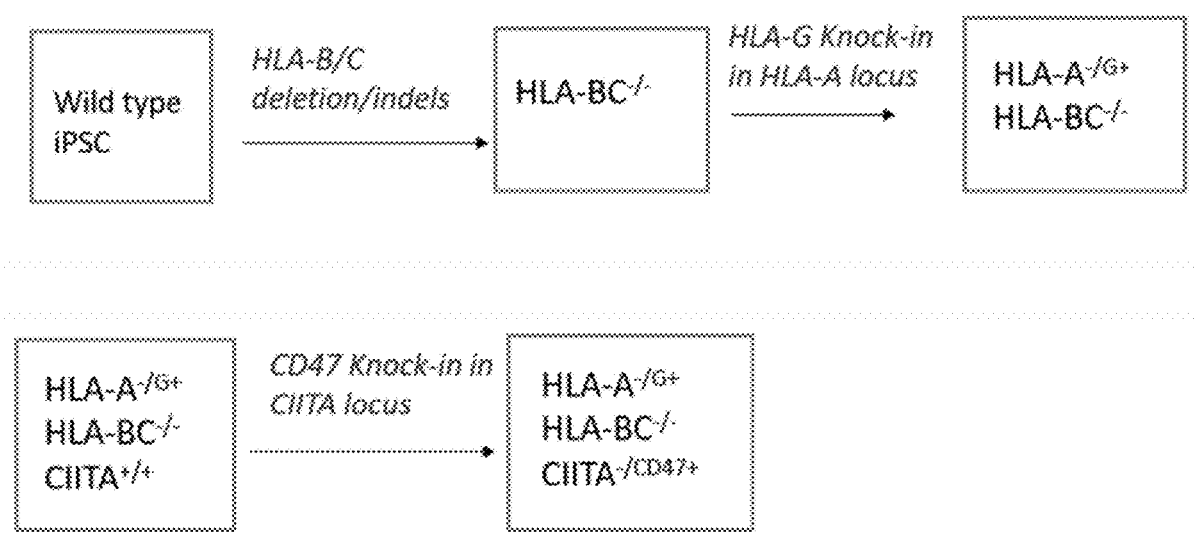

The examples below describe generation and characterization of universal donor cells according to the present disclosure. Table 1 lists tolerogenic factors and Table 2 lists survival factors that may be genetically modified in said cells. FIGS. 1A-1C depict various gene editing strategies that can be employed for immune evasion.

TABLE 1

Tolerogenic factors that may be genetically modified

| Factor | Knock out (KO) | Knock in (KI) |
|---|---|---|
| HLA-E | | + |
| HLA-G | | + |
| CTLA-4 | | + |
| CD47 | | + |
| PD-L1 | | + |
| B2M | − | |
| HLA-ABC | − | |
| CIITA | − | |

TABLE 2

Survival factors that may be genetically modified

| Factor | Knock out (KO) | Knock in (KI) |
|---|---|---|
| ZNF143 | − | |
| TXNIP | − | |
| FOXO | − | |
| JNK | − | |
| MANF | | + |

Example 1: Generation of B2M Knock-Out IPSCs

Guide RNA (gRNA) Selection for B2M.

To identify a large spectrum of gRNAs capable of editing the B2M DNA target region, an in vitro transcribed (IVT) gRNA screen was conducted. B2M targeting gRNAs were designed to target exon 1 of the B2M gene. B2M genomic sequence was submitted for analysis using gRNA design software. The resulting list of gRNAs was narrowed to a list of about 200 gRNAs based on uniqueness of sequence (only gRNAs without a perfect match somewhere else in the genome were screened) and minimal predicted off targets. This set of gRNAs was in vitro transcribed and transfected using MessengerMax into HEK293T cells that constitutively express Cas9. Cells were harvested 48 hours post transfection, the genomic DNA was isolated, and cutting efficiency was evaluated using TIDE analysis. Guide RNAs with high indels and low predicted off target effects were selected for further analysis. Table 3 presents the target sequences of selected B2M gRNAs.

TABLE 3

Selected B2M gRNA Target Sequences

| Name | Target Sequence (5'-3') | SEQ ID NO: | PAM |
|---|---|---|---|
| B2M-1 gRNA (Exon 1_T12) | GCTACTCTCTCTTTCTGGCC | 1 | TGG |
| B2M-2 gRNA (Exon 1_T2) | GGCCGAGATGTCTCGCTCCG | 2 | TGG |
| B2M-3 gRNA (Exon 1_T8) | CGCGAGCACAGCTAAGGCCA | 3 | CGG |
| Exon 1_T1 | TATAAGTGGAGGCGTCGCGC | 35 | TGG |
| Exon 1_T3 | GAGTAGCGCGAGCACAGCTA | 36 | AGG |
| Exon 1_T4 | ACTGGACGCGTCGCGCTGGC | 37 | GGG |
| Exon 1_T5 | AAGTGGAGGCGTCGCGCTGG | 38 | CGG |
| Exon 1_T6 | GGCCACGGAGCGAGACATCT | 39 | CGG |
| Exon 1_T7 | GCCCGAATGCTGTCAGCTTC | 40 | AGG |
| Exon 1_T9 | CTCGCGCTACTCTCTCTTTC | 41 | TGG |
| Exon 1_T10 | TCCTGAAGCTGACAGCATTC | 42 | GGG |
| Exon 1_T11 | TTCCTGAAGCTGACAGCATT | 43 | CGG |
| Exon 1_T13 | ACTCTCTCTTTCTGGCCTGG | 44 | AGG |

Screening of B2M gRNAs in IPSCs.

Three gRNAs (B2M-1, B2M-2, and B2M-3) were used to edit iPSCs. The location of the target sequence of each of these gRNAs is diagrammed in FIG. 2. IPSCs (TC-1133 cell line, RUDCR, N.J.) cells were nucleofected using the Lonza 4D nucleofector and the P3 primary cell kit (Lonza, cat #V4XP-3024) with an RNP mixture of Cas9 (Aldevron, cat #9212-5MG) and gRNA (Synthego) at a molar ratio of 3:1 (gRNA:Cas9) with final concentrations of 125 pmol Cas9 and 375 pmol gRNA. Cells were dissociated using Accutase (Stempro, cat #A1110501), then resuspended in DMEM/F12 media (Gibco, cat #11320033), counted using a Cellometer (Nexcellon) and centrifuged. Cells were resuspended in P3 buffer with supplement 1 (4.5:1 ratio) at a concentration of $2 \times 10^3$ cells/µL. A total of $2 \times 10^5$ cells were combined with RNP complex, transferred to a nucleofection cuvette (Lonza kit) and nucleofected using program CA-137. For each cuvette 250 µL of StemFlex media (Gibco, cat #A3349401) with CloneR (Stem Cell Technologies, cat #05888)(1:10 ratio) was used to resuspend nucleofected cells. This cell suspension was split into two wells of a Vitronectin (Gibco, cat #A14700) coated 24-well plate with an additional 250 µL of StemFlex with CloneR. Cells were recovered in a hypoxic incubator (37° C., 4% 02, 8% $CO_2$) for 48 hours. After 48 hours, genomic DNA was harvested from one well of each technical replicate using a gDNA isolation kit (Qiagen, cat #69506)

Figure 2:
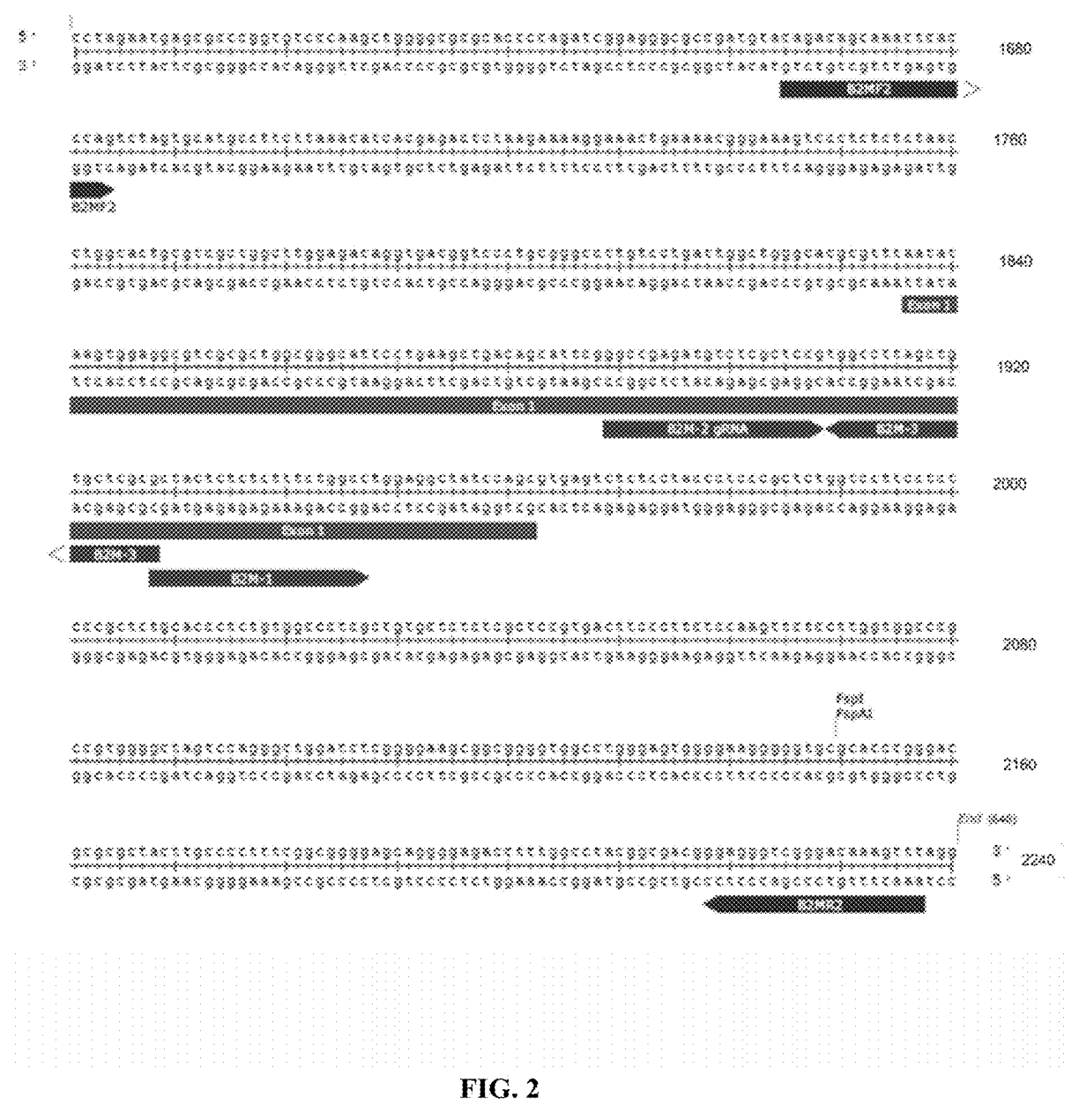

The isolated gDNA was subjected to PCR to determine indel frequency. PCR for relevant regions was performed using Platinum Taq Supermix (Invitrogen, cat #125320176 and Cat #11495017) with B2M primers. The primer sequences are provided in Table 4 and the locations of B2M primers relative to the gRNA target sites are shown in FIG. 2. The cycling conditions are provided in Table 5.

TABLE 4

B2M TIDE Primers

| Name | Type | Sequence (5'-3') | SEQ ID NO: |
|---|---|---|---|
| B2MF2 | forward | CAGACAGCAAACTCACCCAG | 4 |
| B2MR2 | reverse | AAACTTTGTCCCGACCCTCC | 5 |

TABLE 5

B2M PCR Cycling Parameters

| Step | Temperature | Time | Cycles |
|---|---|---|---|
| Denaturation | 94° C. | 2 min | 1 |
| Denaturation | 94° C. | 15 sec | 38 |
| Annealing | 55° C.° C. | 30 sec | |
| Extension | 68° C. | 45 sec | |
| Elongation | 68° C. | 5 min | 1 |
| Hold | 4 | hold | |

Figure 3A:
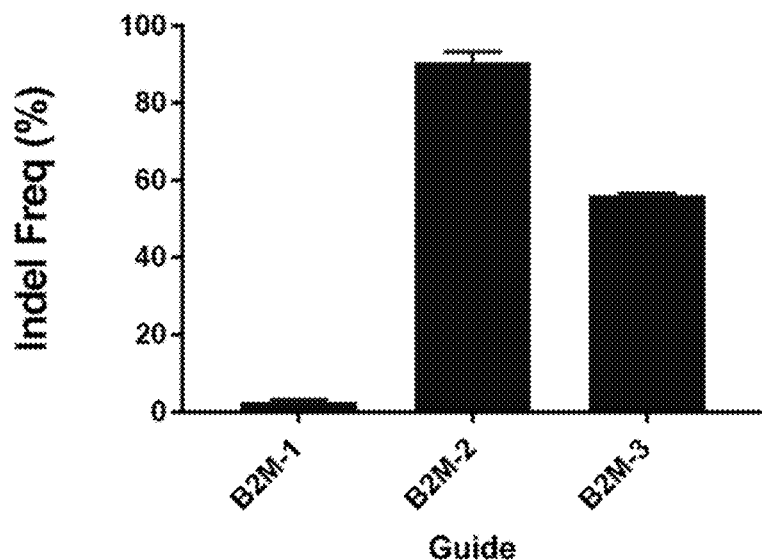
FIGS. 3A-3C show results from screening of B2M gRNAs in a TC-1133 iPSC cell line.
Figure 3B:
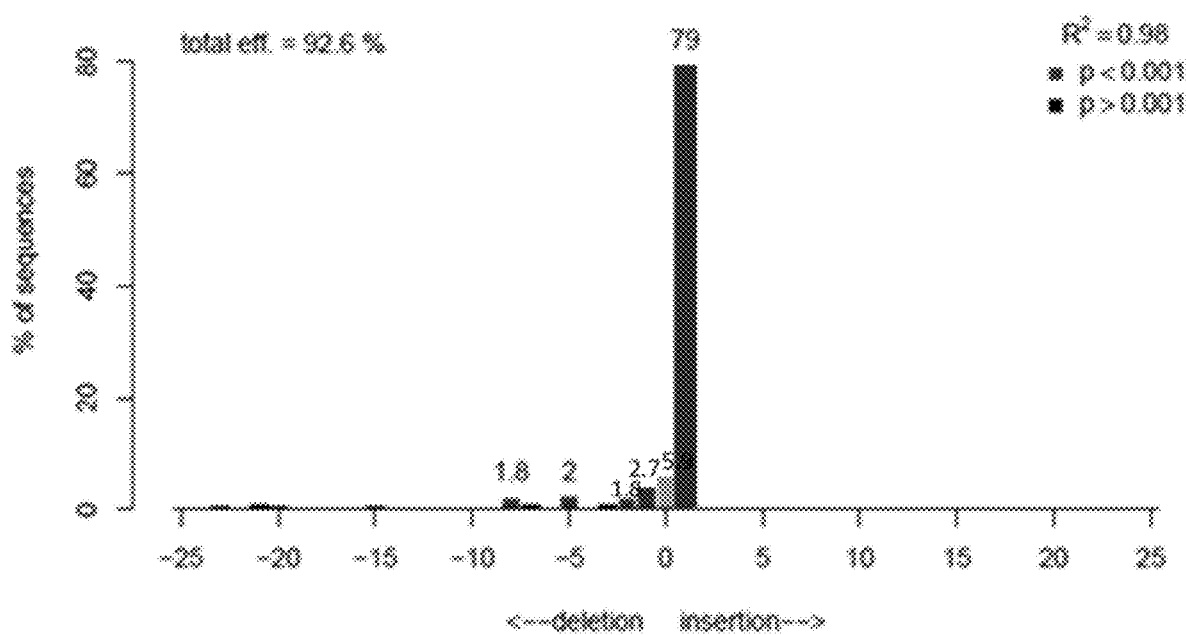
Figure 3C:
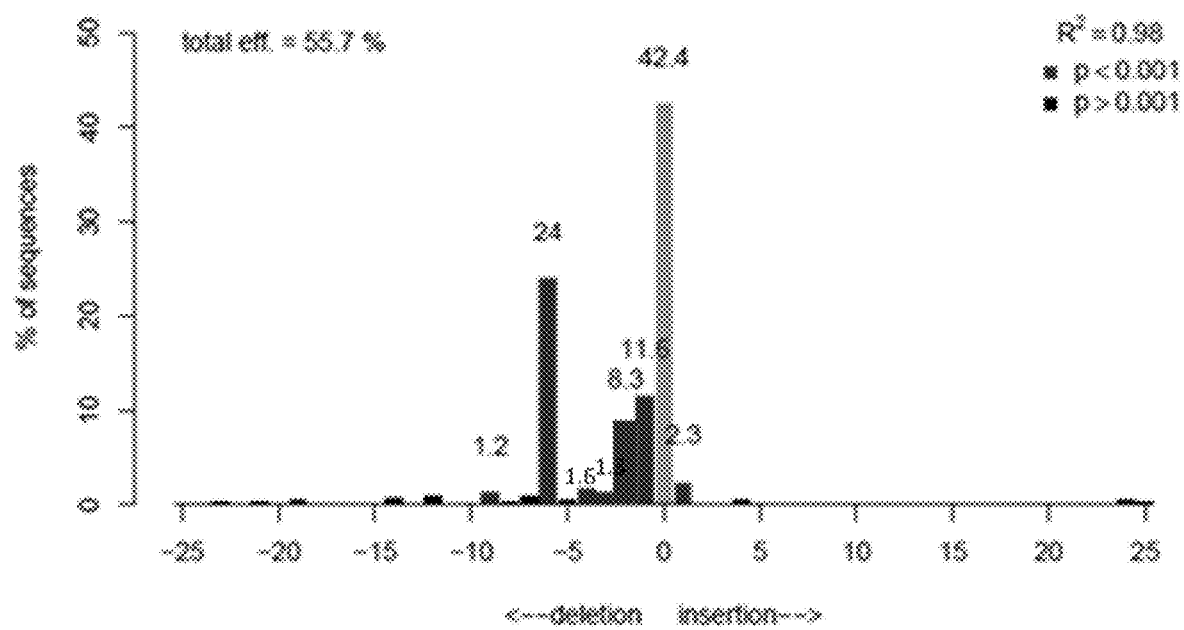

The resulting amplicons were submitted for PCR cleanup and Sanger sequencing. Sanger sequencing results were input into Tsunami along with guide sequence. Indel percentages and identities were calculated by the software (FIG. 3A). B2M-1, B2M-2, and B32M-3 gRNAs had indel frequencies of 2.5%±1.1%, 87.6%±14.1%, and 63.9%±0.9%, respectively (n=2). FIGS. 3B and 3C presents distributions of indel outcomes for the B2M-2 (FIG. 3B) and B2M-3 gRNAs (FIG. 3Q).

The cells in the duplicate well were maintained until confluent and then passaged to sequentially larger vessels. The bulk population was transitioned to Advanced 20/10/10 media (See Table 6) and Laminin-521 (Stem Cell Technologies, cat #77004) for maintenance.

TABLE 6

Advanced 20/10/10 Media Formulation

| Reagent | Amount | Working concentration | Reagent information |
|---|---|---|---|
| DMEM/F12 No HEPES | 955 mL | Base | Gibco (11330032) |
| Normocin | 2 mL | | Invivogen (ANTNR1) |
| Non-Essential Amino Acids, 100x | 10 mL | 1x | Gibco (11140076) |
| Chemically Defined Lipids, 100x | 2 mL | 0.2x | Gibco (11905031) |
| 20% HSA (FAF) | 5 mL | 0.1% | Sigma (A1887) |
| 7.5% Sodium bicarbonate | 7 mL | 0.0525% | Gibco (25080094) |
| Human insulin, 4 mg/mL | 5 mL | 20 µg/µL | Invitrogen (12585014) |
| Sodium Chloride, 250 mg/mL | 2 mL | 0.5 mg/mL | Sigma |
| Ascorbic Acid, 200 mM | 1 mL | 200 µM | Sigma |
| Holo-Transferrin, 10 mg/mL | 1 mL | 10 µg/mL | Sigma |
| Sodium selenite, 140 µg/mL | 100 µL | 14 ng/mL | Sigma |
| To make complete Advanced 20/10/10 (1 L volume) add the following at time of first use | | | |
| FGF basic, 100 µg/mL | 200 µL | 20 ng/mL | Peprotech |
| Activin A, 100 µg/ML | 100 µL | 10 ng/mL | Peprotech |
| Heregulin, 100 µg/mL | 100 µL | 10 ng/mL | Peprotech |

B2M KO IPS Clone Generation and Characterization.

Figure 4A:
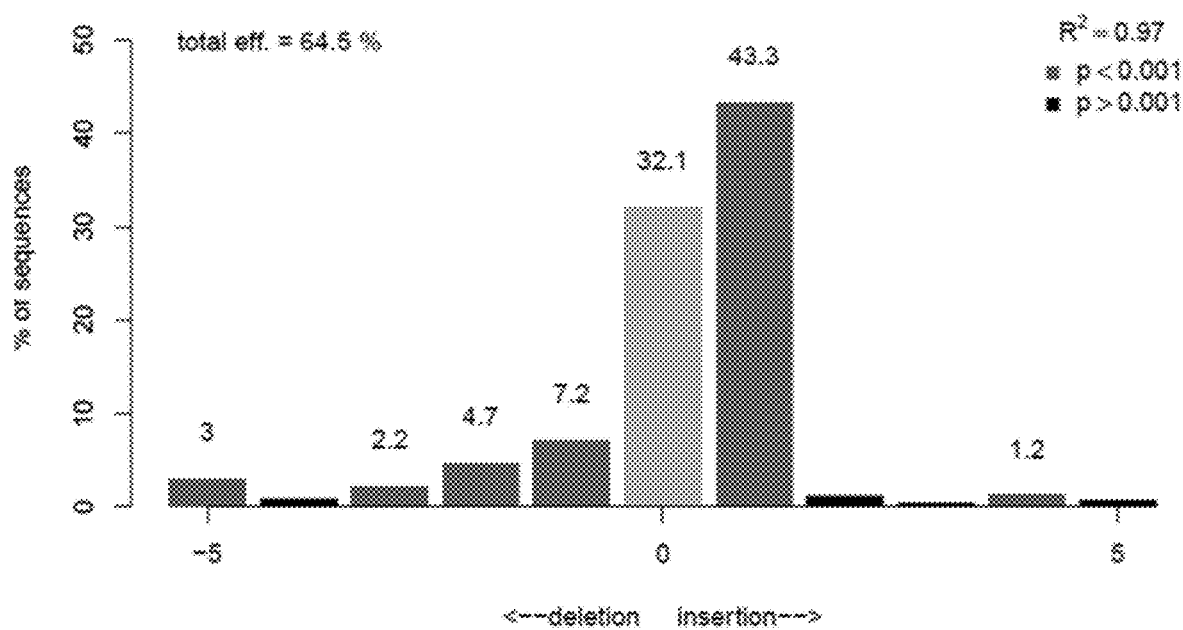
FIGS. 4A-4B show results of B2M knock-outs (KO) in iPSCs using B2M-2 gRNA.

Sequence-verified bulk-edited populations (FIG. 4A) were single cell sorted using a FACS-ARIA (BD Bioscience) into Vitronectin coated 96-well plates and recovered in StemFlex with CloneR. Briefly, cells were dissociated from maintenance flasks using Accutase and resuspended in StemFlex with CloneR. Cells were then counted using Cellometer and diluted to $1 \times 10^5$/mL. 2 mL of this was filtered through a cell strainer (Falcon, #352235) into a FACS tube, provided to the operator and single cells were sorted into individual wells. Plated single cells were grown in a hypoxic incubator (37° C., 8% $CO_2$, 4%02) with every other day media changes until colonies were large enough to be re-seeded as single cells. When confluent, samples were split for maintenance and gDNA extraction (see above). Clone identity was confirmed via PCR and Sanger sequencing (see below for details). Table 7 presents the sequences of select clones around the cut site (sequences deleted and/or inserted are shown in bold).

TABLE 7

Sequence Analysis of B2M KO Clones

| Clone | Sequence (5'-3') | | | SEQ ID NO: |
|---|---|---|---|---|
| WT | CT XCGC Z = $N_{16}$ | T | CCGTGGZGCTA, X = $N_{30}$, | 27 |
| A9 | CT XCGCGCTACTTA- Z = $N_{16}$ | -----GZGCTA, X = $N_{30}$, | | 28 |
| A11 | CT XCGC Z = $N_{16}$ | TTCCGTGGZGCTA, X = $N_{30}$, | | 29 |
| B10 | CTAA---- Z = $N_{16}$ | - ----GGZGCTA, X = $N_{30}$, | | 30 |
| B12 | CT XCGC Z = $N_{16}$ | TTCCGTGGZGCTA, X = $N_{30}$, | | 29 |
| C5 | CT XCGC Z = $N_{16}$ | - -------GCTA, X = $N_{30}$, | | 31 |
| C9 | CT XCGC Z = $N_{16}$ | - CCGTGGZGCTA, X = $N_{30}$, | | 32 |
| C11 | CT XCGC Z = $N_{16}$ | TTCCGTGGZGCTA, X = $N_{30}$, | | 29 |
| C12 | CT XCGC Z = $N_{16}$ | TTCCGTGGZGCTA, X = $N_{30}$, | | 29 |

Figures 4B, 5:
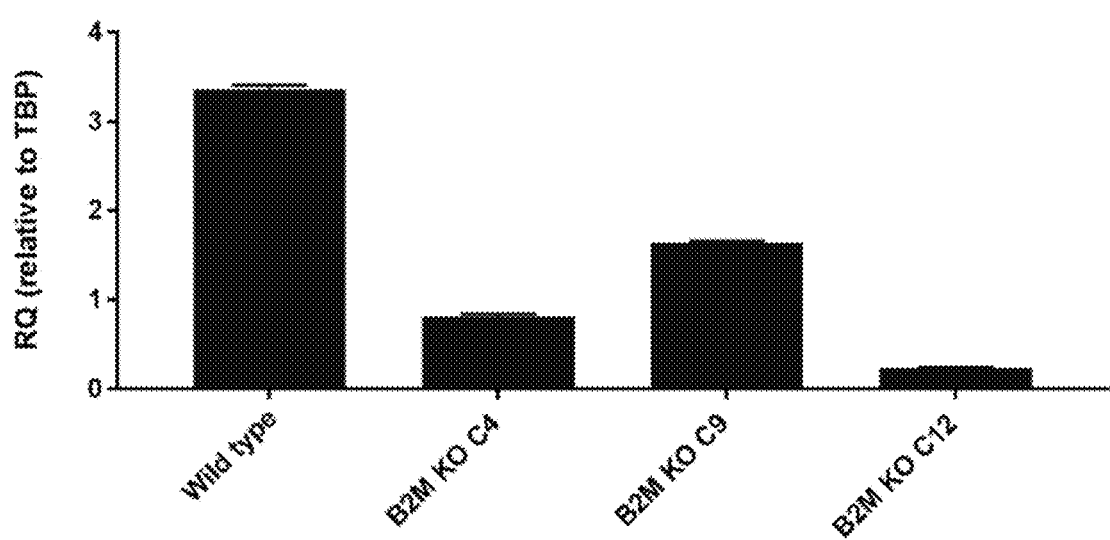
FIG. 5 shows an evaluation of B2M KO iPSC clones. All three B2M KO clones tested showed decreased mRNA expression of B2M relative to a wild type, or unmodified cell.
Figure 6A:
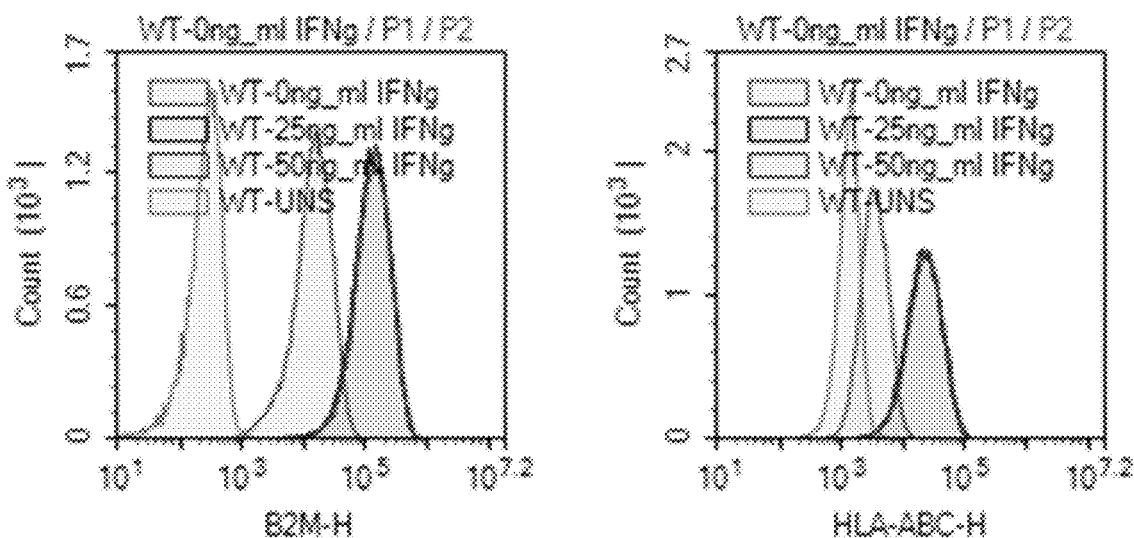
FIGS. 6A-6D show expression of B2M and HLA-ABC in B2M KO iPSC clones following a 47-hour treatment with interferon-gamma.
Figure 6B:
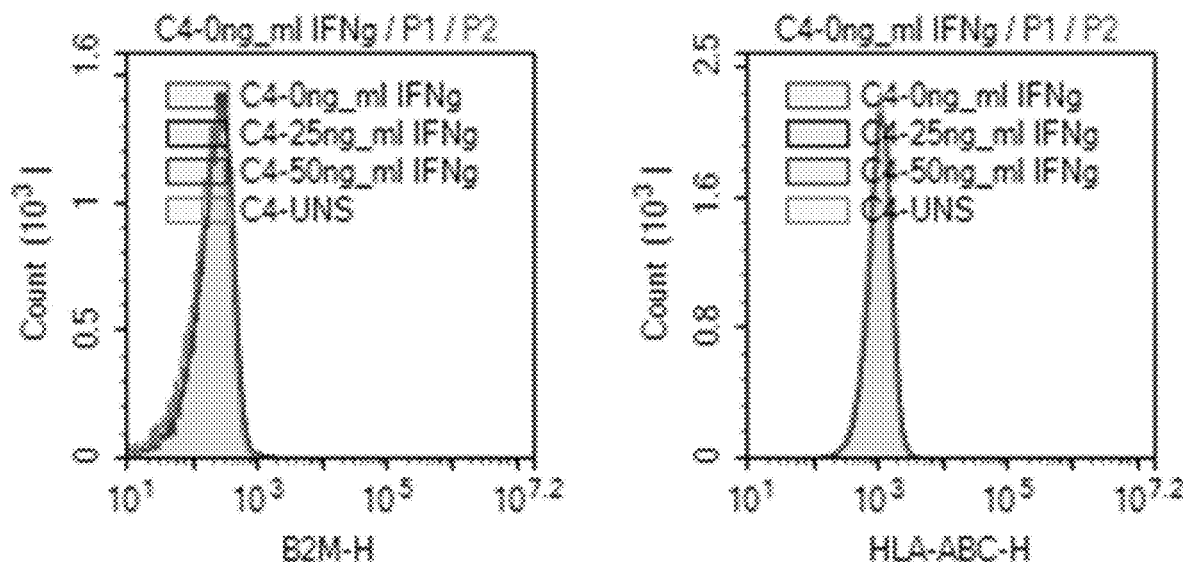
Figure 6C:
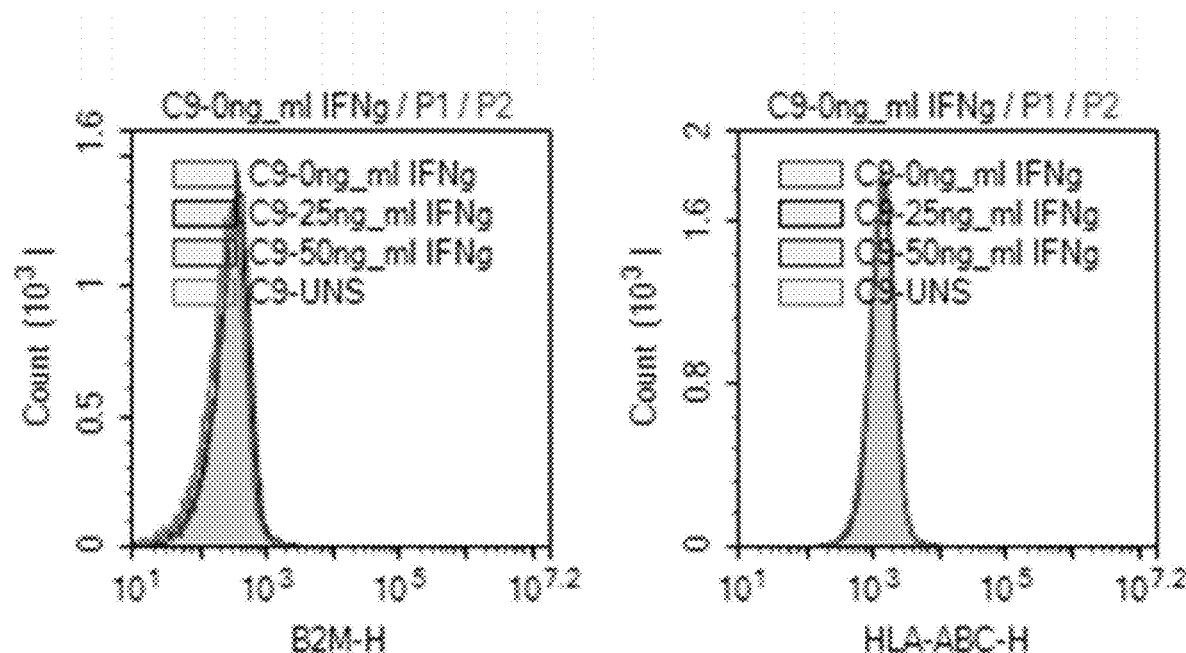
Figure 6D:
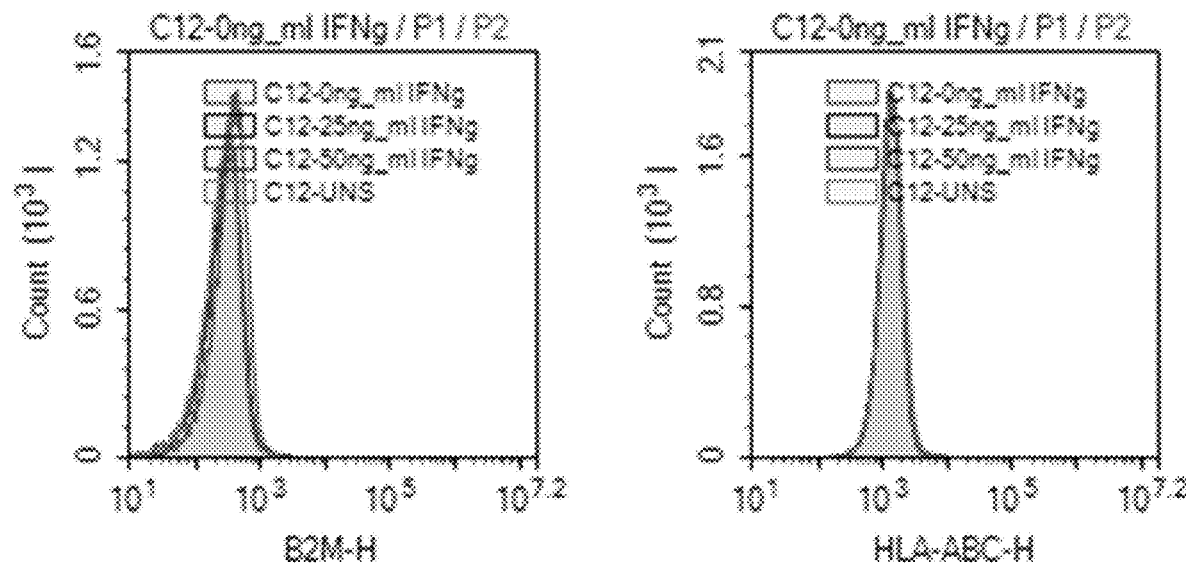
Figure 7A:
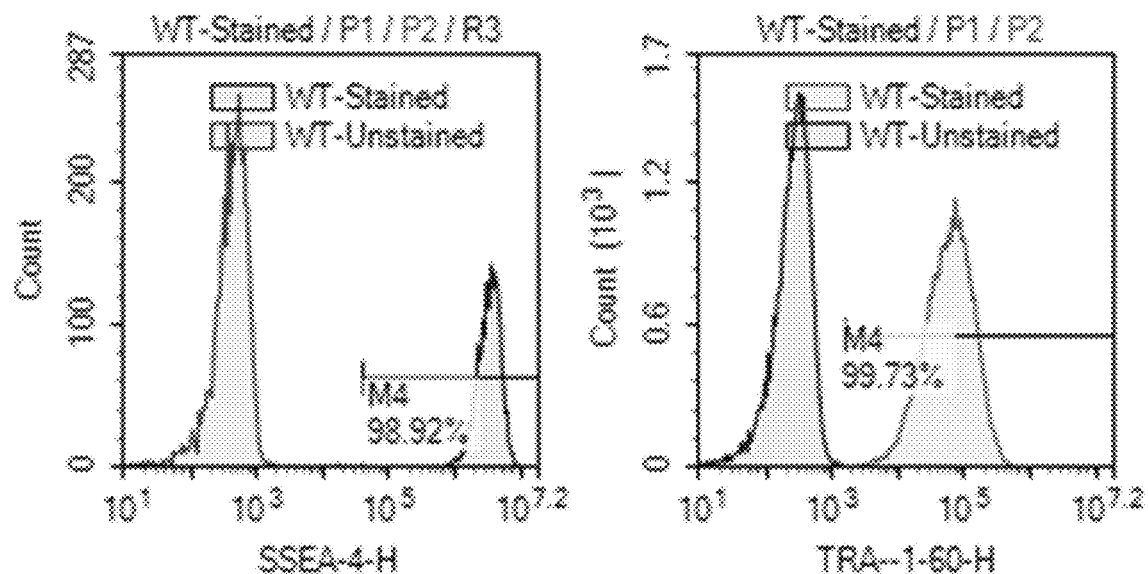
FIGS. 7A-7D demonstrate the pluripotency of B2M KO iPSC clones through evaluation of expression levels of SSEA-4 and TRA-1-60.
Figure 7B:
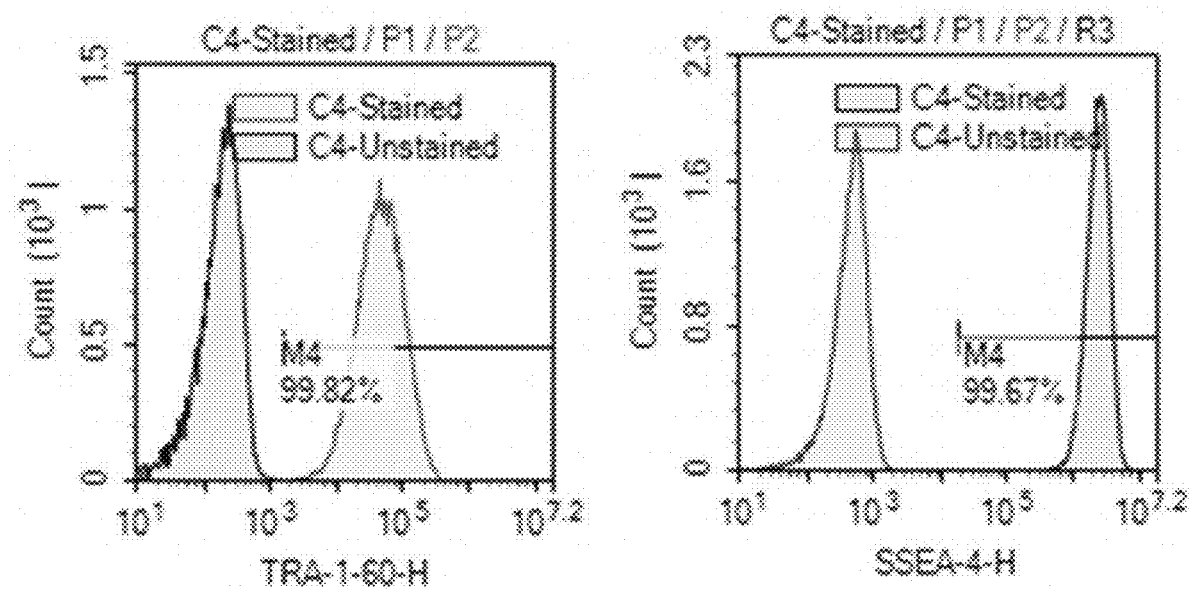
Figure 7C:
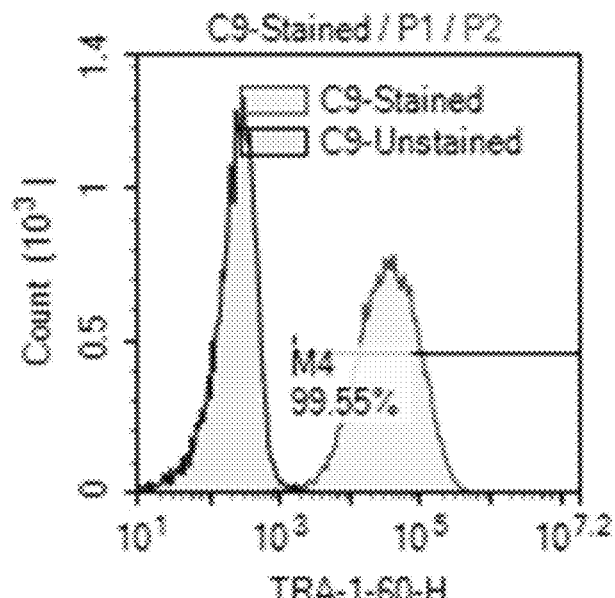
Figure 7D:
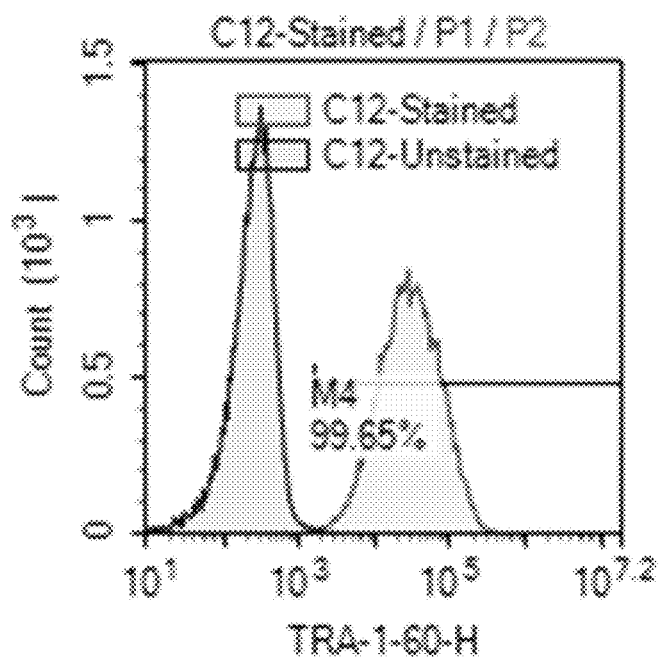
Figure 8:
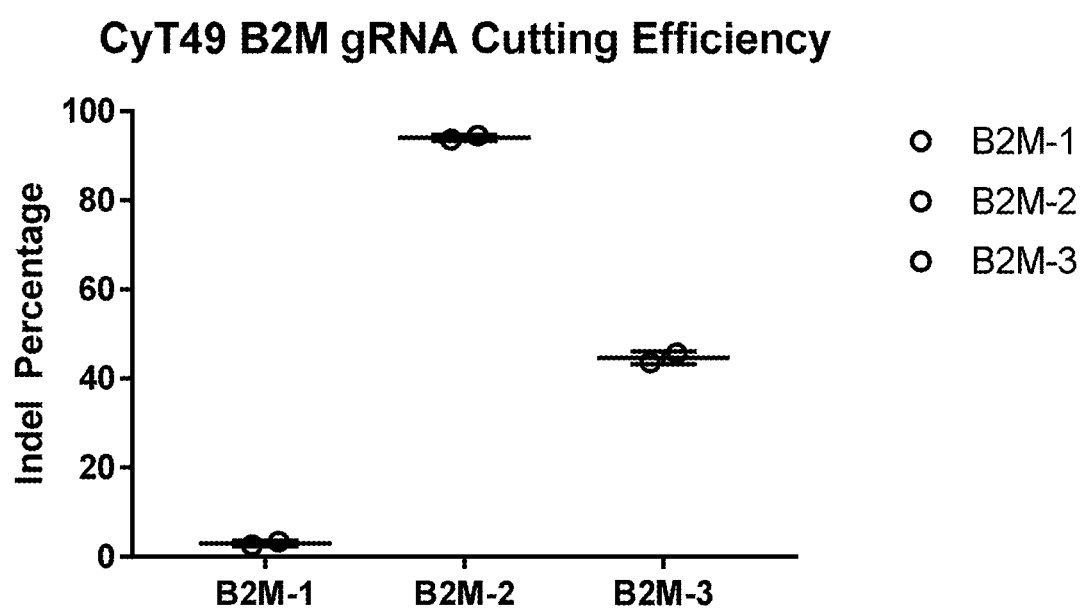
FIG. 8 shows TIDE analysis of B2M gRNA cutting in CyT49 cells. B2M gRNAs-1, -2, or -3 were tested.

Clone sequences were aligned in Snapgene software to determine indel identity and homo- or heterozygosity. As shown in FIG. 4B, 8 clones were homozygous for B2M KO and 7 clones were heterozygous for B2M KO. Homozygous clones with desired edits were expanded and further verified through sequencing and flow cytometry. Clones were initially maintained in StemFlex media on Vitronectin coated plates then eventually transitioned to Advanced 20/10/10 medium and Laminin-521 coated vessels.

Cells were further maintained on Laminin-521 coated flasks with Advanced 20/10/10. Edited clones were verified for indel identity through PCR of the B2M region and Sanger sequencing. Knockout was verified through Flow Cytometry for B2M and HLA-A (See Tables 8 and 9 for list of antibodies utilized) and Taqman qPCR analysis of B2M expression using standard Taqman protocols (Taqman FastAdvanced Mastermix, ThermoFisher, cat #4444556). Levels of B2M expression for three B2M KO clones as well as wild type (unmodified) cells is presented in FIG. 5. All three KO clones tested showed decreased mRNA expression of B2M relative to wild type cell.

TABLE 8

Antibodies for Pluripotency Flow Cytometry

| Target | Fluorophore | Manufacturer | Catalog number |
|---|---|---|---|
| SSEA-4 | AlexaFluor 647 | ThermoFisher | SSEA421 |
| Tra-1-60 | PE | ThermoFisher | MA1-023-PE |
| Tra-1-81 | PE | BD Bioscience | 560161 |

TABLE 9

Antibodies for B2M and HLA-ABC

| Target | Fluorophore | Manufacturer | Catalog number |
|---|---|---|---|
| B2M | AlexaFluor 647 | Biolegend | 316311 |
| HLA-ABC | FITC | BD Pharmigen | 555552 |

RNA extraction was carried out using Qiagen RNeasy kit with RNase-Free DNase according to manufacturer's instructions (Qiagen, cat #74104 and 79254). cDNA synthesis was carried out using Advanced iScript cDNA synthesis kit for RT-qPCR (BioRad, cat #1725037) according to manufacturer's instructions. Karyotypic status of clones was evaluated through Karyostat service (ThermoFisher) and tracking of known karyotypic abnormality BCL2L1 through ddPCR using manufacturer's instructions and ddPCR supermix for Probes (no dUTP) (BioRad, cat #1863024; Primers in Table 10) with an annealing temperature of 59° C. and RPP30 as a reference assay.

TABLE 10 ddPCR Pruner Probe Sets

| | BCL2L1 (Target) | SEQ ID NO: | RPP30 (Reference) | SEQ ID NO: |
|---|---|---|---|---|
| Forward Primer | TCTGCAGAAGGCTAC CCCTA | 7 | GATTTTGGACCTG CGAGCG | 9 |
| Reverse Primer | TGCTGTGTCTAAGAC CTCTTTCAT | 8 | CAAGCCTGGCAAT AAACAATGA | 10 |
| Probe | Universal probe #44 (Sigma, cat# 4688040001) | — | 5' VIC-CTGCTGCCTGAAC AT-3'-MGB-NFQ | 11 |

Resulting amplicons were gel-checked on a pre-cast 2% agarose gel (ThermoFisher, cat #G501802) and submitted for PCR cleanup and Sanger sequencing. Resulting sequencing files were input into Tsunami software along with gRNA sequence and a control sequence file to determine indel identity and percentage.

Clones were also confirmed to be negative for expression of B2M and MHC Class I antigens (HLA-A, B, C), with or without Interferon-gamma treatment (25 ng/mL, R & D Systems, 285-IF) through flow cytometry of the same. See FIGS. 6A-6D.

Clones were confirmed to retain pluripotency through flow cytometry for pluripotency cell surface markers (FIGS. 7A-7D). Additional confirmation of pluripotency included Taqman Scorecard (ThermoFisher, cat #A15872), Thermo Pluritest service and Trilineage differentiation (see below for full protocol).

Cells were dissociated and counted as above, prior to centrifugation and resuspension in Advanced 20/10/10 media with 2 μM Y-27632 (Tocris, cat #1245) up to 1×10⁶/ mL. Resuspended cells were then filtered through a 40 μM filter (Fisherbrand, cat #22363547) and 5 mL of the suspension was plated in a single well of an ultra-low attachment 6-well dish (Corning, cat #3471). The cells were then placed on an orbital shaker overnight at 98 RPM to form aggregates. After 16 hours, spent media was removed from each well by carefully swirling plate to collect aggregates. 4 mL of fresh Advanced 20/10/10 was added.

After 24 additional hours, the cells were differentiated. Aggregates were first collected into a 50 mL conical tube and centrifuged at 1000 RPM for 1 min to settle aggregates. Media was aspirated and aggregates were washed with DMEM/F12. Aggregates were again collected by centrifugation and resuspended in 4 mL of respective differentiation media before being returned to dish and shaker. All differentiations used the following base media: 480 mL IMDM+Glutamax (Gibco, cat #31980030), 480 mL F12+Glutamax (Gibco, cat #31765035), 10 mL of Non-essential amino acids (Gibco, cat #11140076), 5 mL of 20% BSA (Sigma, cat #A7638-5G), 2 mL Chemically defined Lipids (Gibco, cat #11905031), 1 mL of 200 mM Ascorbic Acid (Sigma, cat #A4403-100MG), 1 mL of 10 mg/mL holo-transferrin (Sigma, cat #T0665), and 100 µL of 140 µg/ml sodium selenite (Sigma, cat #S5261). To differentiate cells into an ectoderm cell, a final concentration of 4 mg/mL insulin (Gibco, cat #12585014), 2 µM A83-01, 2 µM Dorsomorphin (Peprotech, cat #8666430) and 2 µM PNU-74654 were used for two days. To differentiate cells into a mesoderm cell, a final concentration of 1 µg/mL Insulin, 0.1 µM PIK-90, 3 µM CHIR99021 (Peprotech, cat #2520691) and 0.5 µM LDN193189 (Peprotech, cat #1062443) was used for two days. For day 1 of endoderm differentiation, a final concentration of 0.2 µg/mL insulin, 0.1 µM PIK-90, 100 ng/mL Activin-A (Peprotech, cat #120-00), 2 µM CHIR99021 and 20 ng/mL of FGF basic (Peprotech, cat #101-18b) was used. An additional two days of differentiation for endoderm were carried out with: 0.2 µg/mL insulin, 0.1 µM PIK-90, 100 ng/mL Activin A and 0.25 µM LDN193189. Media was changed daily for all differentiations. All were collected for RNA analysis using Taqman Scorecard at day 3.

Example 2: Cell Maintenance and Expansion

Maintenance of hESC/hiPSCs.

Cells of human embryonic stem cell (hESCs) line CyT49 were maintained, cultured, passaged, proliferated, and plated as described in Schulz et al. (2012) PLoS ONE 7(5): e37004. CyT49 cells were disassociated using ACCUTASE® (Stemcell Technologies 07920 or equivalent).

Human induced pluripotent stem cells (hiPSCs), such as the TC1133 cell line (Lonza), were maintained in StemFlex Complete (Life Technologies, A3349401) on BIOLAMININ 521 CTG (BioLamina Cat #CT521) coated tissue culture plates. The plates were pre-coated with a 1:10 or a 1:20 dilution of BIOLAMININ in DPBS, calcium, magnesium (Life Technologies, 14040133) for 2 hours at 37° C. The cells were fed daily with StemFlex media. For passaging of the cells, same densities of cells as for CyT49 were used. For plating of the cells as single cells, the cells were plated with 1% RevitaCell™ Supplement (100×) (Thermofisher Cat #A2644501) in StemFlex on BIOLAMININ coated plates.

Single Cell Cloning of hPSCs.

For single cell cloning, hPSCs (hESCs or hiPSCs) were fed with StemFlex Complete with Revitacell (for a final concentration of 1× Revitacell) 3-4 hours prior to dissociation with ACCUTASE®. Following dissociation, the cells were sorted as a single cell per well of a BIOLAMININ coated 96 well tissue culture plate. The WOLF FACS-sorter (Nanocellect) was used to sort single cells into the wells. The plates were pre-filled with 100-200 µL of StemFlex Complete with Revitacell. Three days post cell seeding, the cells were fed with fresh StemFlex and continued to be fed every other day with 100-200 µL of media. After 10 days of growth, the cells were fed daily with StemFlex until day 12-14. At this time, the plates were dissociated with ACCUTASE® and the collected cell suspensions were split 1:2 with half going into a new 96 well plate for maintenance and half going into a DNA extraction solution QuickExtract™ DNA Extraction Solution (Lucigen). Following DNA extraction, PCR was performed to assess presence or absence of desired gene edits at the targeted DNA locus. Sanger sequencing was used to verify desired edits.

Expansion of Single Cell Derived hPSCs Clones.

For CyT49, successfully targeted clones were passaged onto 24-well plates with pure 10% XF KSR A10H10 media but on BIOLAMININ-coated plates. Following the 24-well stage, CyT49 clones were passaged as described in Schulz et al. (2012) PLoS ONE 7(5): e37004.

For hiPSCs (TC1133), cells were maintained in StemFlex Complete throughout the cloning and regular maintenance processes on BIOLAMININ-coated plates with Revitacell at the passaging stages.

Example 3: Generation of B2M Knock-Out Human Pluripotent Stem Cells (hPSCs)

Guide RNA (gRNA) Selection for B2M in hPSCs.

The three B2M targeting gRNAs described above in Example 1 were used to target the B2M gene in hPSCs. To assess their cutting efficiency in hPSCs, CyT49 cells were electroporated using the Neon Electroporator (Neon Transfection Kit ThermoFisher Cat #MPK5000) with a ribonucleoprotein (RNP) mixture of Cas9 protein (Biomay) and guide RNA (Synthego) at a molar ratio of 3:1 (gRNA:Cas9) with absolute values of 125 pmol Cas9 and 375 pmol gRNA. To form the RNP complex, gRNA and Cas9 were combined in one vessel with R-buffer (Neon Transfection Kit) to a total volume of 25 µL and incubated for 15 min at RT. Cells were dissociated using ACCUTASE®, then resuspended in DMEM/F12 media (Gibco, cat #11320033), counted using an NC-200 (Chemometec) and centrifuged. A total of $1 \times 10^6$ cells were resuspended with the RNP complex and R-buffer was added to a total volume of 125 µL. This mixture was then electroporated with 2 pulses for 30 ms at 1100 V. Following electroporation, the cells were pipetted out into an Eppendorf tube filled with StemFlex media with RevitaCell. This cell suspension was then plated into tissue culture dishes pre-coated with BIOLAMININ 521 CTG at 1:20 dilution. Cells were cultured in a normoxia incubator (37° C., 8% $CO_2$) for 48 hours. After 48 hours, genomic DNA was harvested from the cells using QuickExtract (Lucigen, Middleton, Wis.; Cat #QE09050).

PCR for the target B2M sequence was performed and the resulting amplified DNA was assessed for cutting efficiency by TIDE analysis. PCR for relevant regions was performed using Platinum Taq Supermix (Invitrogen, cat #125320176 and Cat #11495017). The sequences of the PCR primers are presented in Table 4; and the cycling conditions provided in Table 5. The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 8 shows the cutting efficiency for the 3 B2M gRNAs.

Off-targets of the selected gRNAs were assessed in the stem cell-derived DNA using hybrid capture analysis of the sequence similarity predicted sites. B2M-2 and B2M-3 guides did not show detectable off-target effects. B2M-2 gRNA was chosen for further clone generation due to its high on-target activity and undetectable off-target activity.

B2M KO hPSC Clone Generation and Characterization.

Using B2M-2 gRNA, CyT49 hESCs were electroporated and single-cell sorted 3 days post electroporation using the WOLF FACS-sorter (Nanocellect) into BIOLAMININ 521 CTG coated 96-well plates with StemFlex and Revitacell. Plated single cells were grown in a normoxia incubator (37° C., 8% $CO_2$) with every other day media changes until colonies were large enough to be re-seeded as single cells. When confluent, samples were split for maintenance and genomic DNA extraction.

Figure 9A:
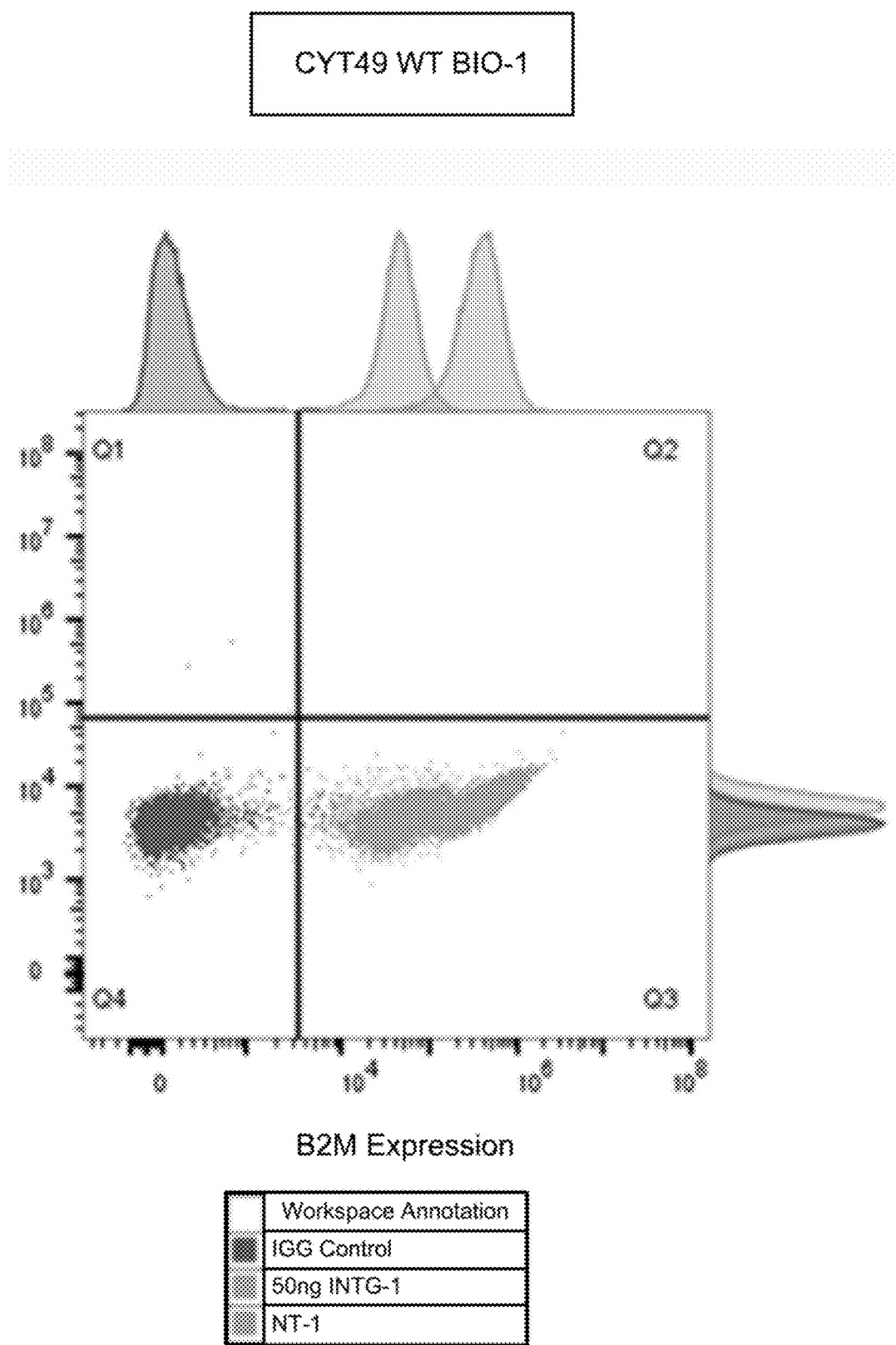
FIGS. 9A-9B show the flow cytometry assessment of B2M expression with and without IFN-γ in WT CyT49 cells (FIG. 9A) and edited CyT49 cells (FIG. 9B).
Figure 9B:
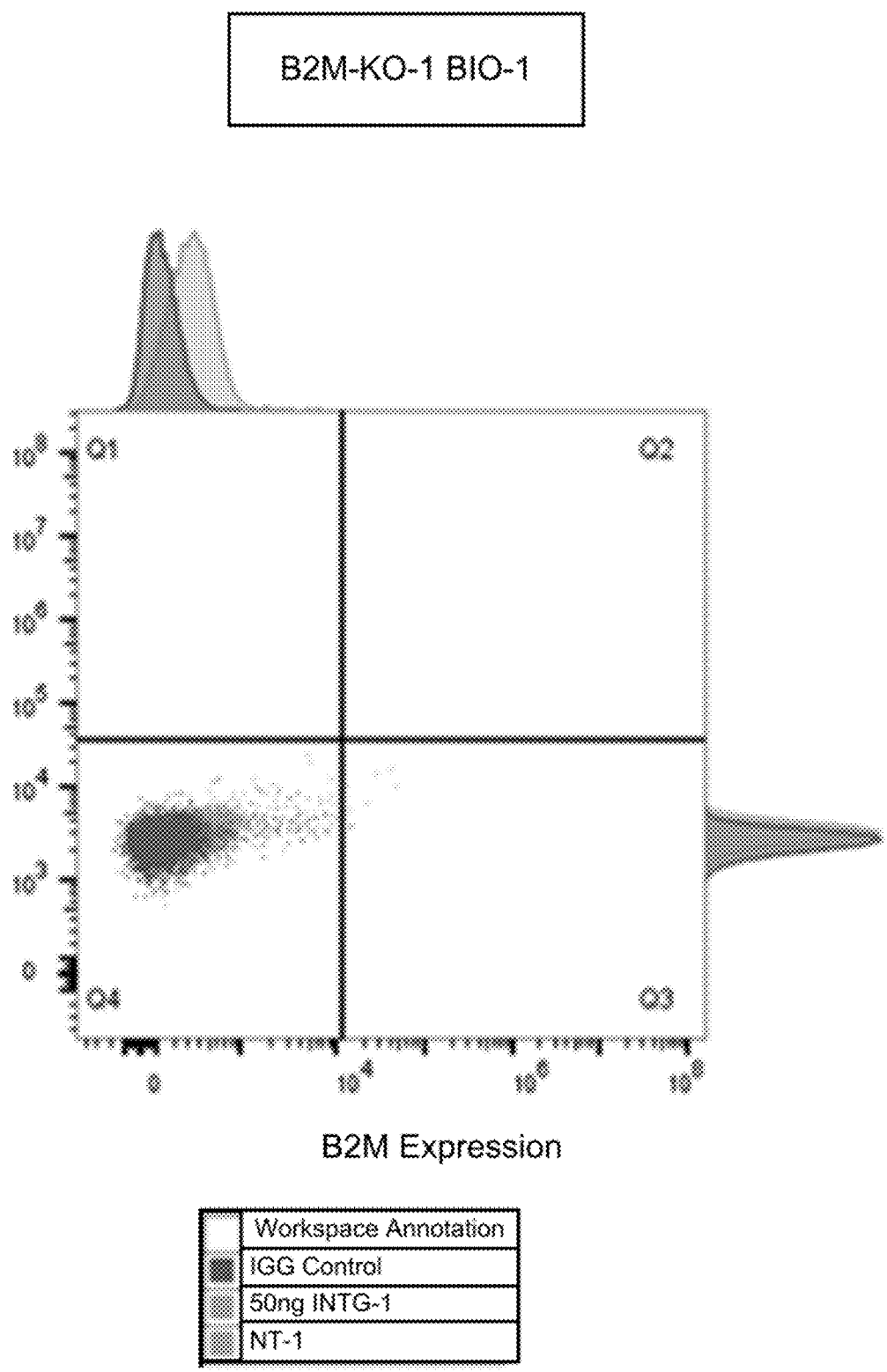

The B2M KO state of clones was confirmed via PCR and Sanger sequencing. The resulting DNA sequences of the target B2M region were aligned in Snapgene software to determine indel identity and homo- or heterozygosity. Clones with desired edits were expanded and further verified through flow cytometry assessment for B2M expression (See Table 11 for list of antibodies utilized). Clones were assessed with or without Interferon-gamma treatment (25 ng/mL, R & D Systems, 285-IF). FIG. 9A shows B2M expression in wild type cells and FIG. 9B presents B2M expression in KO cells. Karyotypic status of clones was evaluated through Cell Line Genetics service (Madison, Wis.) and normal karyotype was reported.

TABLE 11

Antibodies for Pluripotency Flow Cytometry

| Antigen | Clone | Fluorophore | Manufacturer | Catalog # |
|---|---|---|---|---|
| Oct3/4 | 40/3 | Alexa 647 | BD Bioscience | 560329 |
| SOX2 | 030-678 | PE | BD Bioscience | 562195 |
| B2M | 2M2 | PE | Biolegend | 316305 |
| HLA-ABC | W6/32 | Alexa 488 | Biolegend | 311415 |
| mIgG1 kappa | N/A | PE | BD Bioscience | 555749 |
| PD-L1 | B7-H1 | Alexa-488 | ThermoFisher | 53-5983-42 |
| HLA-E | 3D12 | PE | ThermoFisher | 12-9953-42 |

Clones were confirmed to retain pluripotency through intracellular flow cytometry for pluripotency markers OCT4 and SOX2. Confirmed pluripotent clones were differentiated to pancreatic endocrine progenitors using previously established methods (Schulz et al. (2012) PLoS ONE 7(5): e37004).

Example 4: Generation of B2M Knock-Out PD-L1 Knock-in Human Pluripotent Stem Cells (hPSCs)

Design of B2M-KO PD-L1-KI Strategy.

Figure 10:
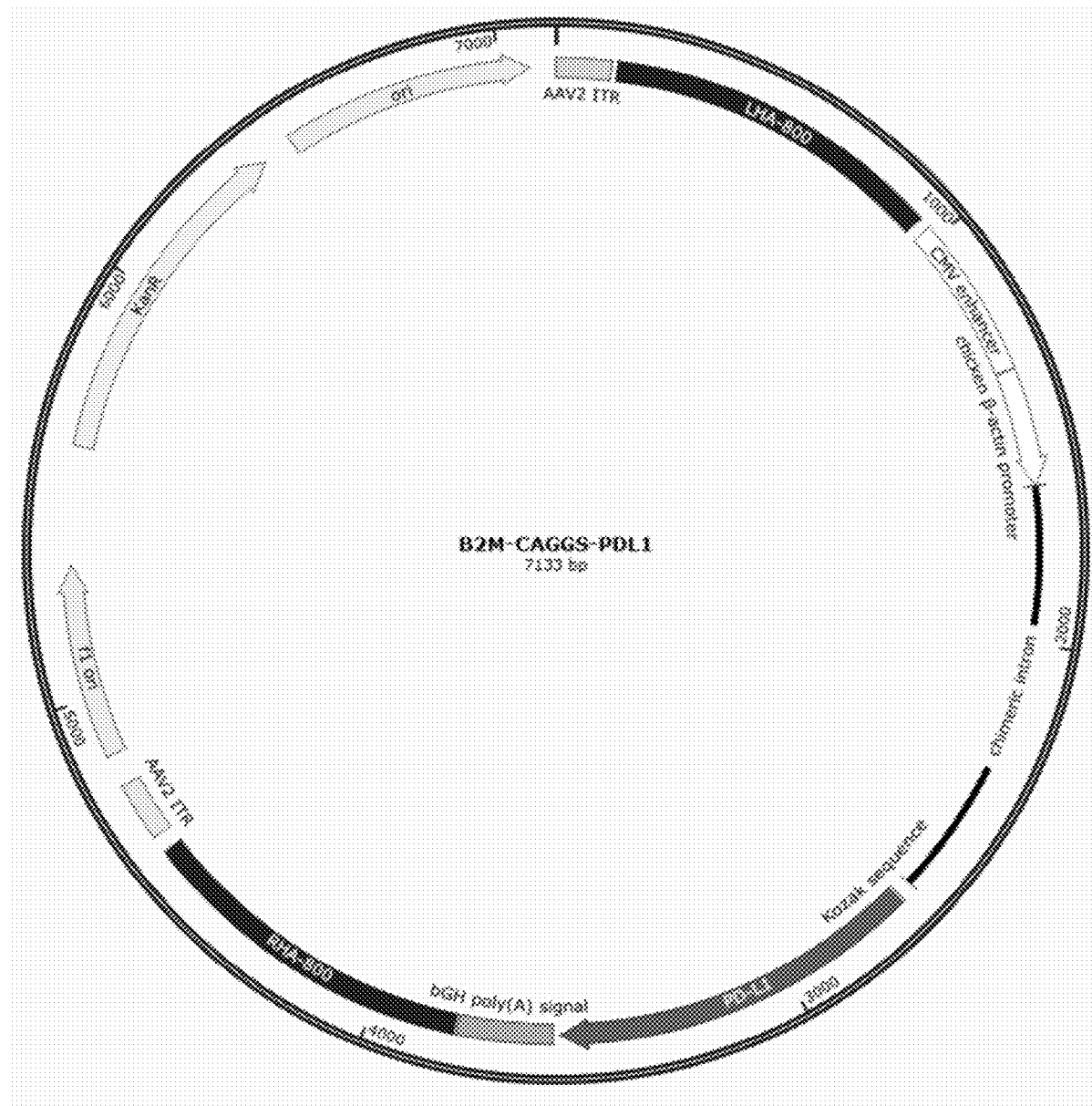
FIG. 10 shows the plasmid map of B2M-CAGGS-PD-L1 donor vector for HDR.

Plasmid design to insert PD-L1 (CD274) into the B2M locus was made such that the starting codon of B2M was removed after undergoing homology directed repair (HDR) to insert PD-L1, nullifying any chance of partial B2M expression. FIG. 10 presents a schematic of the plasmid and Table 12 identifies the elements and locations therein. The donor plasmid contained a CAGGS promoter driven cDNA of PD-L1 flanked by 800 base pair homology arms with identical sequence to the B2M locus around exon 1. The complete sequence of the plasmid is presented in SEQ ID NO: 33.

TABLE 12

Elements of B2M-CAGGS-PD-L1 Donor Plasmid

| Element | Location (size in bp) | SEQ ID NO: |
|---|---|---|
| Left ITR | 1-130 (130) | 12 |
| LHA-B2M | 145-944 (800) | 13 |

TABLE 12-continued

Elements of B2M-CAGGS-PD-L1 Donor Plasmid

| Element | Location (size in bp) | SEQ ID NO: |
|---|---|---|
| CMV enhancer | 973-1352 (380) | 14 |
| chicken β-actin promoter | 1355-1630 (276) | 15 |
| chimeric intron | 1631-2639 (1009) | 16 |
| PD-L1 | 2684-3556 (873) | 17 |
| bGH poly(A) signal | 3574-3798 (225) | 18 |
| RHA-B2M | 3805-4604 (800) | 19 |
| Right ITR | 4646-4786 (141) | 20 |

The B2M-2 gRNA was used to facilitate insertion of the PD-L1 transgene at the targeted B2M locus. The PD-L1 donor plasmid was introduced along with the RNP complex made up of the B2M targeting gRNA and Cas9 protein. Per 1 million of CyT49 cells, 4 µg of plasmid DNA was delivered along with the RNP. Electroporation was carried out as described in Example 3. Seven days post electroporation, the cells were sorted for PD-L1 surface expression using the WOLF FACS-sorter (Nanocellect) into BIO-LAMININ 521 CTG coated 96-well plates with StemFlex with Revitacell. For FACS-sorting, unedited cells served as a negative control. PD-L1 positive cells were selected for sorting and single cell cloning.

To detect the PD-L1 surface expression, anti-PD-L1 fluorescent antibodies were used (see Table 11). Plated single cells were grown in a normoxia incubator (37° C., 8% $CO_2$) with every other day media changes until colonies were large enough to be re-seeded as single cells. When confluent, samples were split for maintenance and genomic DNA extraction.

Figure 11:
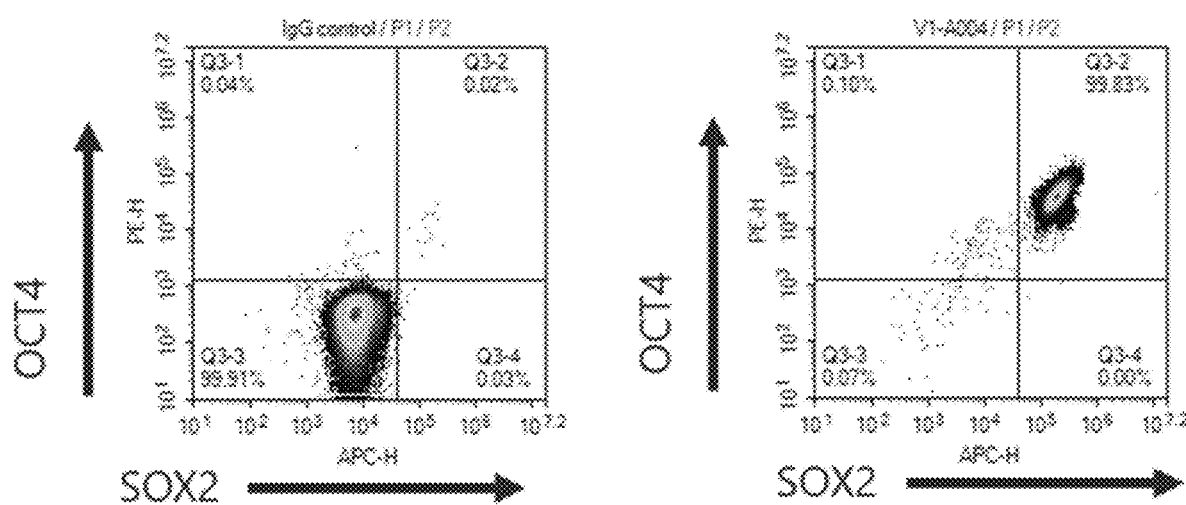
FIG. 11 shows the flow cytometry analysis for pluripotency of B2M KO+PD-L1 KI CyT49 stem cells. The derived clones were >99% double positive for OCT4 and SOX2, two transcription factors vital for pluripotency. IgG was used as a negative control.
Figure 12A:
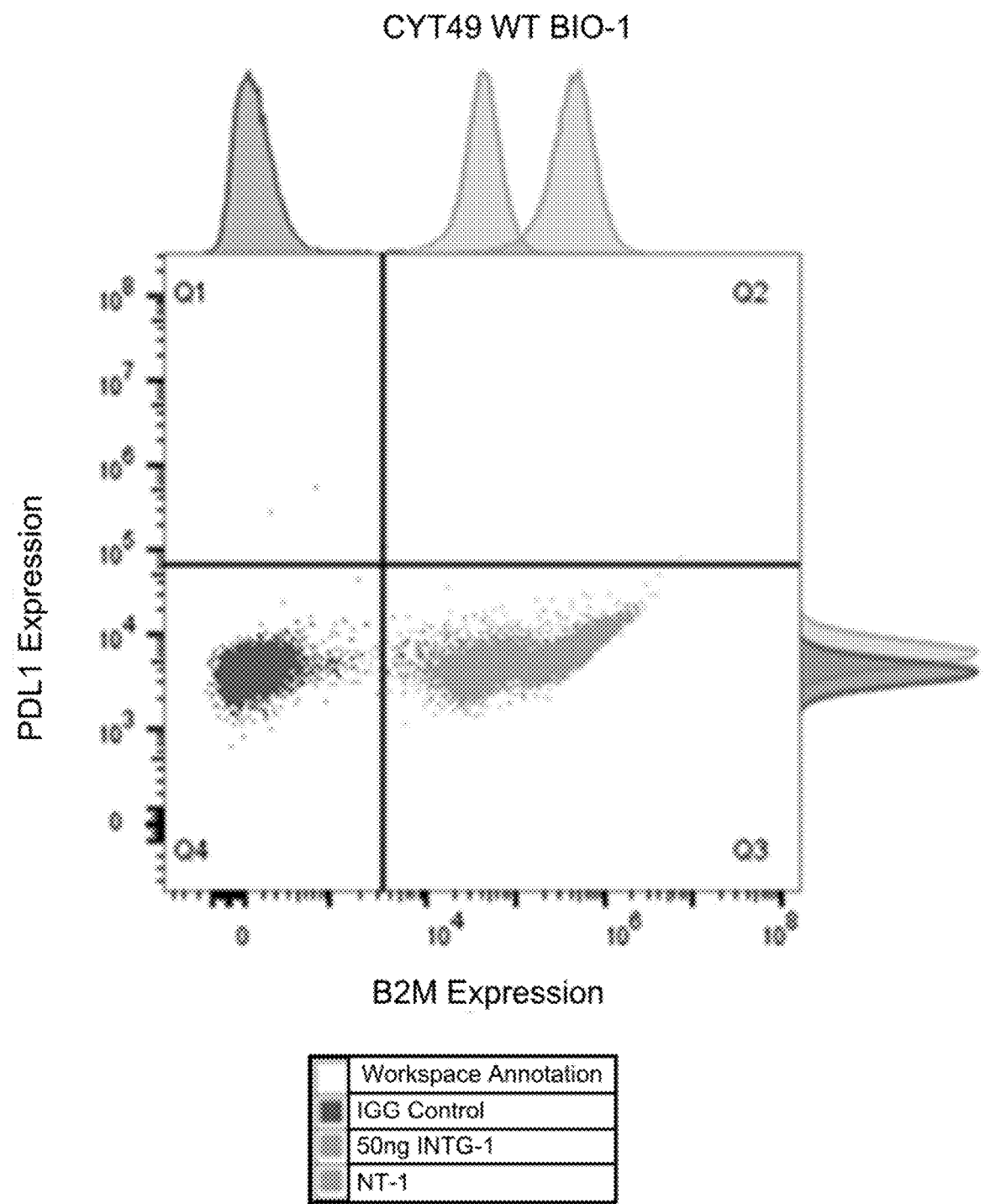
FIGS. 12A-12B show the flow cytometry analysis of WT CyT49 (FIG. 12A) and a B2M KO/PD-L1 KI (FIG. 12B) derived stem cell clones. WT cells upregulate B2M expression in response to IFNγ. B2M KO/PD-L1 KI clones fully express PD-L1 and do not express B2M with or without IFNγ treatment. NT-1=no treatment. INTG-1=50 ng/mL IFNγ 48 hour treated cells.
Figure 12B:
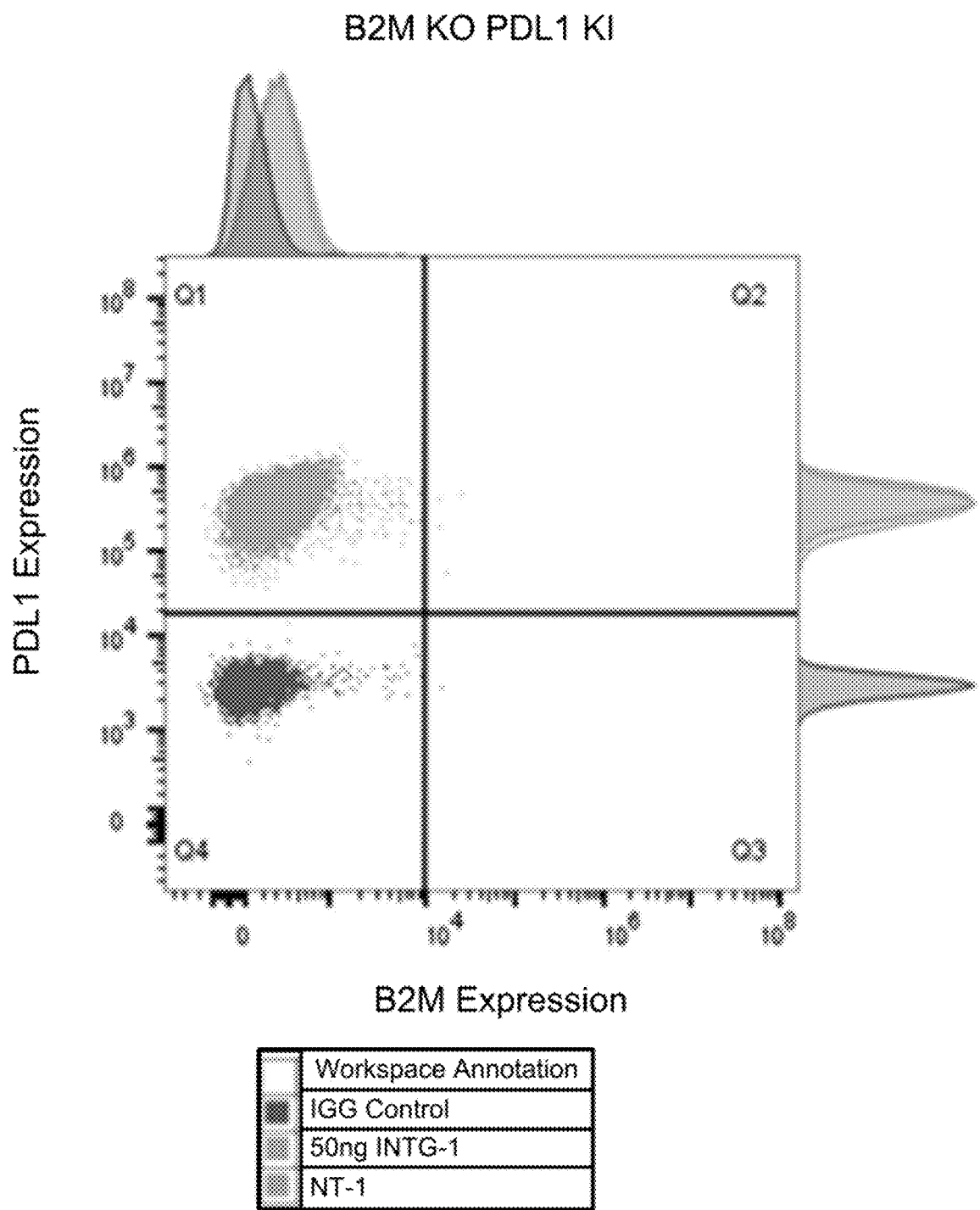

Correctly targeted clones were identified via PCR for the PD-L1 knock-in (KI) insertion using primers that amplify a region from outside the plasmid homology arms to the PD-L1 cDNA insertion enabling amplification of the KI integrated DNA only. On-target insertion was tested for zygosity by PCR to assess if KI occurred in a heterozygous or homozygous manner. If a heterozygous clone was identified, the KI negative allele was sent for Sanger sequencing to verify that it contained a B2M-disrupting indel. The correct KI clones with full B2M disruption (either via KI insertion or indel formation) were expanded in increasing tissue culture formats until a population size of 30 million cells was reached. Approximately 10 clones were expanded in this manner and confirmed to be pluripotent by testing for OCT4 and SOX2 via intracellular flow cytometry (FIG. 11). Clones that passed the above tests, were then tested further for karyotypic analysis (Cell Line Genetics), as described below. Additionally, the clones were then tested for their competence to differentiate to pancreatic endoderm precursors (PEC) via the established protocol (Schulz et al. (2012) PLoS ONE 7(5): e37004), as described below. The loss of B2M was further confirmed by lack of expression of B2M with or without interferon-gamma treatment (25 ng/mL, R & D Systems, 285-1F) through flow cytometry. FIGS. 12A and 12B show PD-L1 expression in wildtype and B2M KO/PD-L1 KI cells, respectively.

Example 5: Generation of B2M Knock-Out HLA-E Knock-in Human Pluripotent Stem Cells (hPSCs)

Design of B2M-KO HLA-E-KI Strategy.

Figure 13:
FIG. 13 shows the plasmid map of B2M-CAGGS-HLA-E donor vector for HDR.

Plasmid design to insert HLA-E trimer into the B2M locus was made such that the starting codon of B2M was removed after undergoing homology directed repair (HDR) to insert the HLA-E trimer, nullifying any chance of partial B2M expression. FIG. 13 presents a schematic of the plasmid and Table 13 identifies the elements and locations therein. The HLA-E trimer cDNA was composed of a B2M signal peptide fused to an HLA-G presentation peptide fused to the B2M membrane protein fused to the HLA-E protein without its signal peptide. This trimer design has been previously published (Gornalusse et al. (2017) Nat. Biotechnol. 35(8): 765-772). The donor plasmid for HLA-E delivery contains a CAGGS promoter driving expression of the HLA-E trimer flanked by 800 base pair homology arms with identical sequence to the B2M locus around exon 1. The complete sequence of the plasmid is presented in SEQ ID NO: 34.

TABLE 13

Elements of B2M-CAGGS-HLA-E Donor Plasmid

| Element | Location (size in bp) | SEQ ID NO: |
|---|---|---|
| Left ITR | 1-130 (130) | 12 |
| LHA-B2M | 145-944 (800) | 13 |
| CMV enhancer | 973-1352 (380) | 14 |
| chicken β-actin promoter | 1355-1630 (276) | 15 |
| chimeric intron | 1631-2639 (1009) | 16 |
| B2M signal sequence | 2684-2743 (60) | 21 |
| HLA-G peptide | 2744-2770 (27) | 22 |
| GS Linker | 2771-2815 (45) | 23 |
| B2M membrane protein | 2816-3112 (297) | 24 |
| GS Linker | 3113-3172 (60) | 25 |
| HLA-E | 3173-4183 (1011) | 26 |
| bGH poly(A) signal | 4204-4428 (225) | 18 |
| RHA-B2M | 4435-5234 (800) | 19 |
| Right ITR | 5276-5416 (141) | 20 |

The B2M-2 gRNA was used to facilitate insertion of the HLA-E transgene at the targeted B2M locus. The HLA-E donor plasmid was introduced along with the RNP complex made up of the B2M targeting gRNA and Cas9 protein. Per 1 million of CyT49 cells, 4 μg of plasmid DNA was delivered along with the RNP. Electroporation was carried out as described in Example 3. Seven days post electroporation, the cells were sorted for HLA-E surface expression using the WOLF FACS-sorter (Nanocellect) into BIO-LAMININ 521 CTG coated 96-well plates with StemFlex with Revitacell. For FACS-sorting, unedited cells served as a negative control. HLA-E positive cells were selected for sorting and single cell cloning.

To detect the HLA-E surface expression, anti-HLA-E fluorescent antibodies were used (Table 11). Plated single cells were grown in a normoxia incubator (37° C., 8% $CO_2$) with every other day media changes until colonies were large enough to be re-seeded as single cells. When confluent, samples were split for maintenance and genomic DNA extraction.

Figure 14:
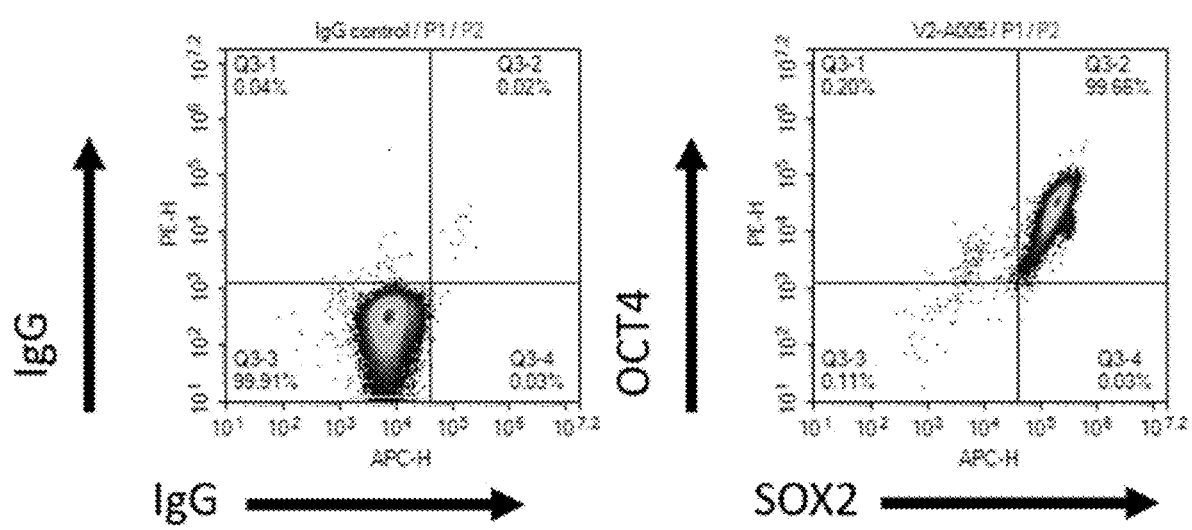
FIG. 14 shows the flow cytometry analysis for pluripotency of B2M KO/HLA-E KI CyT49 stem cells. The derived clones were >99% double positive for OCT4 and SOX2, two transcription factors vital for pluripotency. IgG was used as a negative control.
Figure 15:
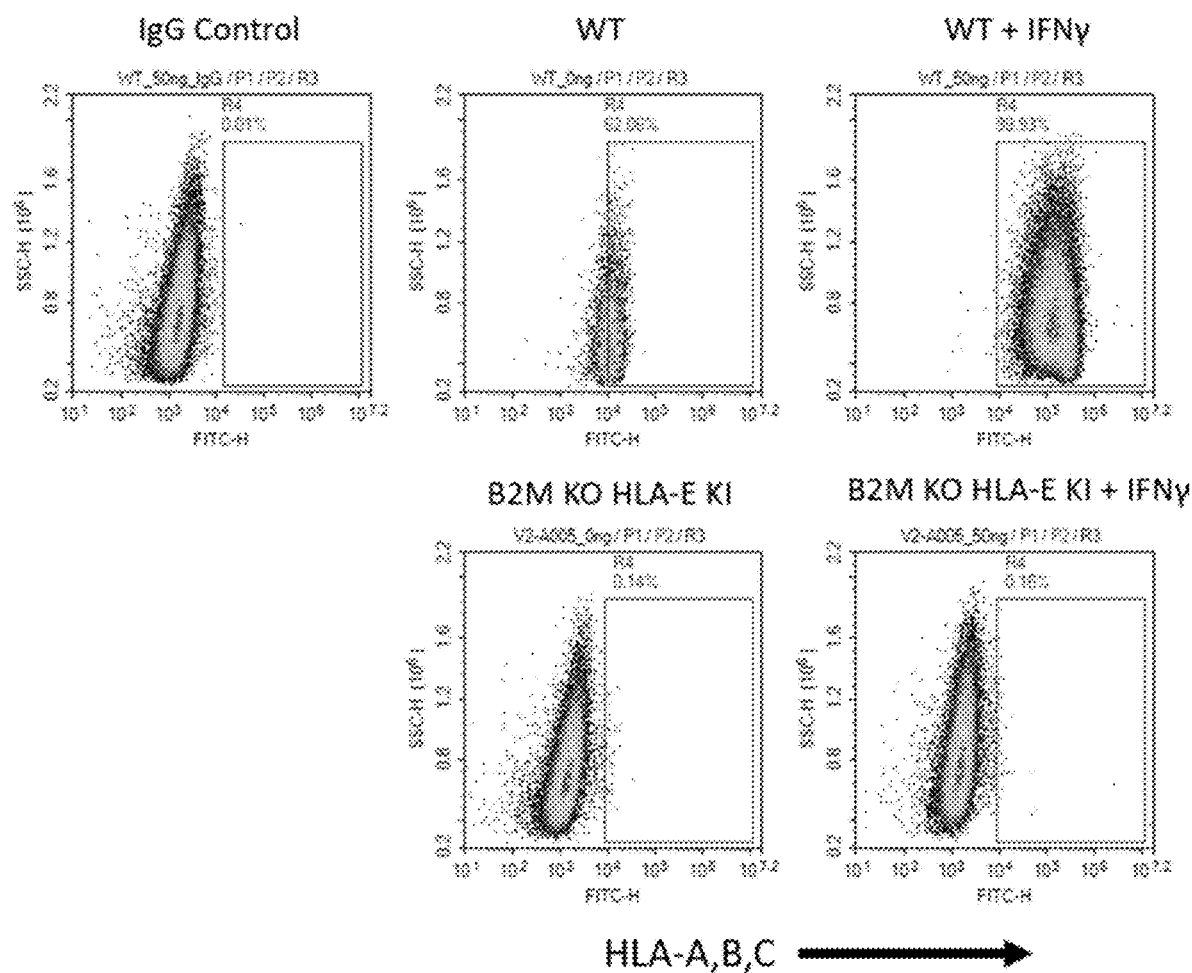
FIG. 15 shows the flow cytometry analysis of WT CyT49 and a B2M KO/HLA-E KI CyT49 stem cell clone. WT cells upregulate HLA-A,B,C expression in response to IFNγ. The B2M KO/HLA-E KI clone does not express HLA-A,B,C with or without IFNγ treatment. IFNγ=50 ng/mL. Cells were treated with IFNγ for 48 hours.
Figure 16:
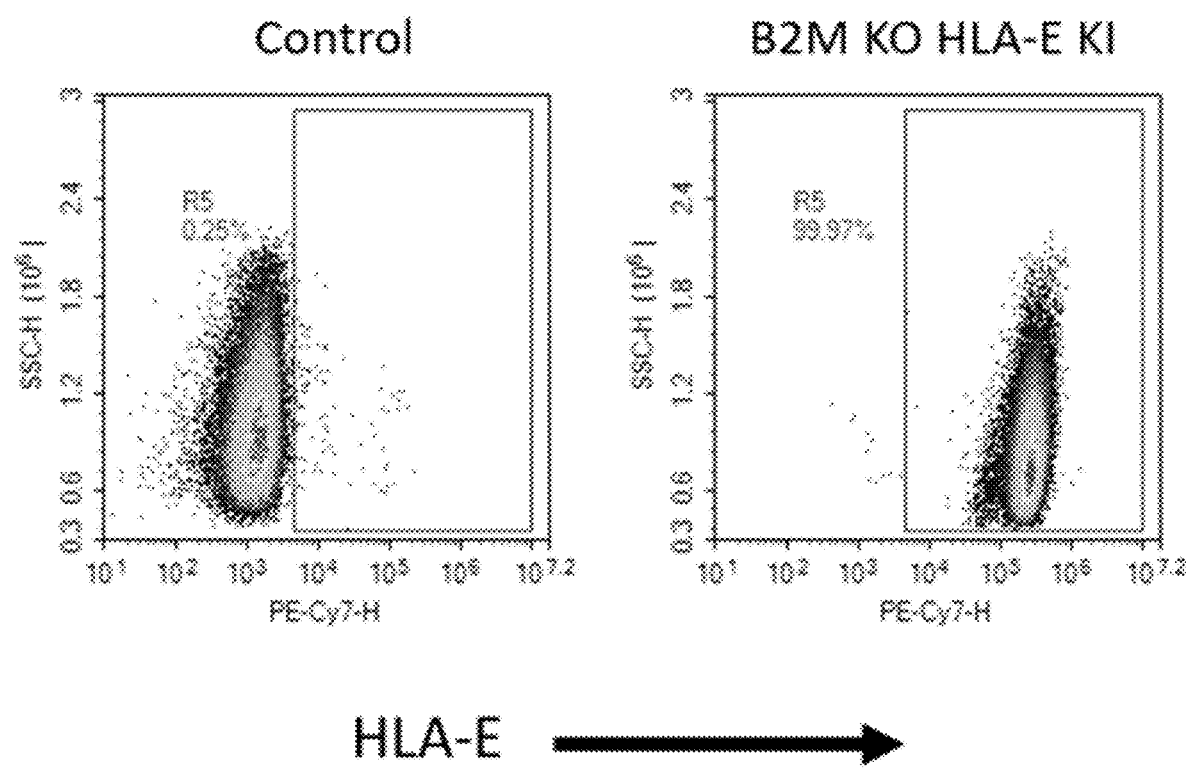
FIG. 16 shows the flow cytometry analysis for HLA-E expression of a B2M KO/HLA-E KI CyT49 stem cell clone. An unedited clone was used as a control for HLA-E expression.

Correctly targeted clones were identified via PCR for the HLA-E knock-in (KI) insertion using primers that amplify a region from outside the plasmid homology arms to the HLA-E cDNA insertion enabling amplification of the KI integrated DNA only. On-target insertion was tested for zygosity by PCR to assess if KI occurred in a heterozygous or homozygous manner. If a heterozygous clone was identified, the KI negative allele was sent for Sanger sequencing to verify that it contained a B2M-disrupting indel. The correct KI clones with full B2M disruption (either via KI insertion or indel formation) were expanded in increasing tissue culture formats until a population size of 30 million cells was reached. Approximately 10 clones were expanded in this manner and confirmed to be pluripotent by testing for OCT4 and SOX2 via intracellular flow cytometry (FIG. 14). Clones that passed the above tests were then tested further for karyotypic analysis (Cell Line Genetics). Additionally, the clones were tested for their competence to differentiate to pancreatic endoderm precursors (PEC) via the established protocol (Schulz et al. (2012) PLoS ONE 7(5): e37004). The loss of B2M was further confirmed by lack of expression of HLA-A,B,C with or without interferon-gamma treatment (50 ng/mL, R & D Systems, 285-IF) through flow cytometry (FIG. 15). FIG. 16 shows HLA-E expression.

Example 6: Karyotype Analysis of Edited Clones

G-Band Karyotyping Analysis of Edited Embryonic Stem (ES) Cells.

1 million of edited ES cells were passaged into a T-25 culture flask with culture media (DMEM/F12+10% Xeno-free KSR with 10 ng/mL Activin and 10 ng/mL Heregulin). After culturing overnight, three T25 culture flasks were shipped to Cytogenetics Laboratory (Cell Line Genetics, Inc.) for Karyotyping analysis; FISH analysis for Chromosome 1, 12, 17, 20; and array comparative genomic hybridization (aCGH) analysis with standard 8×60K array. The G-banding results of selected cells electroporated with non-cutting guides ("NCG"), B2M KO clones, B2M HO/PD-L1 HI clones ("V1-A"), and B2M KO/HLA-E KI clones ("V2-A") are shown in Table 14.

TABLE 14

G-band Karyotyping Results

| Cell Line | Type | Passage | Karyotyping analysis | FISH analysis | aCGH array analysis |
|---|---|---|---|---|---|
| NCG#1 | non-cutting guide | P36 | Normal | Normal | PASS |
| NCG#2 | non-cutting guide | P36 | Normal | Normal | PASS |
| B2MKO#1 | B2M KO | P38 | Normal | Normal | PASS |
| B2MKO#2 | B2M KO | P36 | Normal | Normal | PASS |
| B2MKO#3 | B2M KO | P36 | Normal | Normal | PASS |
| V1-A003 | B2M KO/PD-L1 KI | P37 | Normal | Normal | PASS |
| V1-A004 | B2M KO/PD-L1 KI | P38 | Normal | Normal | PASS |
| V1-A007 | B2M KO/PD-L1 KI | P37 | Normal | Normal | PASS |
| V1-A008 | B2M KO/PD-L1 KI | P38 | Normal | Normal | PASS |
| V2-A005 | B2M KO/HLA-E KI | P42 | Normal | Normal | PASS |
| V2-A006 | B2M KO/HLA-E KI | P38 | Normal | Normal | PASS |
| V2-A007 | B2M KO/HLA-E KI | P38 | Normal | Normal | PASS |

Example 7: Differentiation of Edited Human Embryonic Stem Cells to Pancreatic Endoderm Cells (PECs)

Maintenance of Edited Human Embryonic Stem Cells (ES).

The edited human embryonic stem cells at various passages (P38-42) were seeded at 33,000 cells/cm$^2$ for a 4-day passage or 50,000 cells/cm$^2$ for a 3-day passage with hESM medium (DMEM/F12+10% KSR+10 ng/mL Activin A and 10 ng/mL Heregulin) and final 10% human AB serum.

Aggregation of Edited Human Embryonic Stem Cells for PECs Differentiation.

The edited ES were dissociated into single cells with ACCUTASE® and then centrifuged and resuspended in 2% StemPro (Cat #A1000701, Invitrogen, CA) in DMEM/F12 medium at 1 million cells per ml, and total 350-400 million of cells were seeded in one 850 cm$^2$ roller bottle (Cat #431198, Corning, N.Y.) with rotation speed at 8 RPM±0.5 RPM for 18-20 hours before differentiation. The ES aggregates from edited human embryonic stem cells were differentiation into pancreatic lineages using roller bottles as described in Schulz et al. (2012) PLoS ONE 7(5): e37004.

Example 8: Characterization of Differentiated Pancreatic Endoderm Cells (PECs)

Flow Cytometry for FOXA2 and SOX17 at Stage 1 (DE) and CHGA, PDX1 and NKX6.1 at PEC Stage.

hESC-derived stage 1 aggregates, or hESC-derived pancreatic aggregates, were washed with PBS and then enzymatically dissociated to single cells suspension at 37° C. using ACCUMAX™ (Catalog #A7089, Sigma, Mo.). MACS Separation Buffer (Cat #130-091-221, Miltenyi Biotec, North Rhine-Westphalia, Germany) was added and the suspension was passed through a 40 µm filter and pelleted. For intracellular marker staining, cells were fixed for 30 mins in 4% (wt/v) paraformaldehyde, washed in FACS Buffer (PBS, 0.1% (wt/v) BSA, 0.1% (wt/v) NaN$_3$) and then cells were permeabilized with Perm Buffer (PBS, 0.2% (v/v) Triton X-100 (Cat #A16046, Alfa Aesar, MA), 5% (v/v) normal donkey serum, 0.1% (wt/v) NaN3) for 30 mins on ice and then washed with washing buffer (PBS, 1% (wt/v) BSA, 0.1% (wt/v) NaN$_3$). Cells were incubated with primary antibodies (Table 15) diluted with Block Buffer (PBS, 0.1% (v/v) Triton X-100, 5% (v/v) normal donkey serum, 0.1% (wt/v) NaN3) overnight at 4° C. Cells were washed in IC buffer and then incubated with appropriate secondary antibodies for 60 mins at 4° C. Cells were washed in IC buffer and then in FACS Buffer. Flow cytometry data were acquired with NovoCyte Flow Cytometer (ACEA Biosciences, Brussels). Data were analyzed using FlowJo software (Tree Star, Inc.). Intact cells were identified based on forward (low angle) and side (orthogonal, 90°) light scatter. Background was estimated using antibody controls and undifferentiated cells. In the figures, a representative flow cytometry plot is shown for one of the sub-populations. Numbers reported in the figures represent the percentage of total cells from the intact cells gate.

TABLE 15

Antibodies for flow cytometry for characterization of differentiated PECs

| Antigen | Fluorophore | Source | Dilution |
| --- | --- | --- | --- |
| SOX17 | AF647 | BD Bioscience (Cat#562594) | 1:50 |
| FOXA2 | PE | Miltenyi Biotechnology (Cat#130-107-773) | 1:10 |
| PDX1 | PE | BD Bioscience (Cat#562161) | 1:2.5 |
| NKX6.1 | AF647 | BD Bioscience (Cat#563338) | 1:2.5 |
| CHGA | AF405 | Novus (Cat#NBP2-33198AF405) | 1:1000 |

Figure 17:
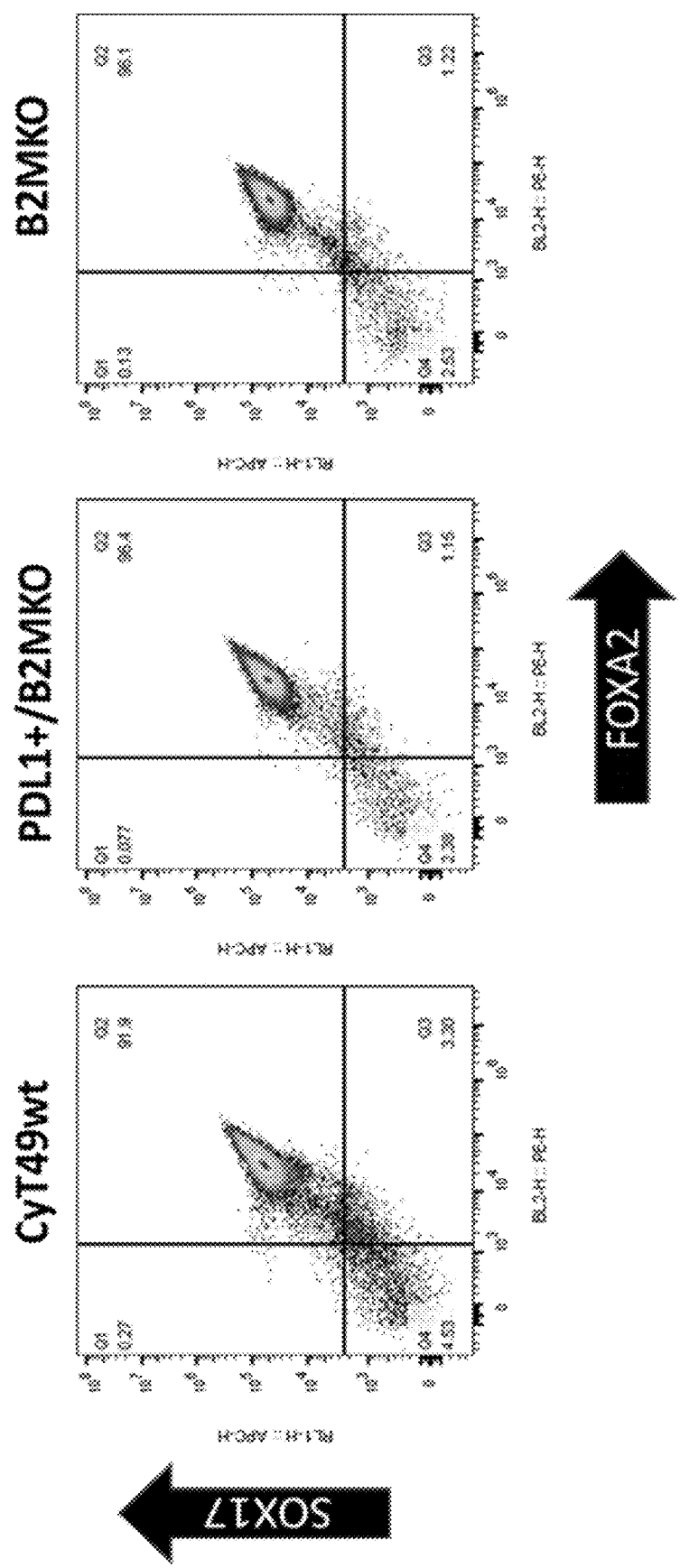
FIG. 17 shows flow cytometry for FOXA2 and SOX17 at Stage 1 (Definitive Endoderm) cells differentiated from wild type, PD-L1 KI/B2M KO, or B2MKO hESCs.
Figure 18:
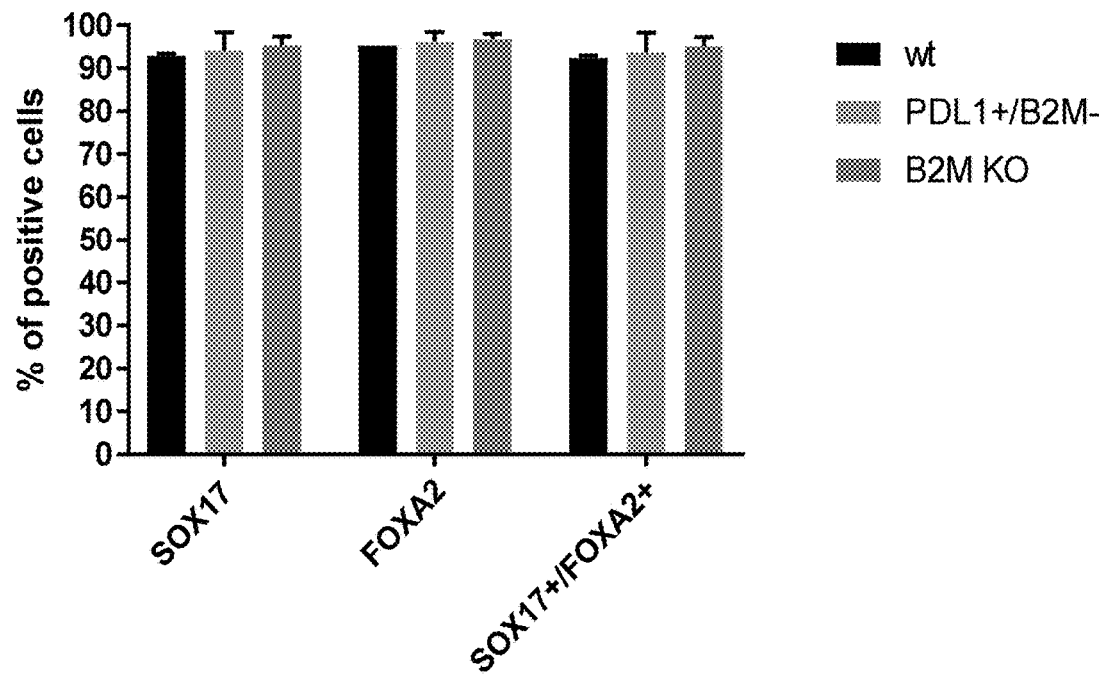
FIG. 18 shows quantitative percentage of FOXA2 and SOX17 expression in Stage 1 (Definitive Endoderm) cells differentiated from wild type, PD-L1 KI/B2M KO, or B2M KO cells.

At DE stage, the population of FOXA2 and SOX17 double positive cells were more than 900% of total cells from CyT49 wild types differentiated cells. The PD-L1 KI/B2M KO, HLA-E KI/B2M KO, and B2M KO cells showed comparable percentage of DE compared to wild type cells (FIGS. 17A-17B and FIG. 18).

Figure 19:
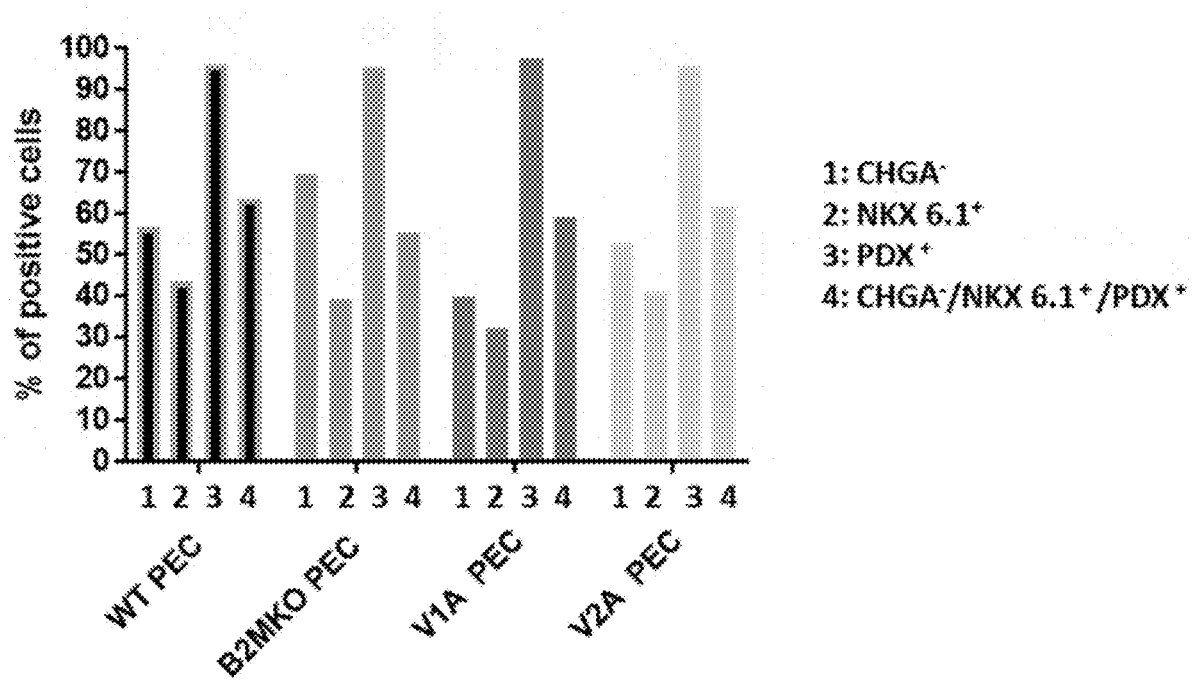
FIG. 19 shows quantitative percentage of CHGA, PDX1, and NKX6.1 expression in Stage 4 (PEC) cells differentiated from wild type, B2M KO, PD-L1 KI/B2M KO (V1A), or HLA-E KI/B2M KO (V2A) cells.
Figure 20:
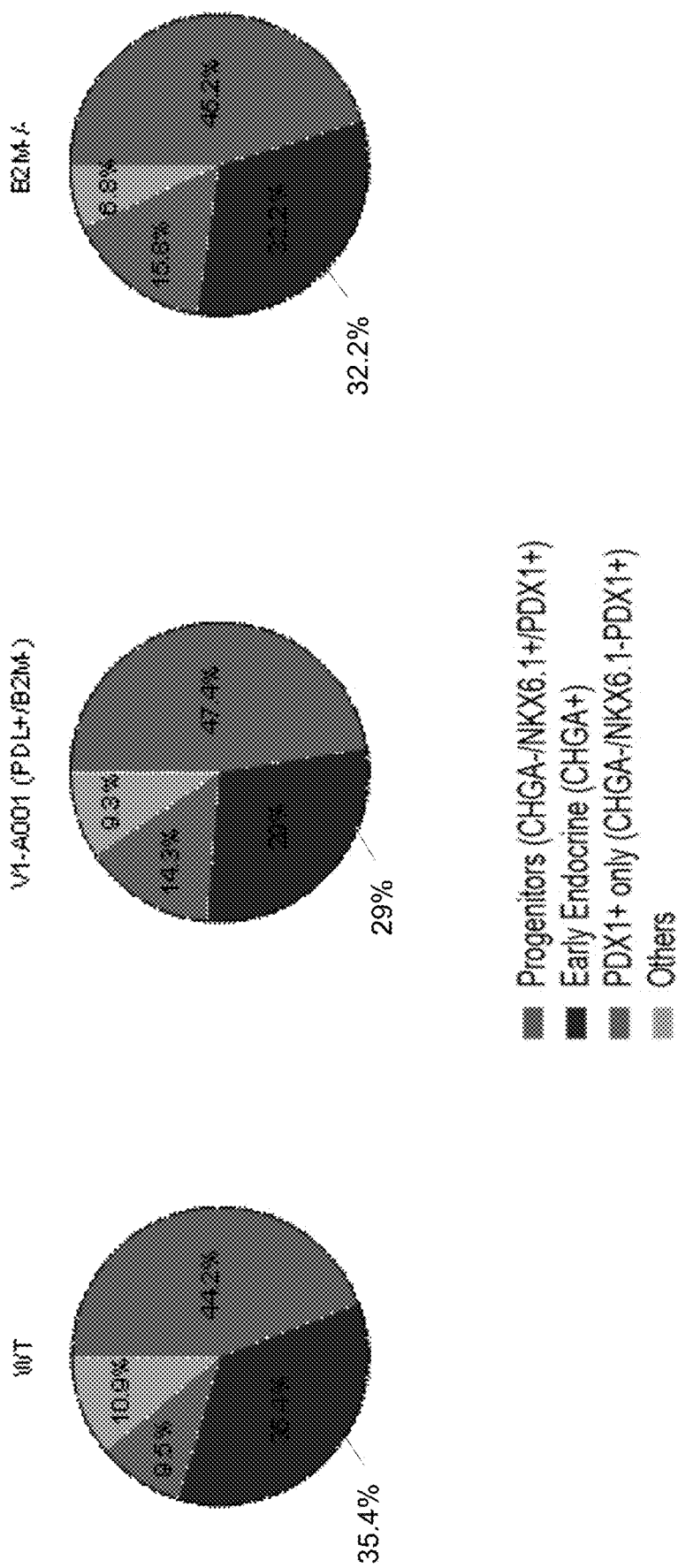
FIG. 20 shows heterogeneous populations of cells at Stage 4 (PEC).

At PECs stage, flow cytometry for chromogranin (CHGA), PDX1 and NKX6.1 was performed. The heterogeneous population at PEC stage include pancreatic progenitors, early endocrine (FIG. 19). From the pie chart of heterogeneous population (FIG. 20), the distribution of cell populations from differentiated edited cells (PD-L1 KI/B2M KO or B2M KO) were very similar to wild type cells.

Targeted RNAseq.

Figure 21A:
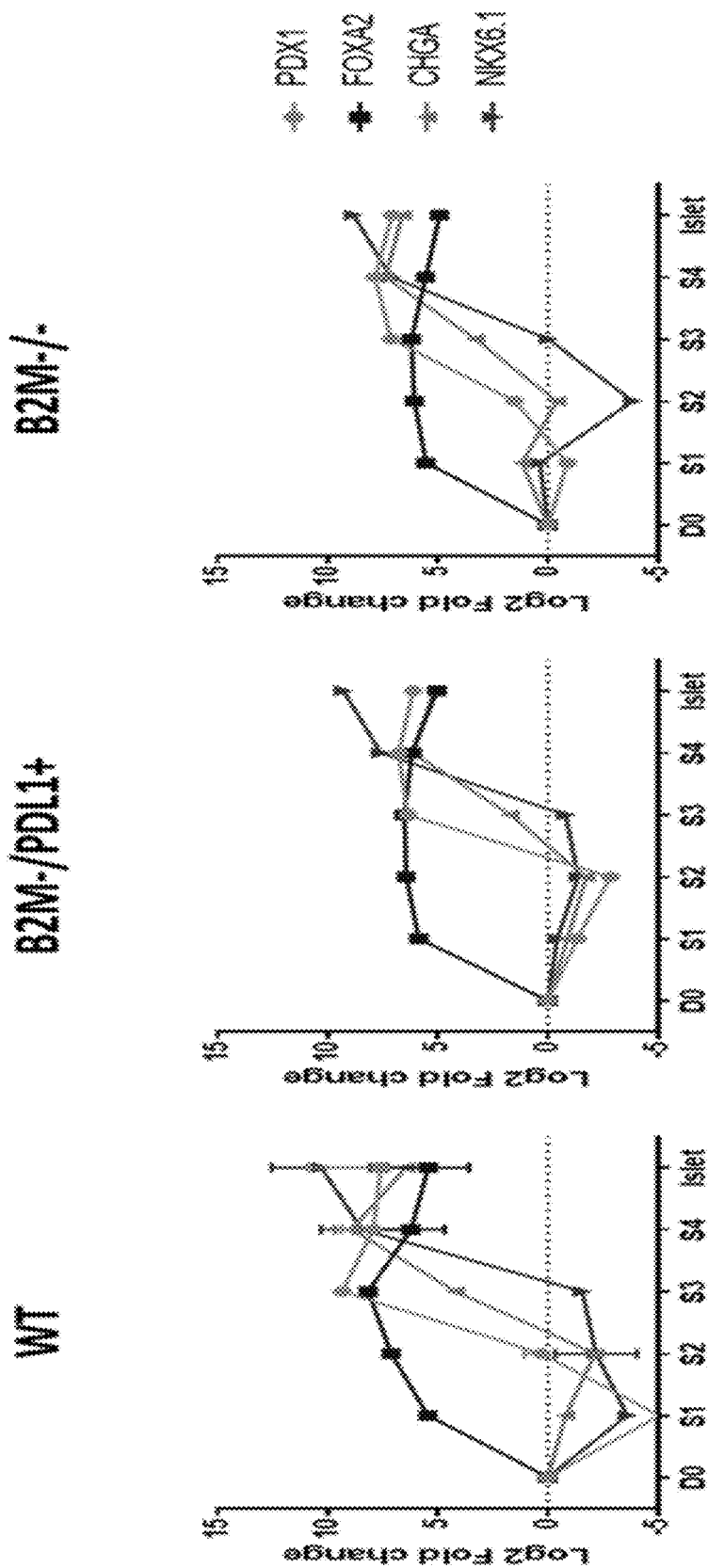
FIGS. 21A-21B show selected gene expression over differentiation time course in cells differentiated from wild type, PD-L1KI/B2MKO, or B2MKO cells (FIG. 21A) and cells differentiated from B2M KO/HLA-E KI (V2A) cells (FIG. 21B).
Figure 21B:
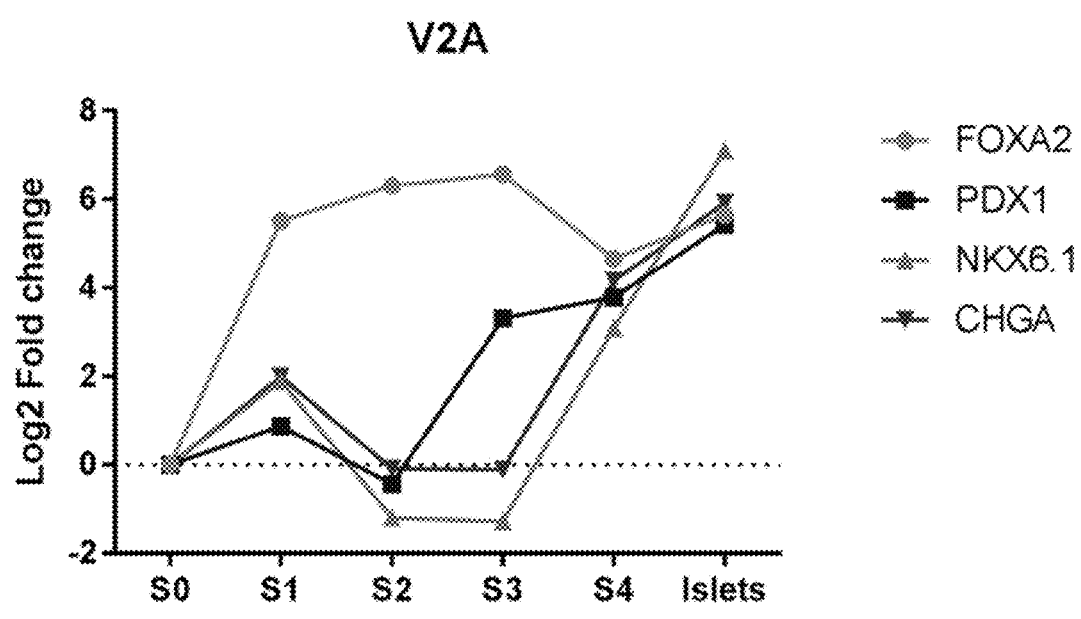
Figure 22A:
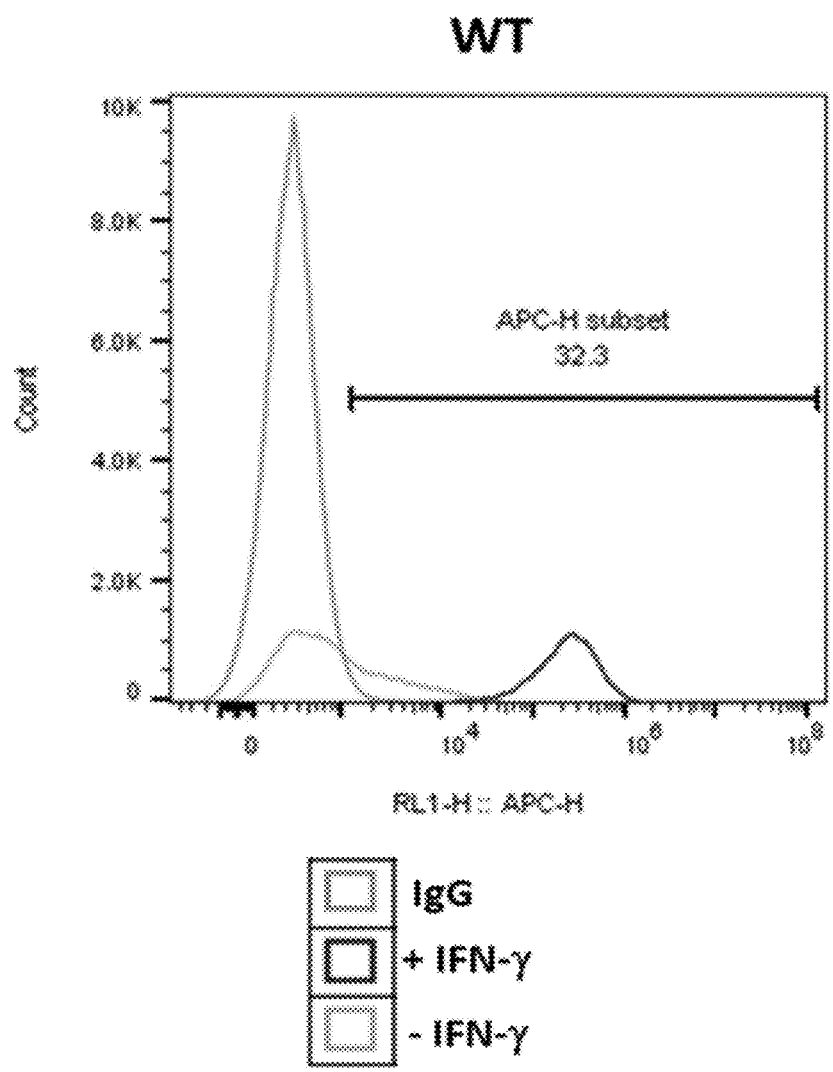
FIGS. 22A-22F show B2M and PD-L1 expression at PEC stage in cells differentiated from wild type, PD-L1 KI/B2M KO, or B2M KO cells.
Figure 22B:
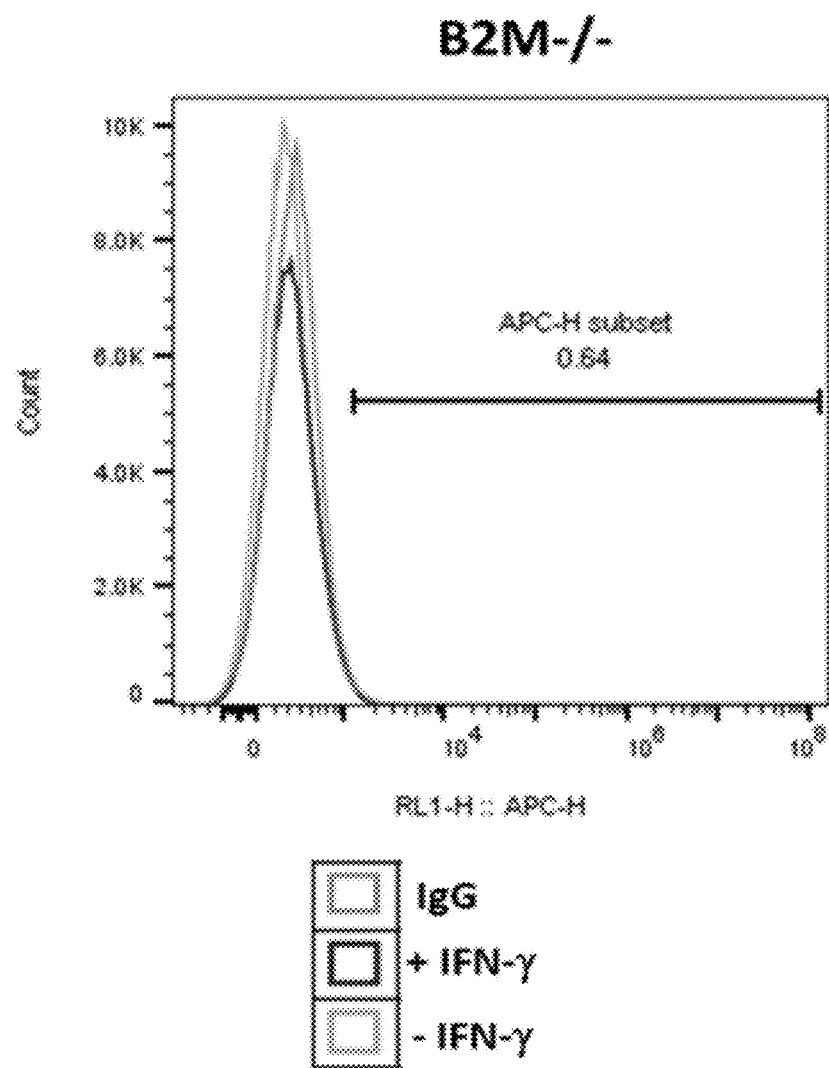
Figure 22C:
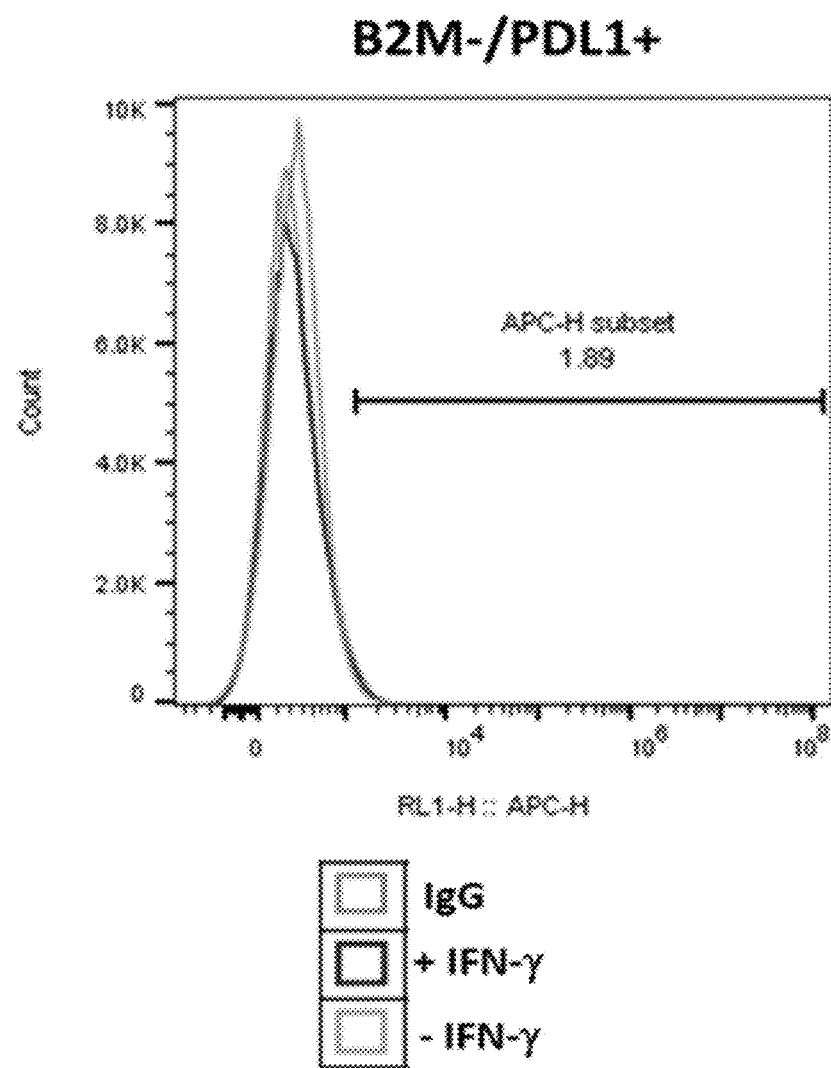
Figure 22D:
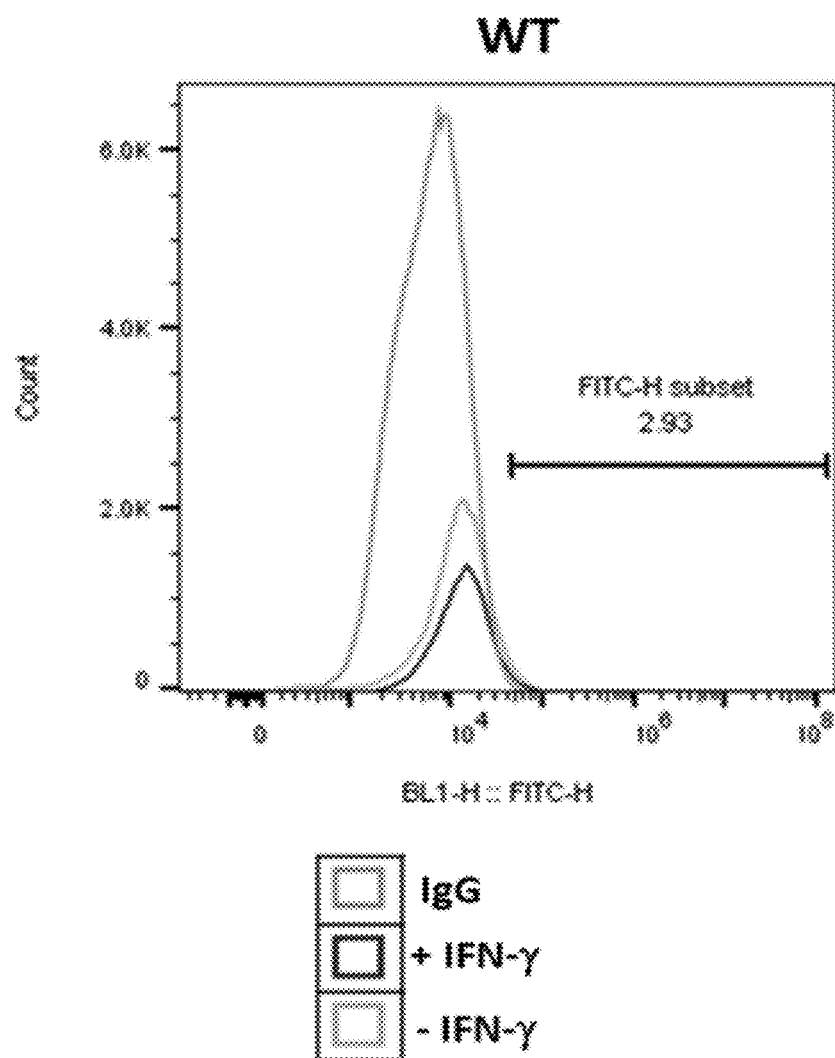
Figure 22E:
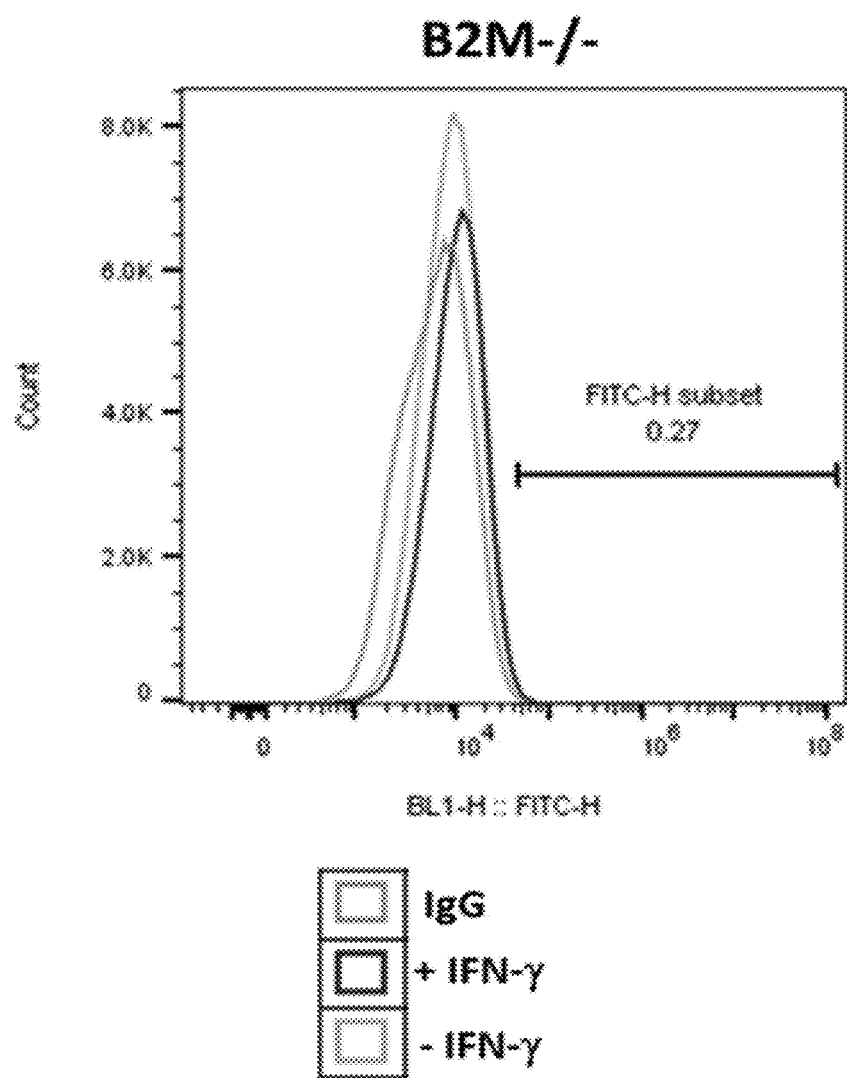
Figure 22F:
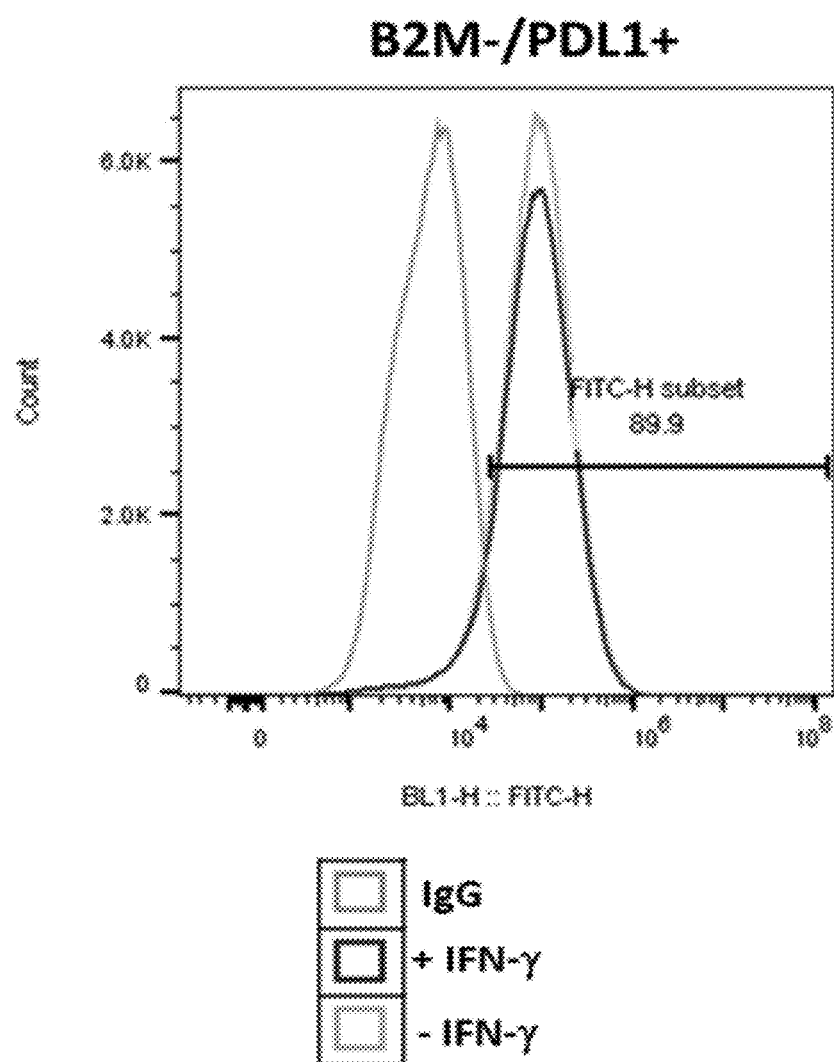

Targeted RNAseq for gene expression analysis was performed using Illumina TuSeq and a custom panel of oligos targeting 111 genes. The panel primarily contained genes that are markers of the developmental stages during pancreatic differentiation. At end of each differentiation stage, 10 µL APV (aggregated pellet volume) was collected and extracted using the Qiagen RNeasy or RNeasy 96 spin column protocol, including on-column DNase treatment. Quantification and quality control were performed using either the TapeStation combined with Qubit, or by using the Qiagen QIAxcel. 50-200 ng of RNA was processed according to the Illumina TruSeq library preparation protocol, which consists of cDNA synthesis, hybridization of the custom oligo pool, washing, extension, ligation of the bound oligos, PCR amplification of the libraries, and clean-up of the libraries, prior to quantification and quality control of the resulting dsDNA libraries using either the TapeStation combined with Qubit, or by using the Qiagen QIAxcel. The libraries were subsequently diluted to a concentration of 4 nM and pooled, followed by denaturing, spike in of PhiX control, and further dilution to 10-12 µM prior to loading on the Illumina MiSeq sequencer. Following the sequencing run, initial data analysis was performed automatically through BaseSpace, generating raw read counts for each of the custom probes. For each gene, these read counts were then summed for all probes corresponding to that gene, with the addition of 1 read count (to prevent downstream divisions by 0). Normalization was performed to the gene SF3B2, and the reads were typically visualized as fold change vs. Stage 0. When the data was processed for principal component analysis, normalization was performed using the DEseq method. Selected gene expression was shown in FIG. 21. The kinetic expression pattern of FOX2, CHGA, PDX1 and NKX6.1 from PD-L1 KI/B2M KO or B2M KO cells was similar to wild type cells.

Confirmation of B2M and PD-L1 Expression at PEC Stage.

At PEC stage, differentiated aggregates were stimulated with or without interferon-gamma (50 ng/ml) for 48 hours. The aggregates washed with PBS and then enzymatically dissociated into single cells suspension at 37° C. using ACCUMAX™ (Catalog #A7089, Sigma, Mo.). MACS Separation Buffer (Cat #130-091-221, Miltenyi Biotec, North Rhine-Westphalia, Germany) was added and the suspension was passed through a 40 μm filter and pelleted. For surface marker staining, dissociated cells were incubated with fluorescent-conjugated antibody diluted in MACS Separation Buffer for 20 mins and then washed in MACS Separation Buffer. Cells were resuspended in FACS buffer for flow acquisition. Flow cytometry data were acquired with NovoCyte Flow Cytometer. As shown the FIGS. 22A-22F, B2M expression was below the detection limit in differentiated PECs from PD-L1 KI/B2M KO or B2M KO, and PDL1 was expressed in the differentiated PECs from PD-L1 KI/B2M KO cells.

Immune Phenotype of PEC Cells.

Figure 23A:
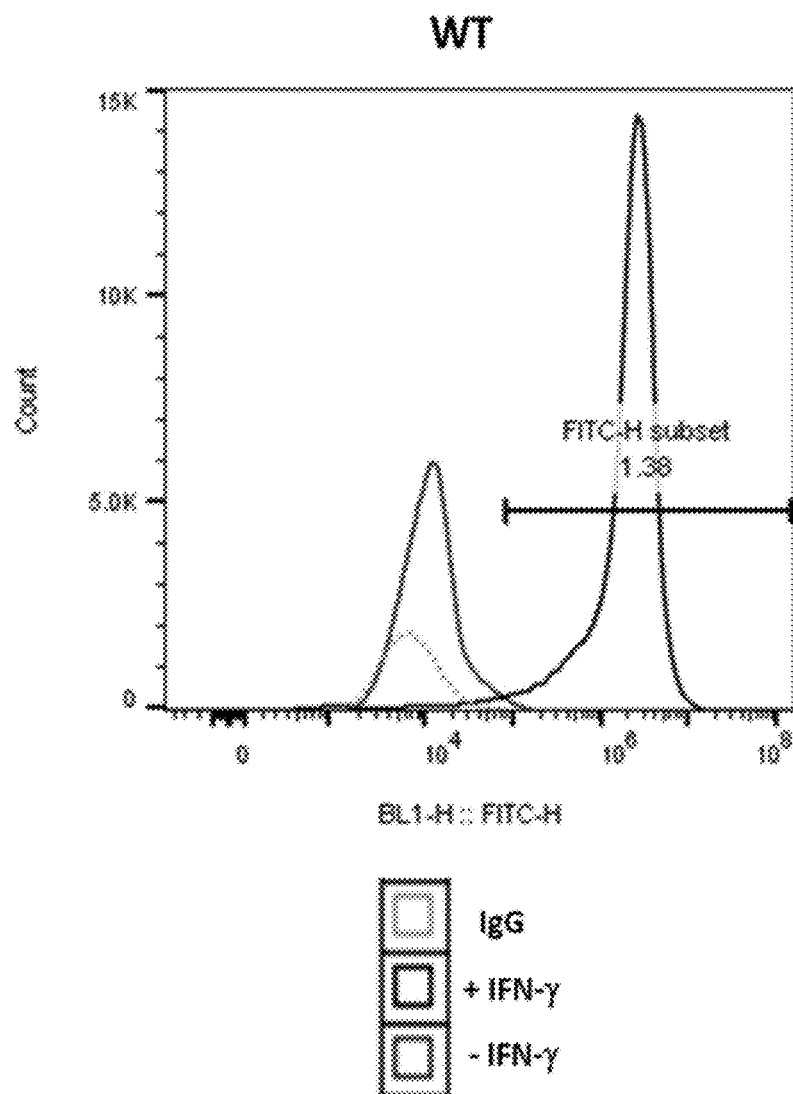
FIGS. 23A-23F show MHC class I and class II expression at PEC stage in cells differentiated from wild type, PD-L1 KI/B2M KO, or B2M KO cells.
Figure 23B:
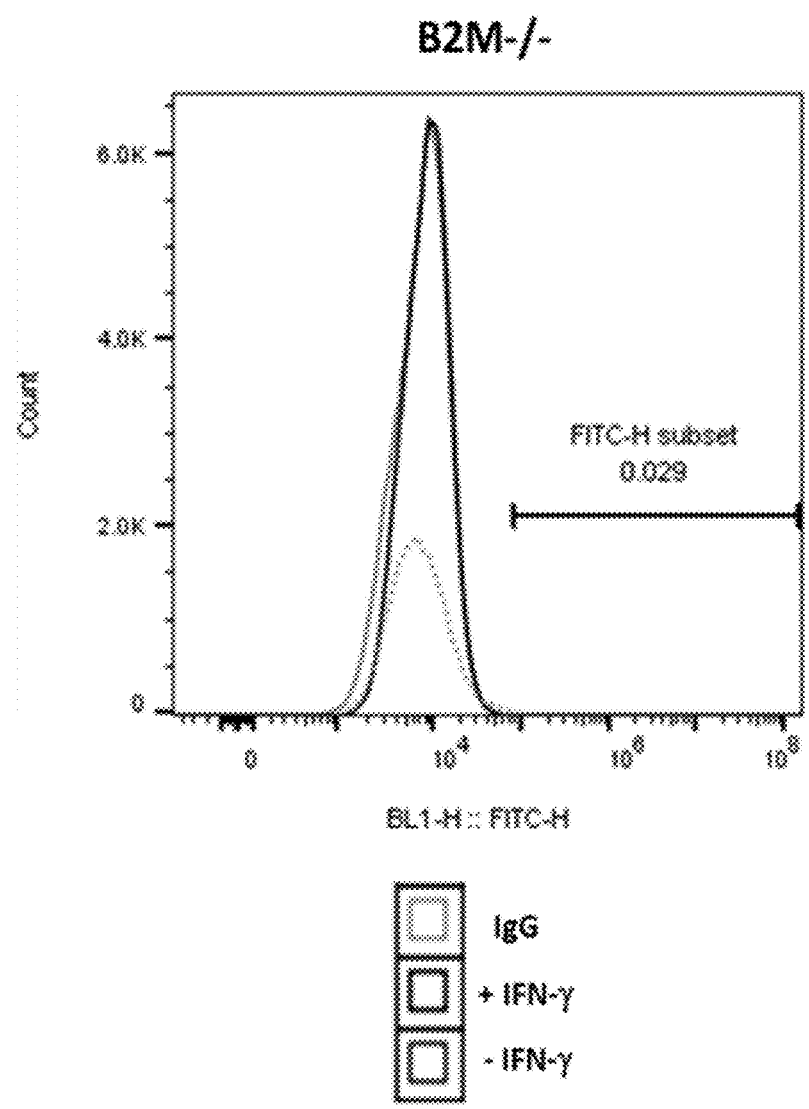
Figure 23C:
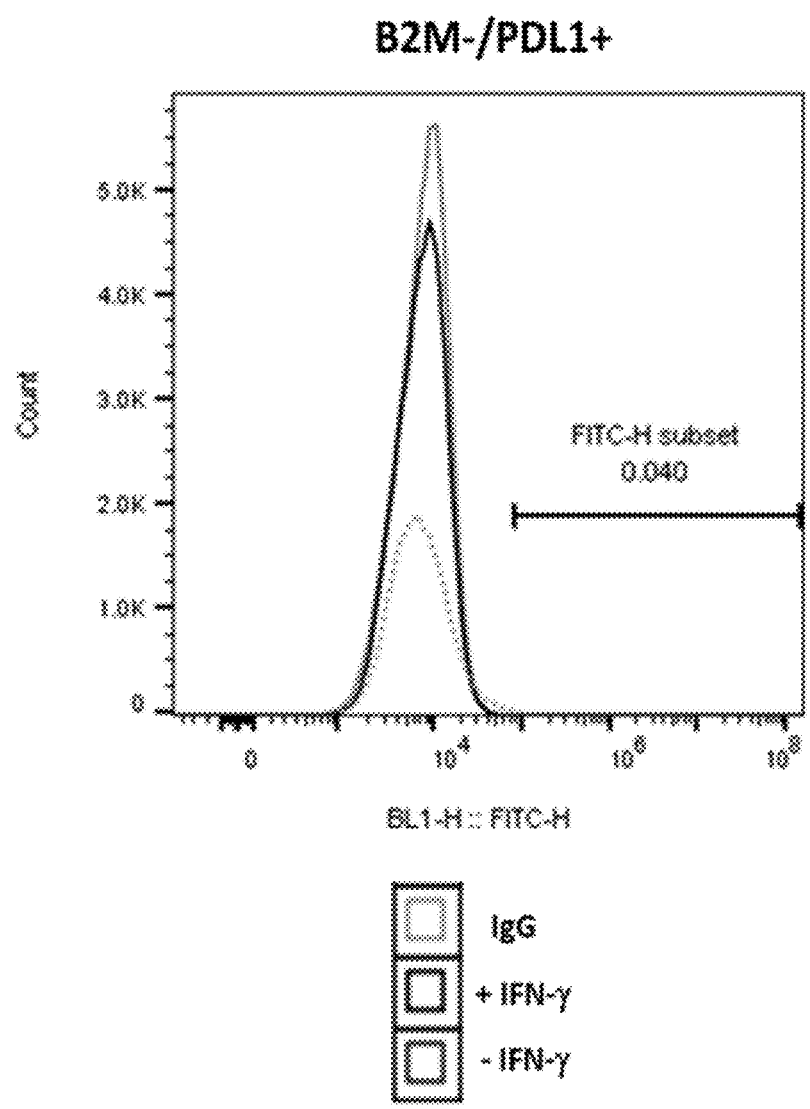
Figure 23D:
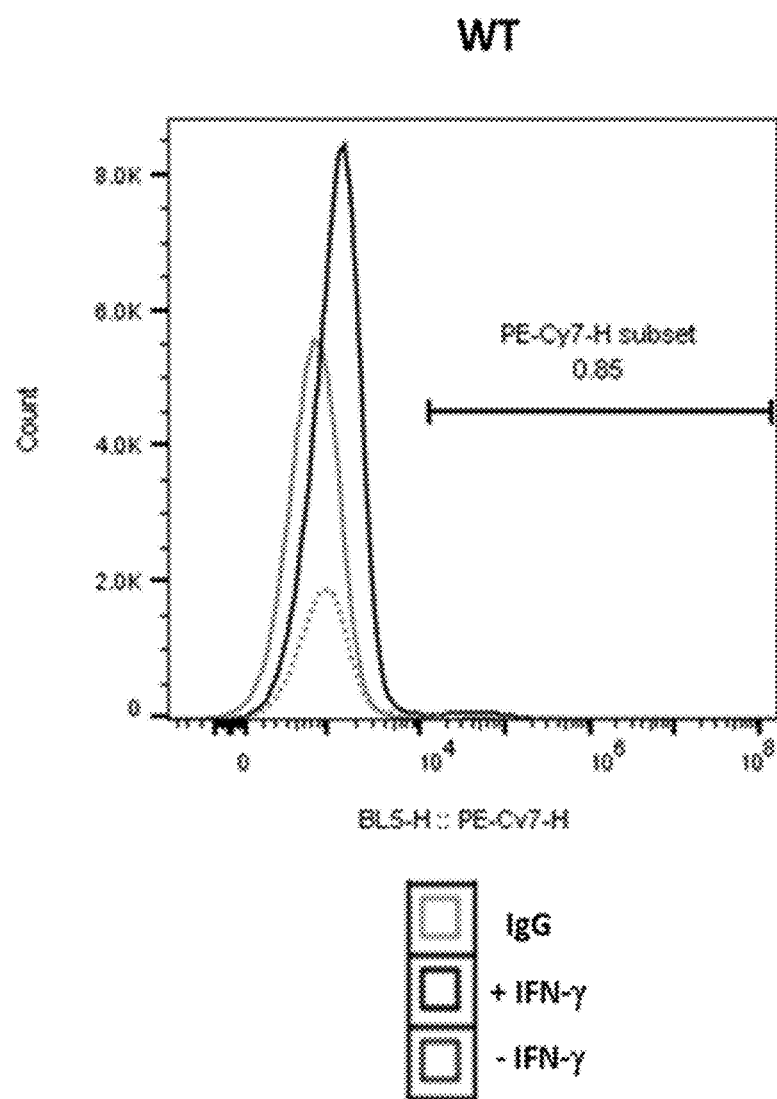
Figure 23E:
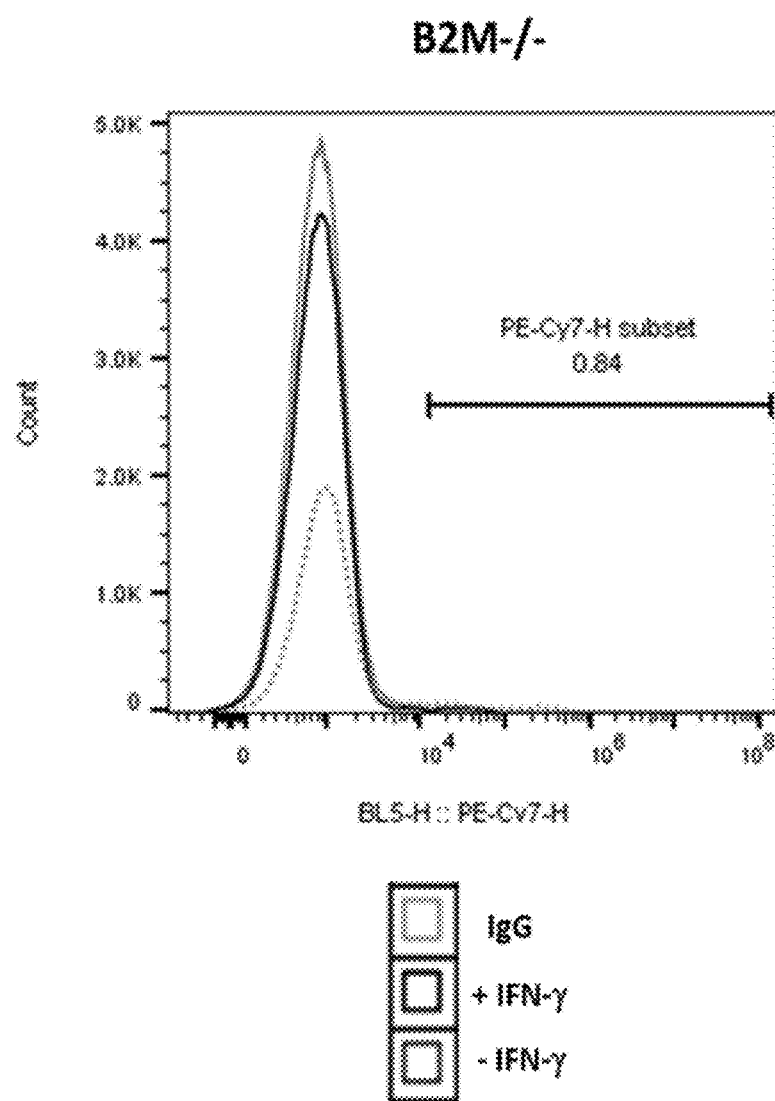
Figure 23F:
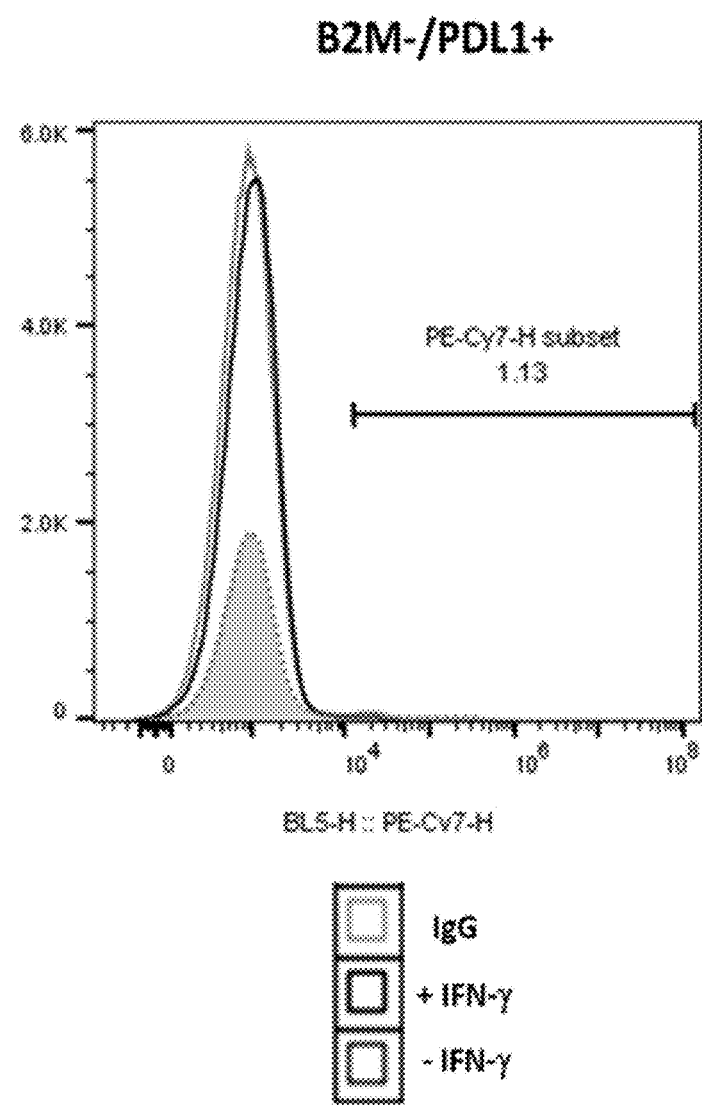
Figure 24A:
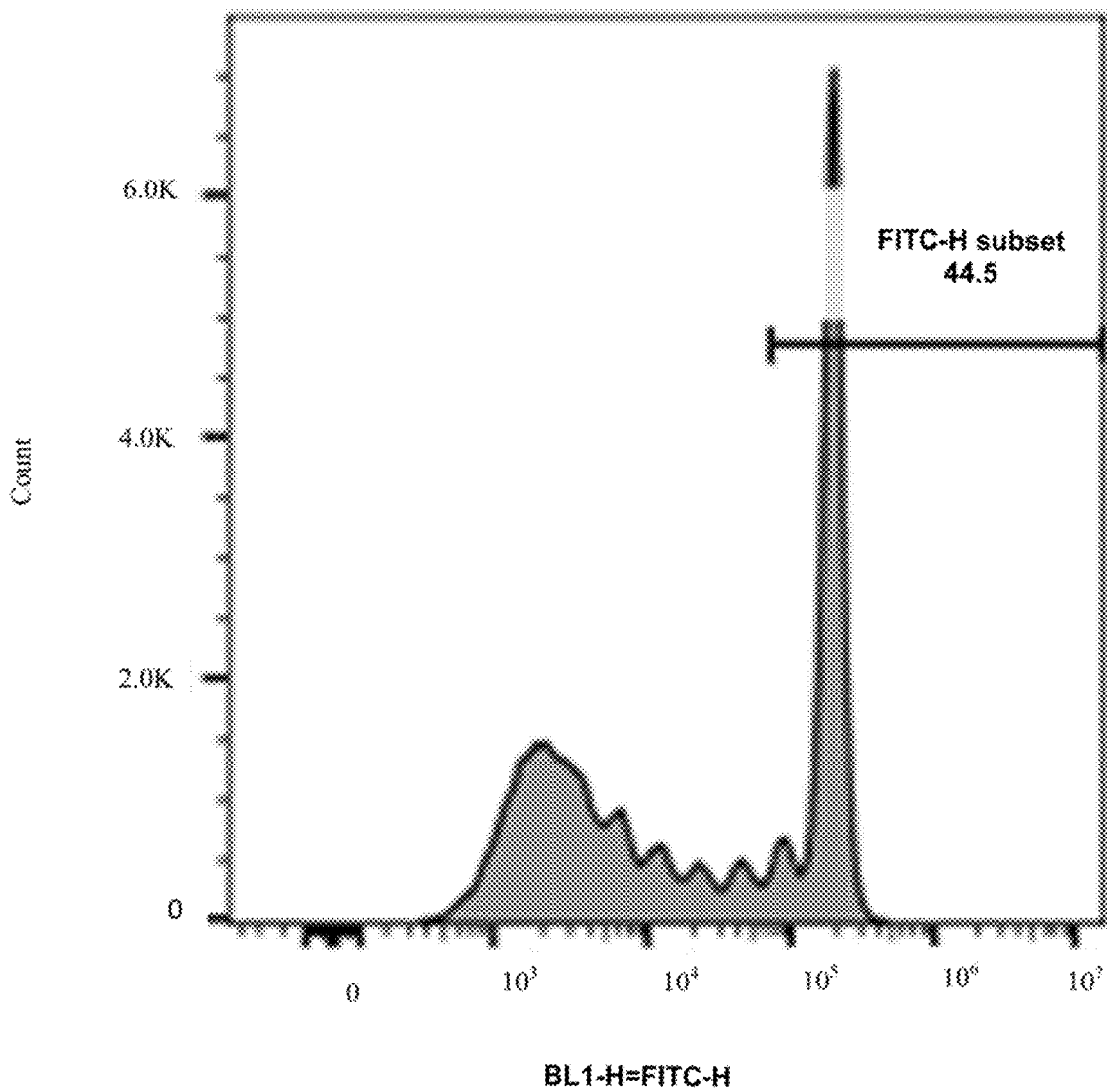
FIGS. 24A-24D show flow cytometry analysis for T-cell activation using the CFSE proliferation assay. Human primary CD3+ T cells were co-incubated with PEC derived from WT, B2M KO, or B2M KO/PD-L1 KI CyT49 clones.
Figure 24B:
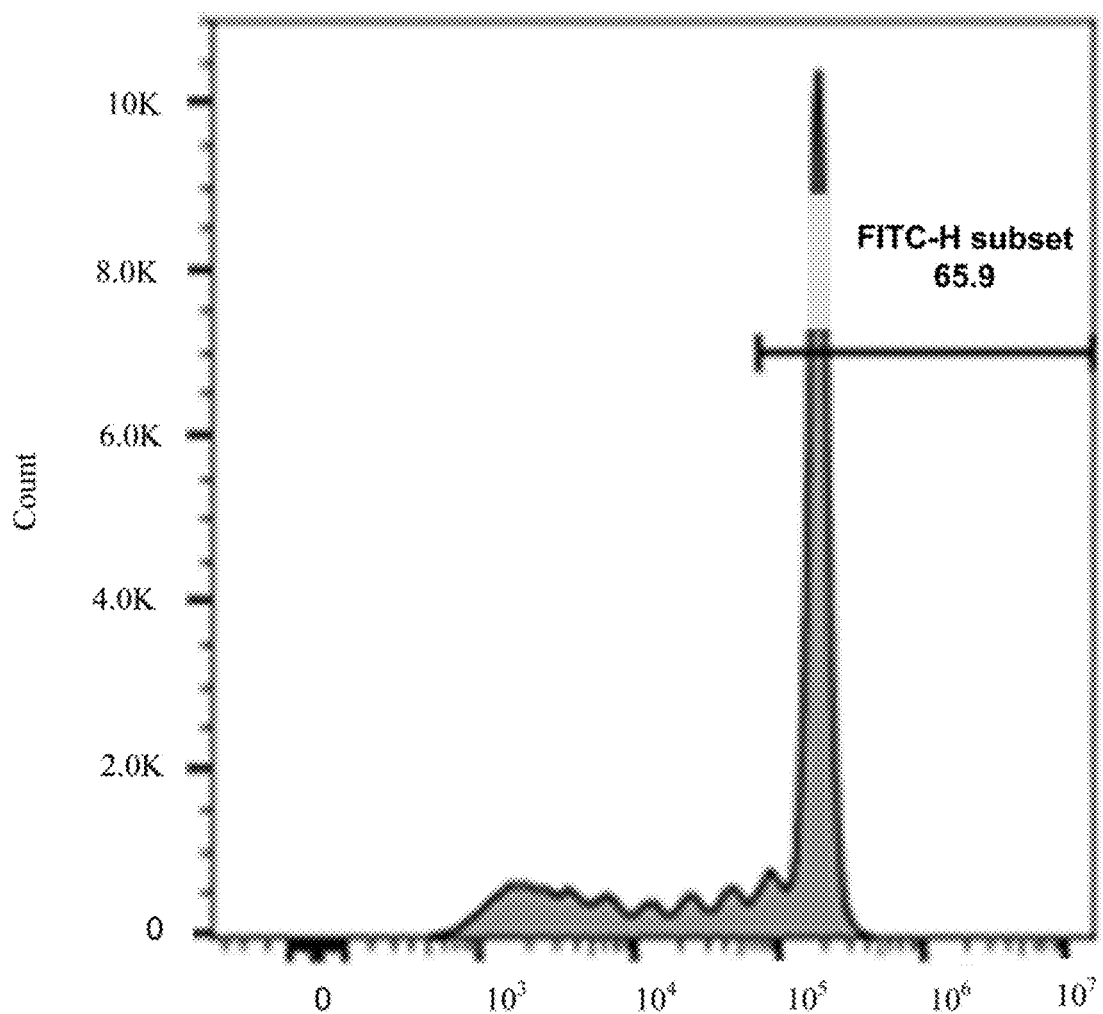
Figure 24C:
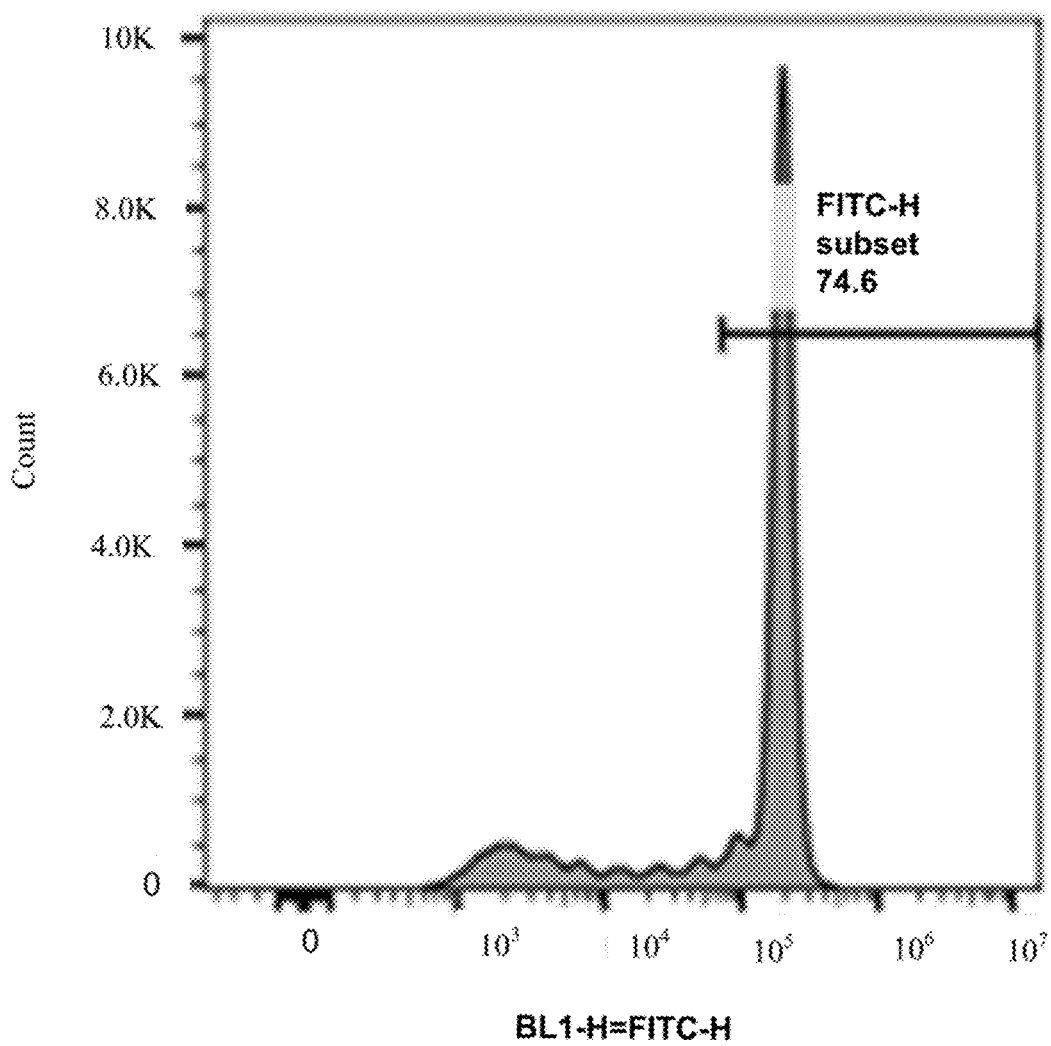
Figure 24D:
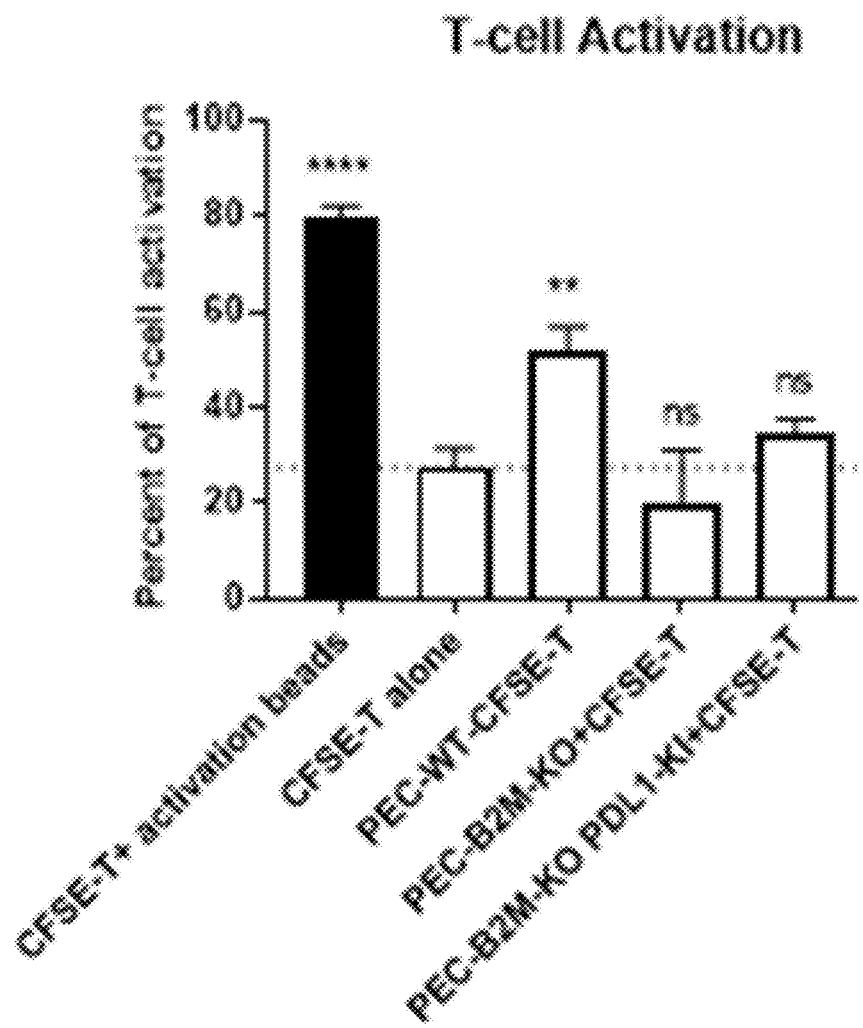

At PEC stage, differentiated aggregates were stimulated with or without interferon-gamma (50 ng/ml) for 48 hours. The aggregates were harvested for MHC class I and II staining. No MHC class II expression at PEC stage from wild type or edited cells (PD-L1 KI/B2M KO and B2M KO cells) (FIGS. 23D-23F). The expression of HLA-ABC (MHC class I) was low (1.3% from wild type cells) and it was highly regulated upon IFN-γ stimulation. However, HLA-ABC was not expressed even under IFN-γ stimulation in the edited cells (PD-L1 KI/B2M KO and B2M KO cells) (FIGS. 23A-23C).

Example 9: T-cell Activation/Proliferation Assay

PEC-differentiated cells were tested for their ability to trigger an immune response via in vitro human T-cell activation/proliferation assays. Fresh donor PBMCs were purchased from Hemacare and CD3+ T-cells were purified using the Pan T-Cell Isolation Kit, human (Miltenyi Cat #130-096-535). The isolated T-cells were labeled with CellTrace™ CFSE Cell Proliferation Kit Protocol (Thermofisher Cat #C34554) per manufacturer instructions and co-incubated with differentiated PEC for 5 days. Dynabeads™ Human T-Activator CD3/CD28 for T-Cell Expansion and Activation (Thermofisher Cat #11161D) were used as a positive control to activate T-cells. T-cells alone were labeled with CFSE and used as a negative control. Percent of CD3+ CFSE+ cells was measured to assess percent of T-cell proliferation (FIGS. 24A-24D). WT PEC triggered T-cell proliferation above T-cell alone control. B2M KO and B2M KO/PD-L1 KI CyT49-derived PEC did not trigger T-cell proliferation above T-cell only control showing the hypo immunogenic nature of edited cells.

The invention claimed is:

1. An in vitro method for generating a universal donor cell, the method comprising delivering to a stem cell:
   (a) a ribonucleoprotein (RNP) complex comprising an RNA-guided nuclease and a guide RNA (gRNA) targeting a target site in a beta-2-microglobulin (B2M) gene locus; and
   (b) a vector comprising a nucleic acid, the nucleic acid comprising (i) a nucleotide sequence homologous with a region located left of the target site in the B2M gene locus, (ii) a nucleotide sequence encoding a tolerogenic factor, and (iii) a nucleotide sequence homologous with a region located right of the target site in the B2M gene locus, wherein the vector comprises a nucleotide sequence consisting of SEQ ID NO: 33,
wherein the B2M gene locus is cleaved at the target site and the nucleic acid is inserted into the B2M gene locus within 50 base pairs of the target site, thereby disrupting the B2M gene and generating a universal donor cell, wherein the universal donor cell has increased immune evasion and/or cell survival compared to a stem cell that does not comprise the nucleic acid inserted into the B2M gene locus.

2. The method of claim 1, wherein the gRNA comprises a spacer sequence corresponding to a target sequence consisting of SEQ ID NO: 1, SEQ ID NO: 2, or SEQ ID NO: 3.

3. The method of claim 1, wherein the nucleotide sequence of (i) consists essentially of SEQ ID NO: 13, and the nucleotide sequence of (iii) consists essentially of SEQ ID NO: 19.

4. The method of claim 1, wherein the vector is a plasmid vector.

5. The method of claim 1, wherein the RNA-guided nuclease is a Cas9 nuclease.

6. The method of claim 5, wherein the Cas9 nuclease is linked to at least one nuclear localization signal.

7. The method of claim 6, wherein the Cas9 nuclease is a S. pyogenes Cas9.

8. The method of claim 1, wherein the stem cell is an embryonic stem cell, an adult stem cell, an induced pluripotent stem cell, or a hematopoietic stem and progenitor cell.

9. The method of claim 1, wherein the stem cell is a human stem cell.

10. An in vitro method for generating a universal donor cell, the method comprising delivering to a stem cell:
    (a) a ribonucleoprotein (RNP) complex comprising an RNA-guided nuclease and a guide RNA (gRNA) targeting a target site in a beta-2-microglobulin (B2M) gene locus, wherein the gRNA comprises a spacer sequence corresponding to a target sequence consisting of SEQ ID NO: 2; and
    (b) a vector comprising a nucleic acid, the nucleic acid comprising (i) a nucleotide sequence homologous with a region located left of the target site in the B2M gene locus, wherein the nucleotide sequence consists essentially of SEQ ID NO: 13, (ii) a nucleotide sequence encoding a tolerogenic factor, and (iii) a nucleotide sequence homologous with a region located right of the target site in the B2M gene locus, wherein the nucleotide sequence consists essentially of SEQ ID NO:19, wherein the vector comprises a nucleotide sequence consisting of SEQ ID NO: 33,
wherein the B2M gene locus is cleaved at the target site and the nucleic acid is inserted into the B2M gene locus within 50 base pairs of the target site, thereby disrupting the B2M gene and generating the universal donor cell, wherein the universal donor cell has increased immune evasion and/or cell survival compared to a stem cell that does not comprise the nucleic acid inserted into the B2M gene locus.

11. The method of claim 10, wherein the vector is a plasmid vector.

12. The method of claim 10, wherein the RNA-guided nuclease is a Cas9 nuclease.

13. The method of claim 12, wherein the Cas9 nuclease is linked to at least one nuclear localization signal.

14. The method of claim 13, wherein the Cas9 nuclease is a S. pyogenes Cas9.

15. The method of claim 10, wherein the stem cell is an embryonic stem cell, an adult stem cell, an induced pluripotent stem cell, or a hematopoietic stem and progenitor cell.

16. The method of claim 10, wherein the stem cell is a human stem cell.

* * * * *